US012618843B2

(12) United States Patent
Campbell et al.

(10) Patent No.: US 12,618,843 B2
(45) Date of Patent: May 5, 2026

(54) BIOMARKER COMBINATIONS FOR DETERMINING AGGRESSIVE PROSTATE CANCER

(71) Applicant: MINOMIC INTERNATIONAL LTD., New South Wales (AU)

(72) Inventors: Douglas Campbell, New South Wales (AU); Thao Ho-Le, New South Wales (AU); Brad Walsh, New South Wales (AU); Rachel Levin, New South Wales (AU)

(73) Assignee: MINOMIC INTERNATIONAL LTD., New South Wales (AU)

( * ) Notice: Subject to any disclaimer, the term of this patent is extended or adjusted under 35 U.S.C. 154(b) by 1215 days.

(21) Appl. No.: 17/282,612

(22) PCT Filed: Oct. 4, 2019

(86) PCT No.: PCT/AU2019/051080
§ 371 (c)(1),
(2) Date: Apr. 2, 2021

(87) PCT Pub. No.: WO2020/069580
PCT Pub. Date: Apr. 9, 2020

(65) Prior Publication Data
US 2023/0333111 A1 Oct. 19, 2023

(30) Foreign Application Priority Data

Oct. 5, 2018 (AU) ................................ 2018903763
Feb. 8, 2019 (AU) ................................ 2019900406

(51) Int. Cl.
*G01N 33/574* (2006.01)
*G01N 33/50* (2006.01)
*G01N 33/74* (2006.01)
(52) U.S. Cl.
CPC ....... *G01N 33/57434* (2013.01); *G01N 33/50* (2013.01); *G01N 33/74* (2013.01); *G01N 2333/82* (2013.01); *G01N 2800/56* (2013.01); *G01N 2800/60* (2013.01)

(58) Field of Classification Search
None
See application file for complete search history.

(56) References Cited

U.S. PATENT DOCUMENTS

2018/0224454 A1 8/2018 Walsh et al.

OTHER PUBLICATIONS

Fontana et al. 'Leptin increases prostate cancer aggressiveness.' J. Physiol. Biochem. 67:531-538, 2011.*
Fontana et al., "Leptin increases prostate cancer aggressiveness," J Physiol Biochem, 2011, 67:531-538.
Forootan et al., "Prognostic significance of osteopontin expression in human prostate cancer," Int J Cancer, 2006, 118:2255-2261.
Sağlam et al., "Leptin Influences Cellular Differentiation and Progression in Prostate Cancer," J of Urol, 2003, 169:1308-1311.
Schroten et al., "The additional value of TGFβ1 and IL-7 to predict the course of prostate cancer progression," Cancer Immunol Immunother, 2012, 61:905-910.
Sfar et al., "Combined effects of the angiogenic genes polymorphisms on prostate cancer susceptibility and aggressiveness," Mol Biol Rep, 2009, 36:37-45.
Shore et al., "Development and evaluation of the MiCheck test for aggressive prostate cancer," Urol Oncol, Seminars and Original Investigations, 2020, 38(8):683.e11-683.e18, 8 pp.
International Preliminary Report on Patentability issued Dec. 22, 2020 in PCT/AU2019/051080.
International Search Report and Written Opinion issued Dec. 17, 2019 in PCT/AU2019/051080.

* cited by examiner

*Primary Examiner* — Nora M Rooney
(74) *Attorney, Agent, or Firm* — Womble Bond Dickinson (US) LLP

(57) ABSTRACT

The present invention provides methods for the diagnosis of aggressive prostate cancer, including, but not limited to, methods for discerning between aggressive and non-aggressive forms of prostate cancer, and methods for detecting aggressive prostate cancer based on comparisons to a mixed control population of subjects with non-aggressive prostate cancer or not having prostate cancer.

20 Claims, 19 Drawing Sheets

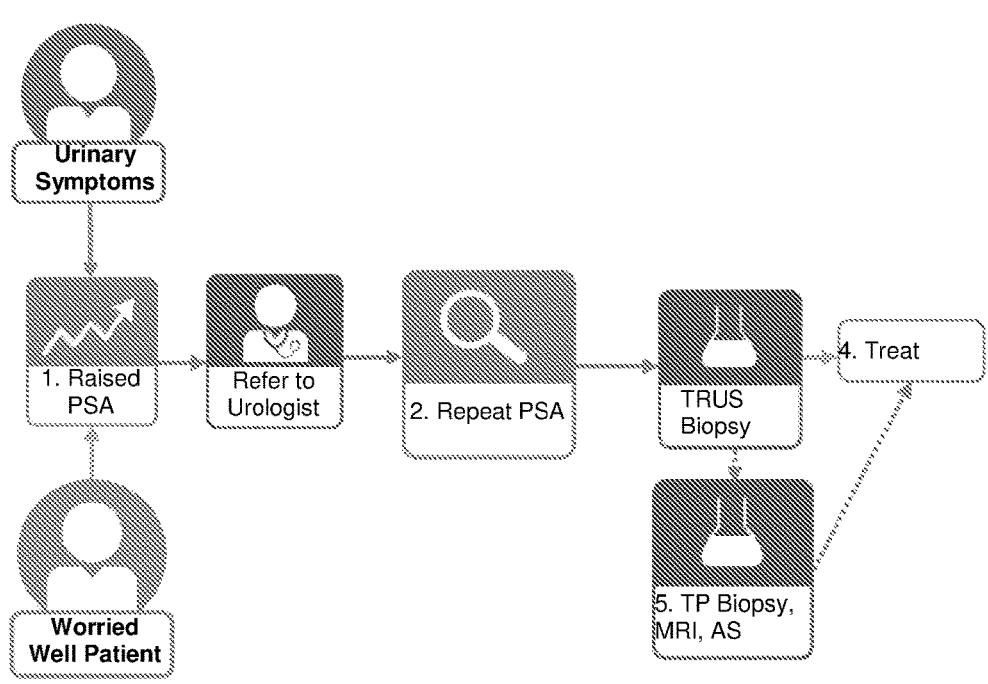
FIGURE ONE
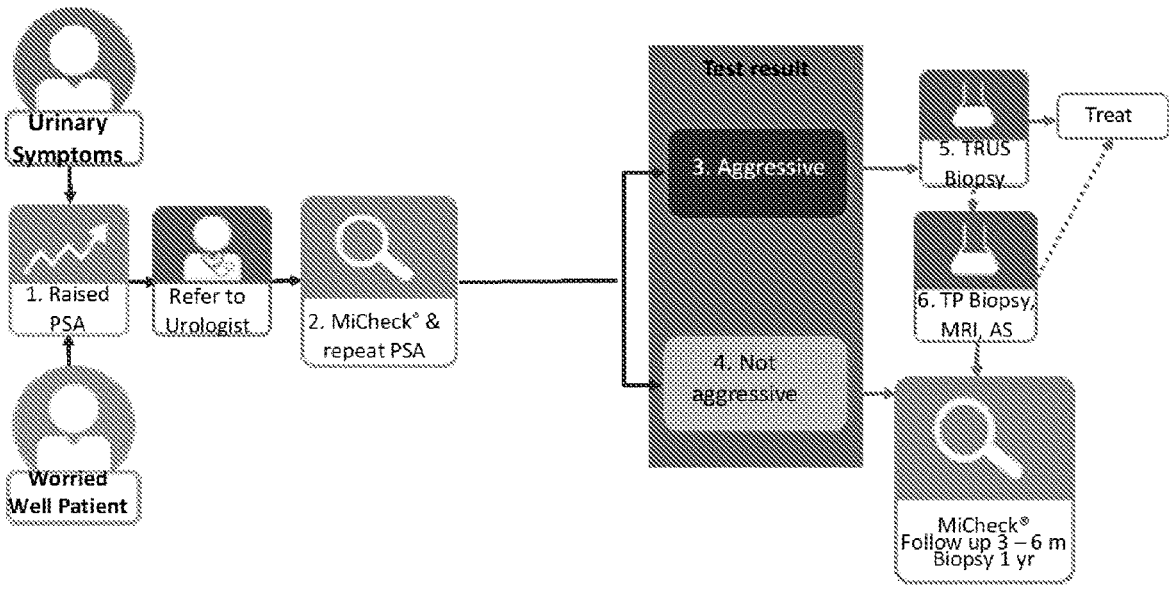
FIGURE TWO

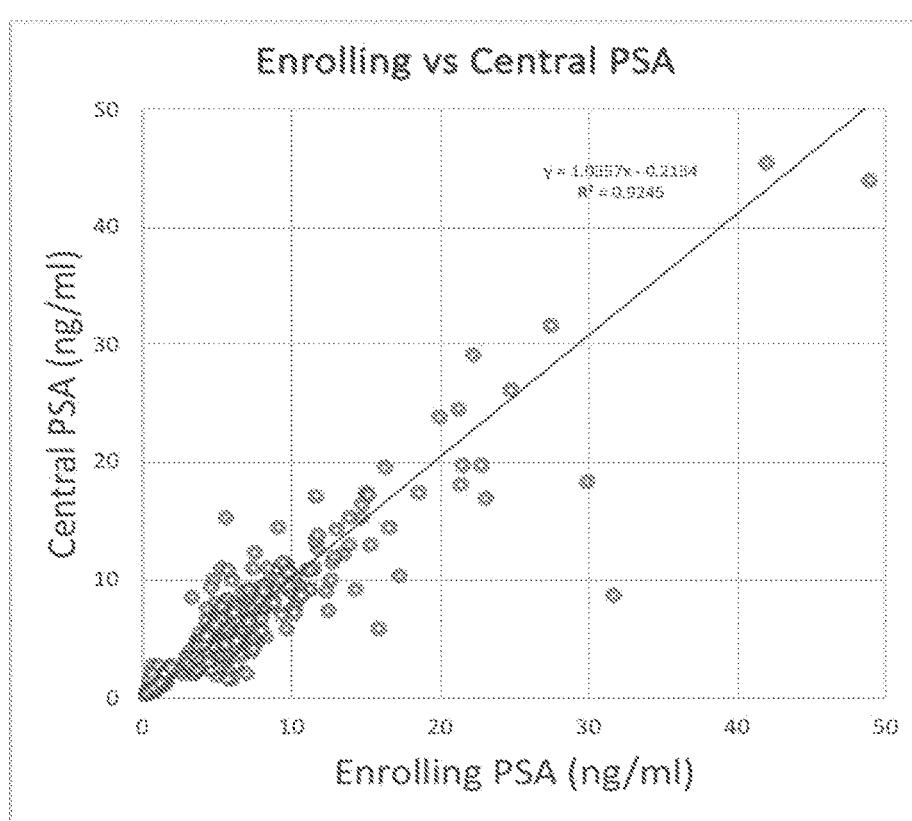
FIGURE THREE
| Site Gleason Score | Central Pathology Gleason Score | | | | | | | |
|---|---|---|---|---|---|---|---|---|
| | Not Scanned | 3+3 | 3+4 | 4+3 | 4+4 | 3+5 | 4+5 | 5+4 |
| Not Scanned | 147 | 4 | 0 | 0 | 0 | 0 | 0 | 0 |
| 3+3 | 1 | 59 | 13 | 1 | 0 | 0 | 0 | 0 |
| 3+4 | 0 | 1 | 43 | 9 | 0 | 1 | 0 | 0 |
| 4+3 | 0 | 0 | 2 | 28 | 0 | 0 | 2 | 0 |
| 4+4 | 0 | 0 | 0 | 5 | 4 | 0 | 1 | 0 |
| 3+5 | 0 | 0 | 0 | 0 | 0 | 0 | 0 | 1 |
| 4+5 | 0 | 0 | 0 | 0 | 0 | 0 | 7 | 0 |
| 5+4 | 0 | 0 | 0 | 0 | 0 | 0 | 1 | 1 |
| 5+5 | 0 | 0 | 0 | 0 | 0 | 0 | 1 | 0 |
FIGURE FOUR

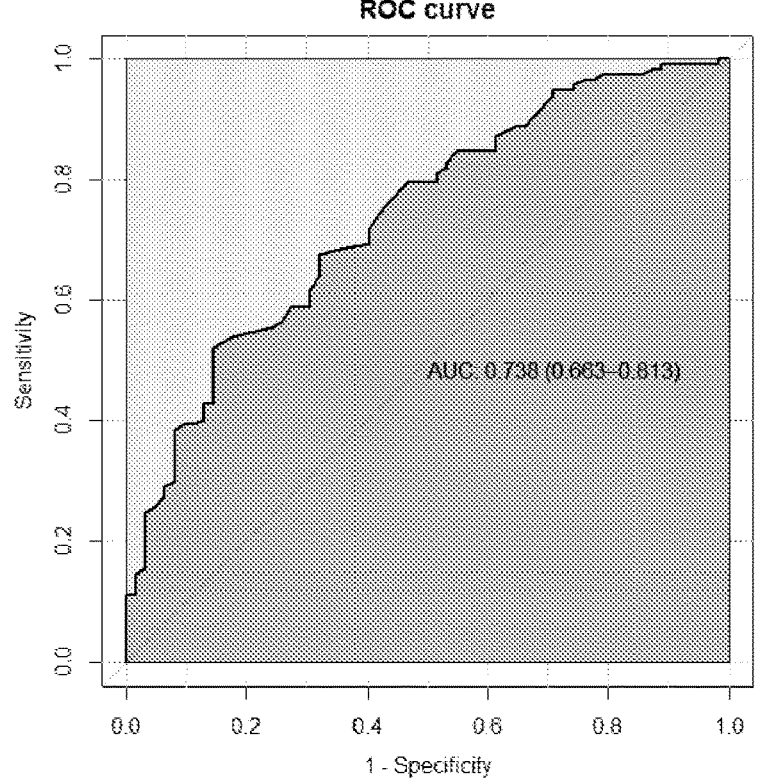
FIGURE FIVE
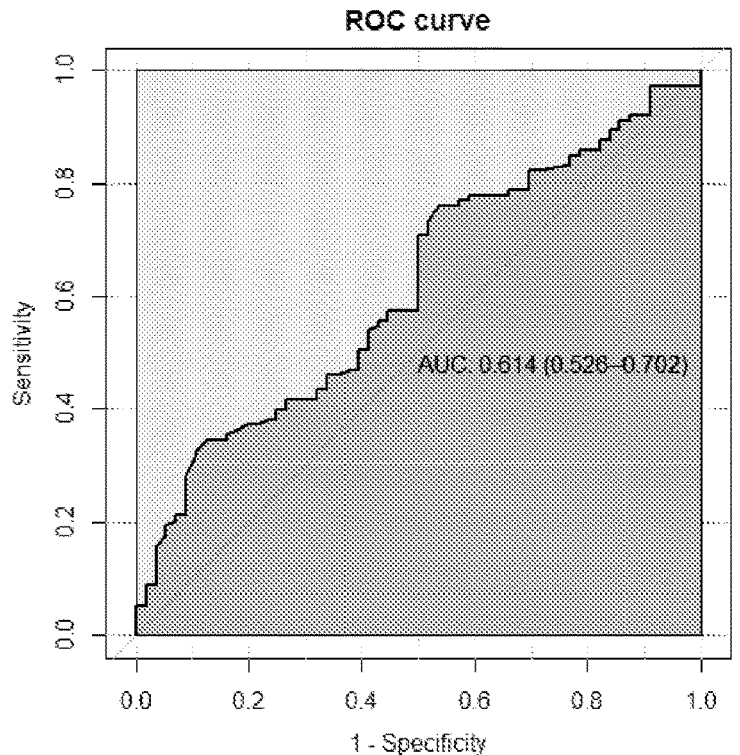
FIGURE SIX

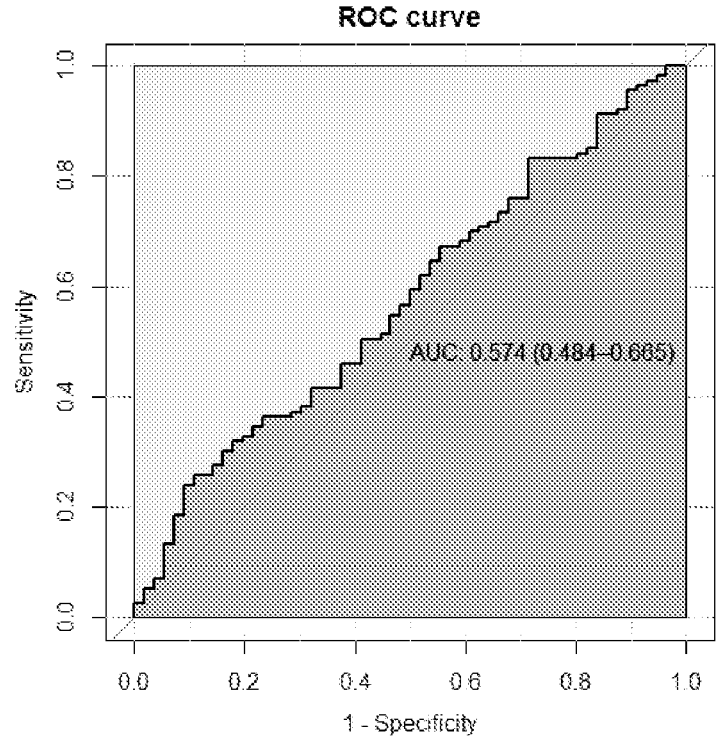
FIGURE SEVEN
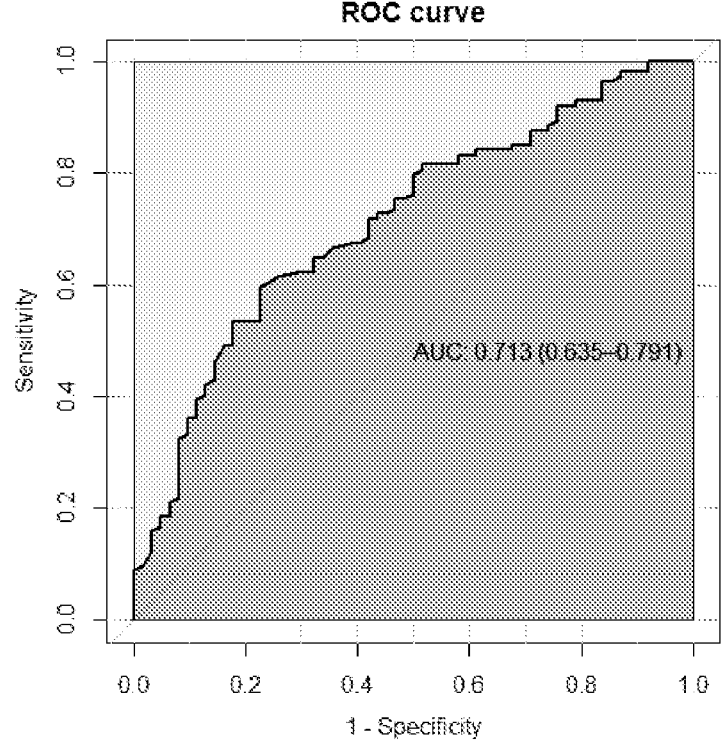
FIGURE EIGHT

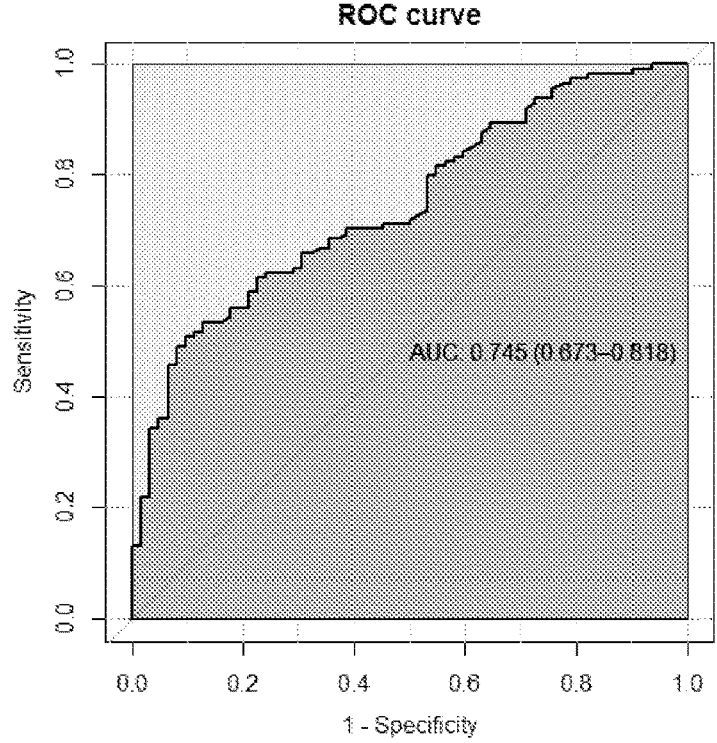
FIGURE NINE
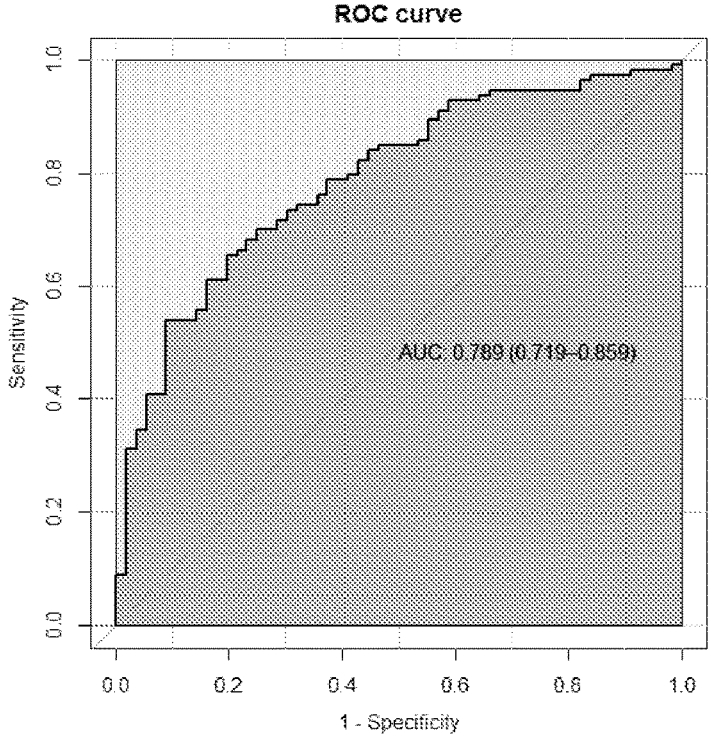
FIGURE TEN

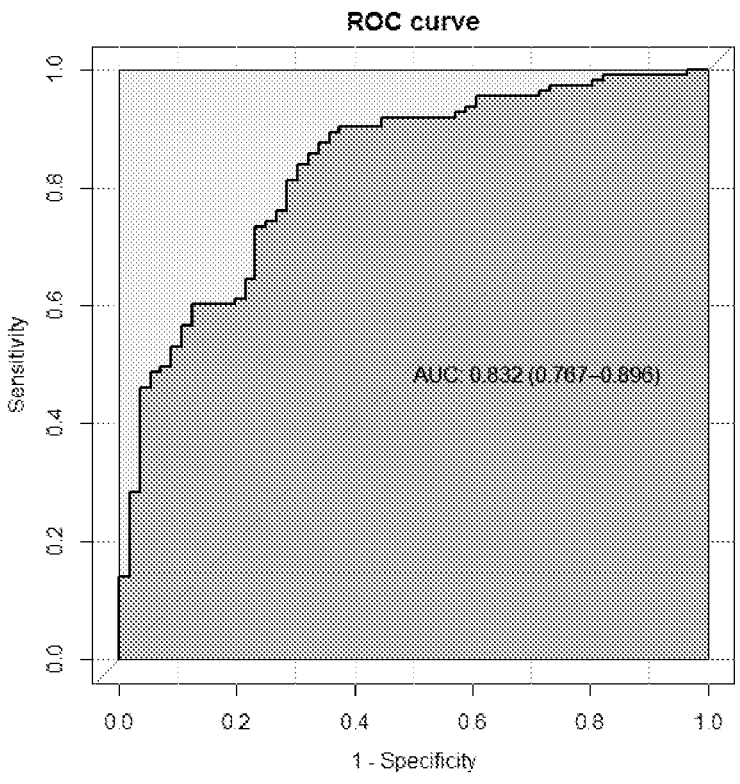
FIGURE ELEVEN
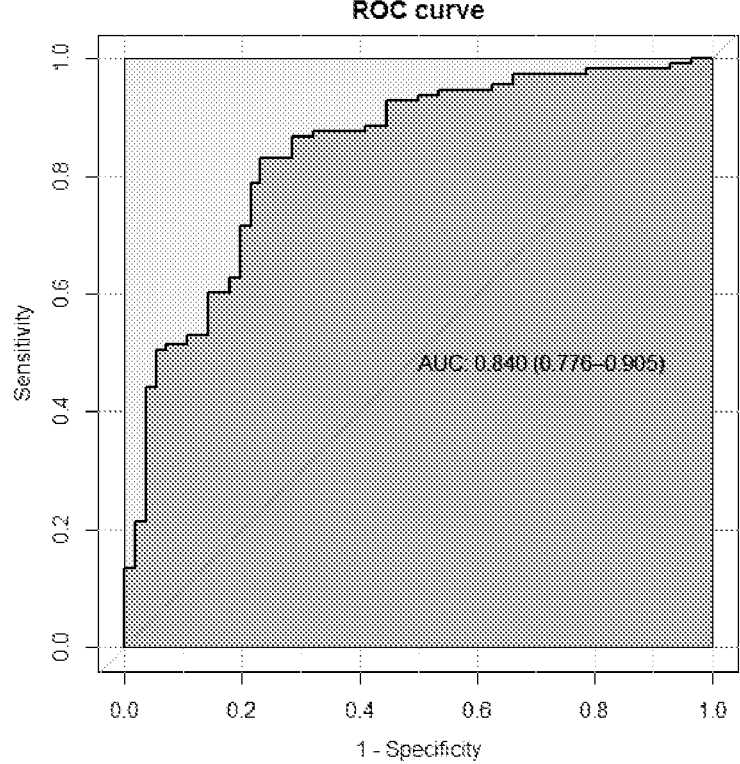
FIGURE TWELVE

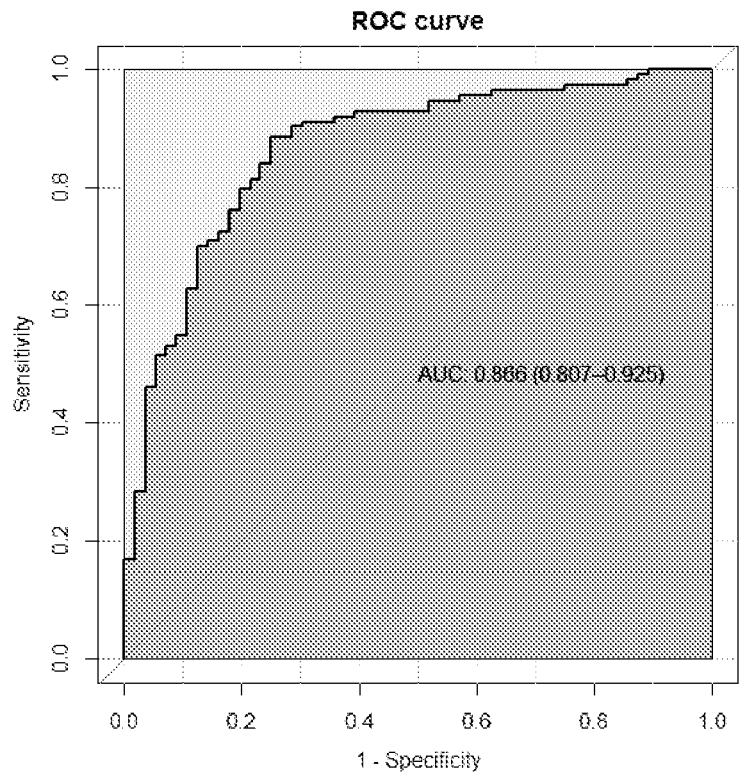
FIGURE THIRTEEN
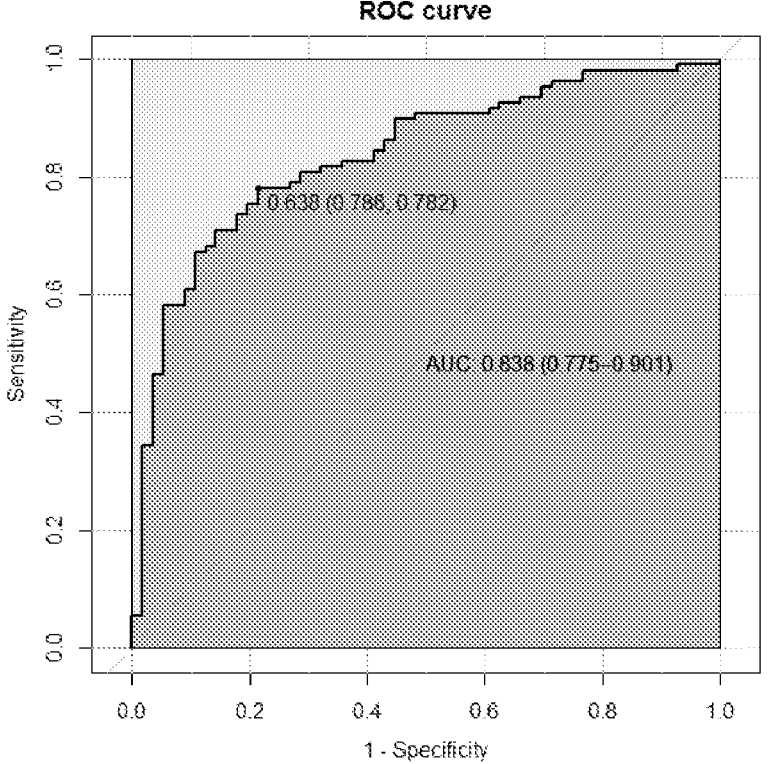
FIGURE FOURTEEN

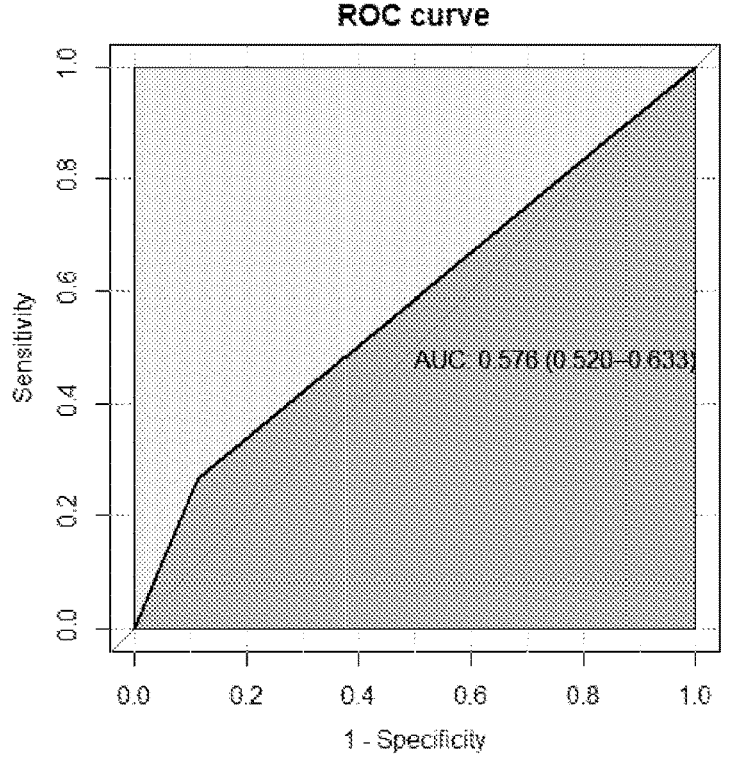
FIGURE FIFTEEN
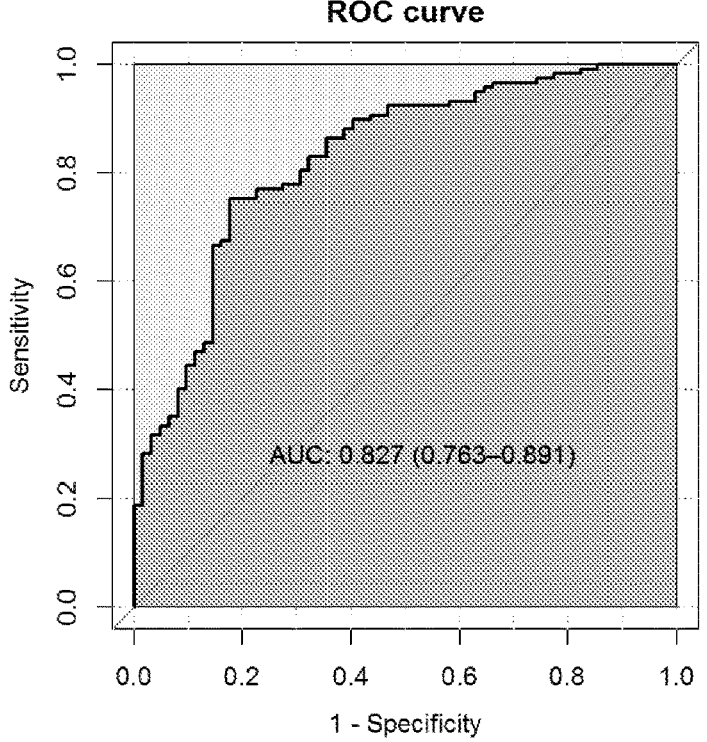
FIGURE SIXTEEN

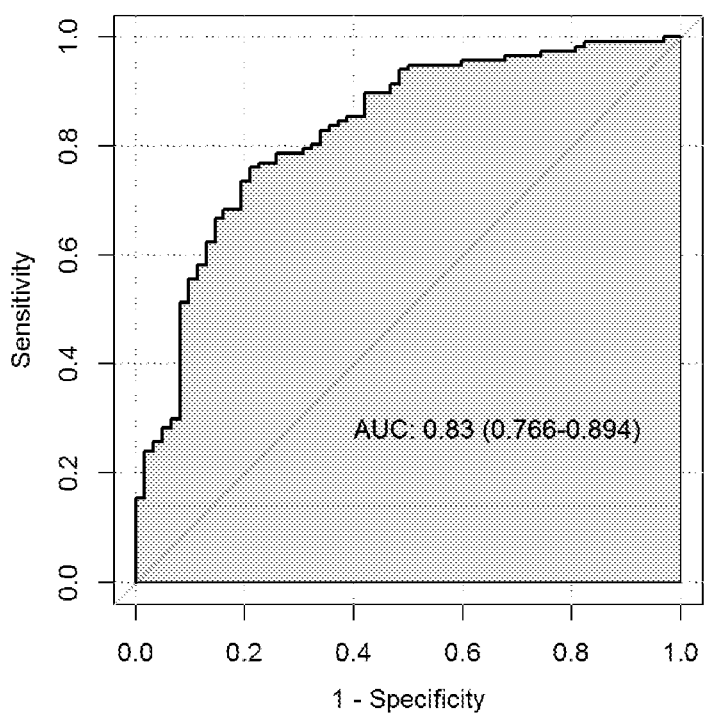
FIGURE SEVENTEEN
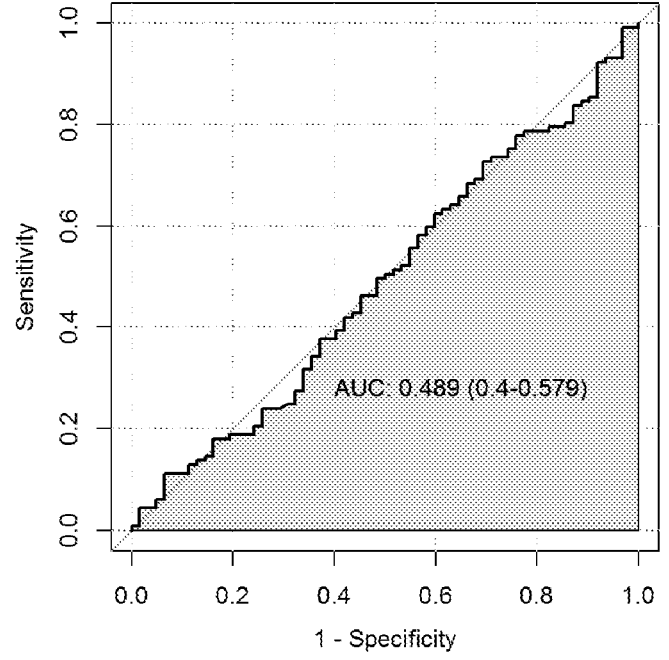
FIGURE EIGHTEEN

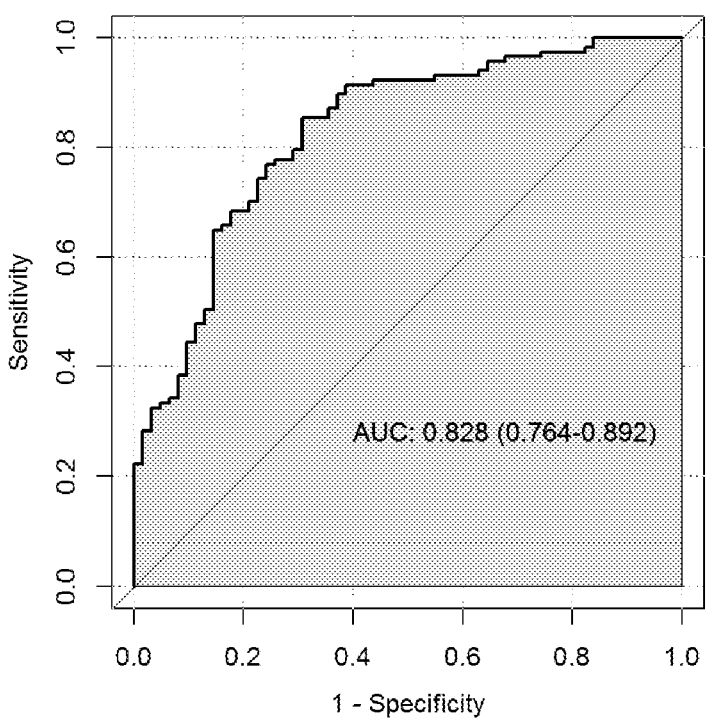
FIGURE NINETEEN
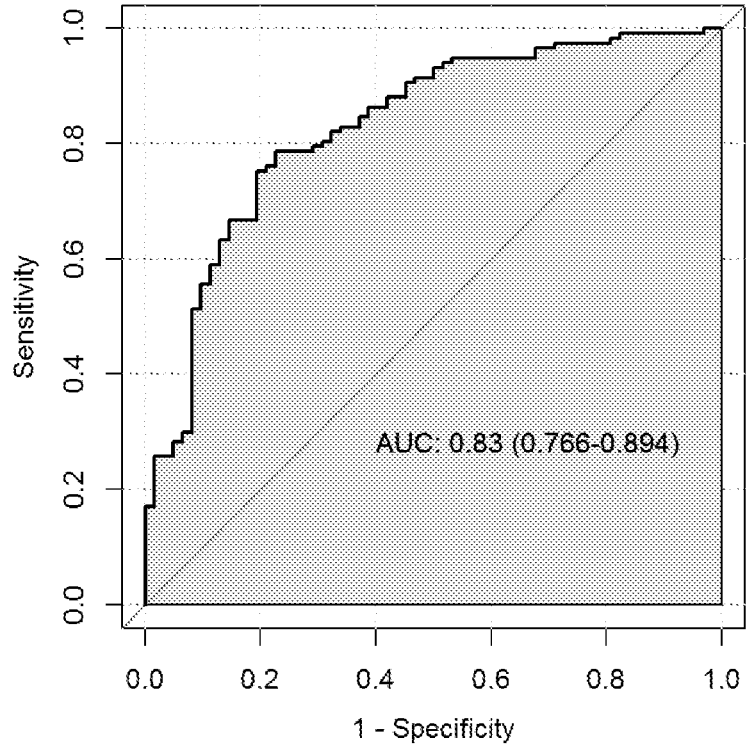
FIGURE TWENTY

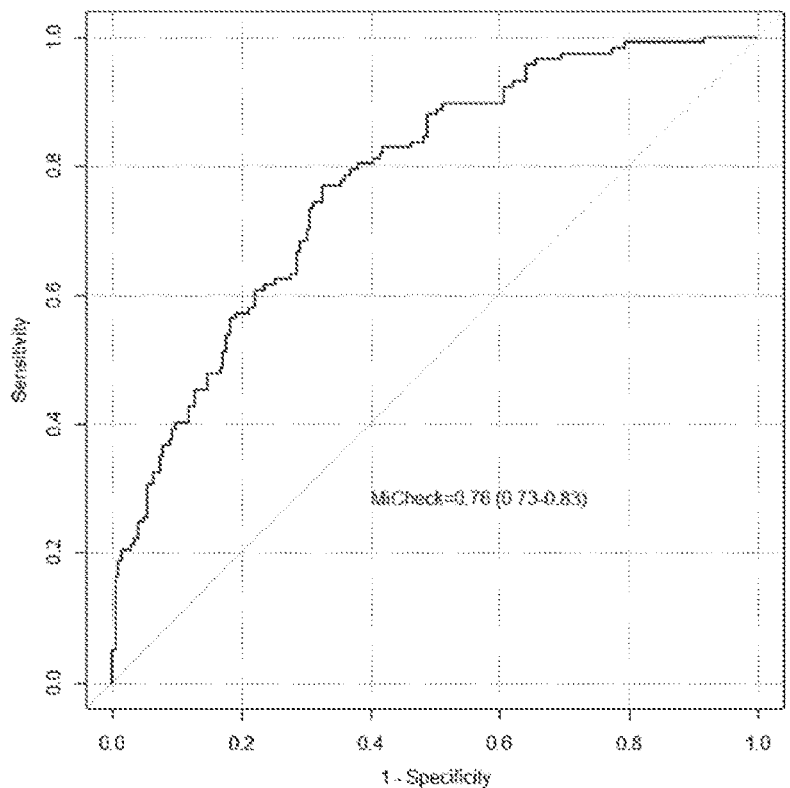
FIGURE TWENTY-ONE
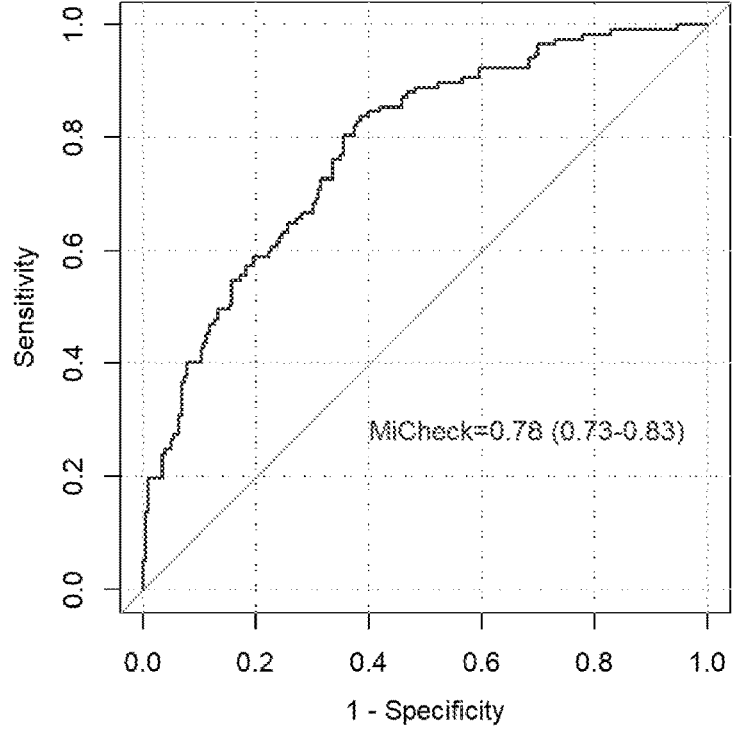
FIGURE TWENTY-TWO

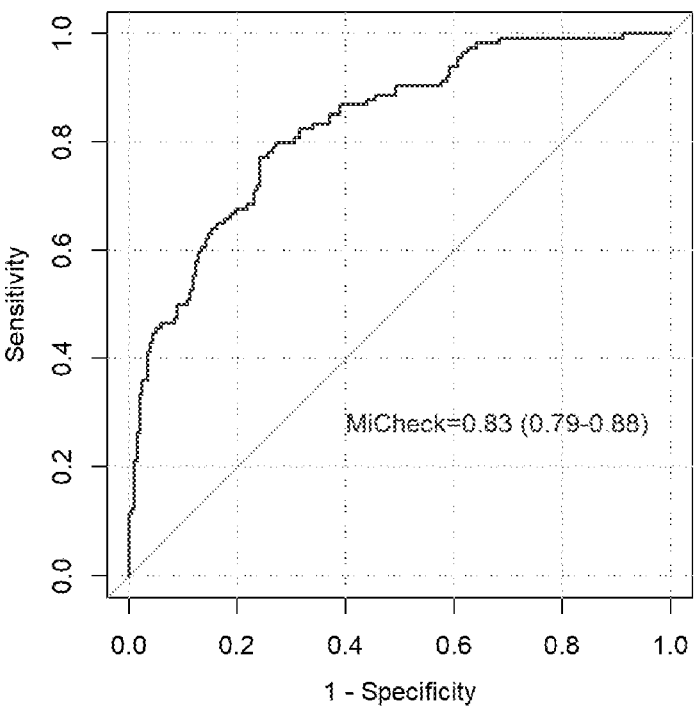
FIGURE TWENTY-THREE
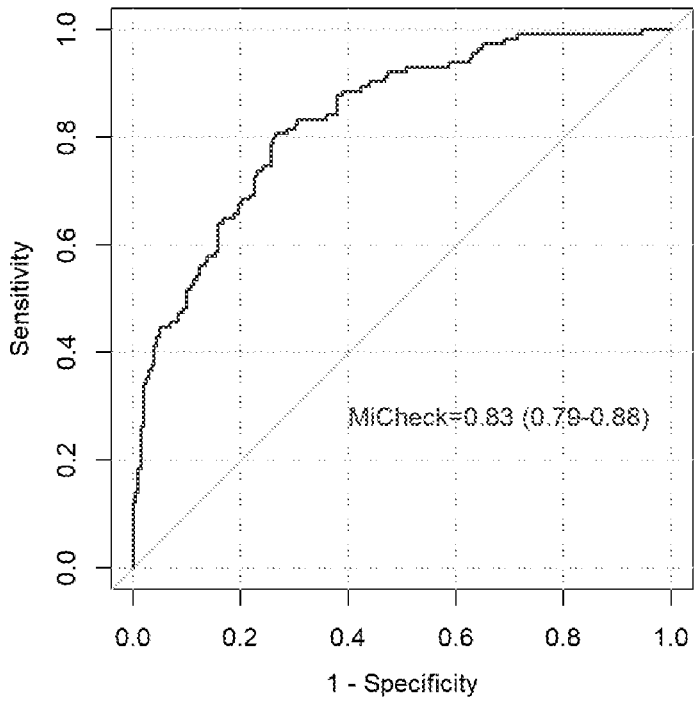
FIGURE TWENTY-FOUR

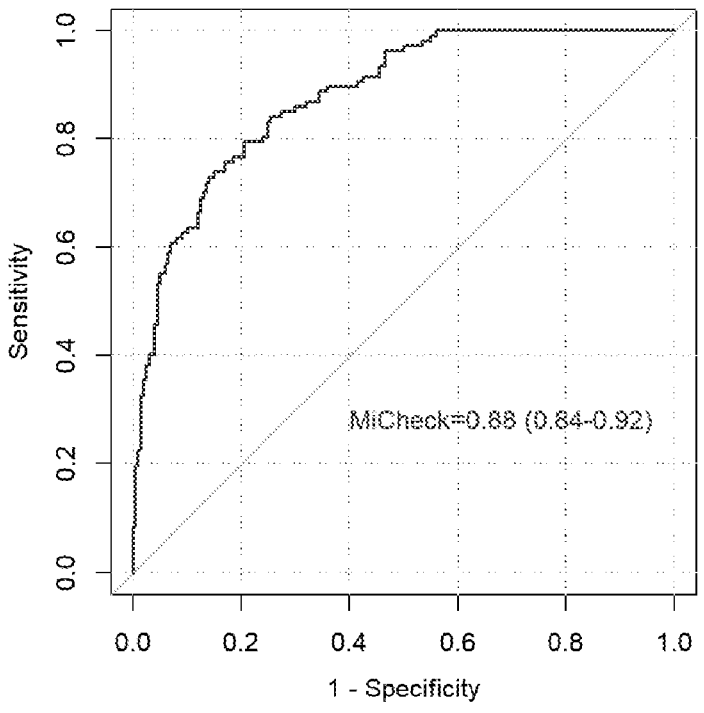
FIGURE TWENTY-FIVE
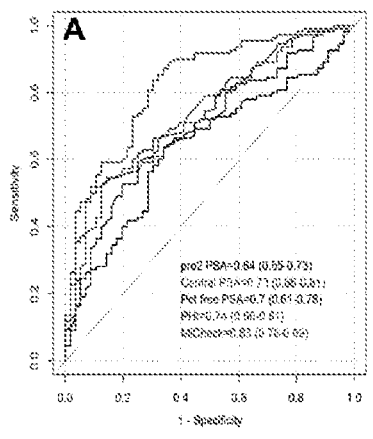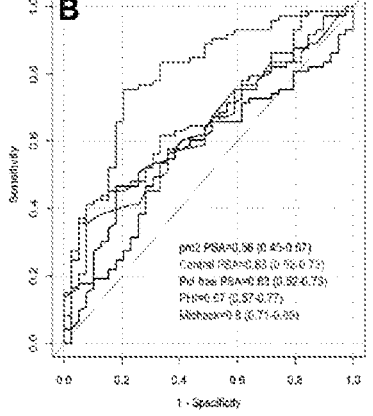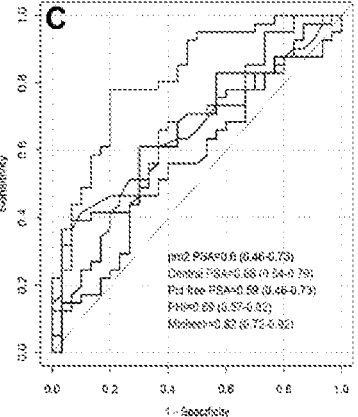
FIGURE TWENTY-SIX

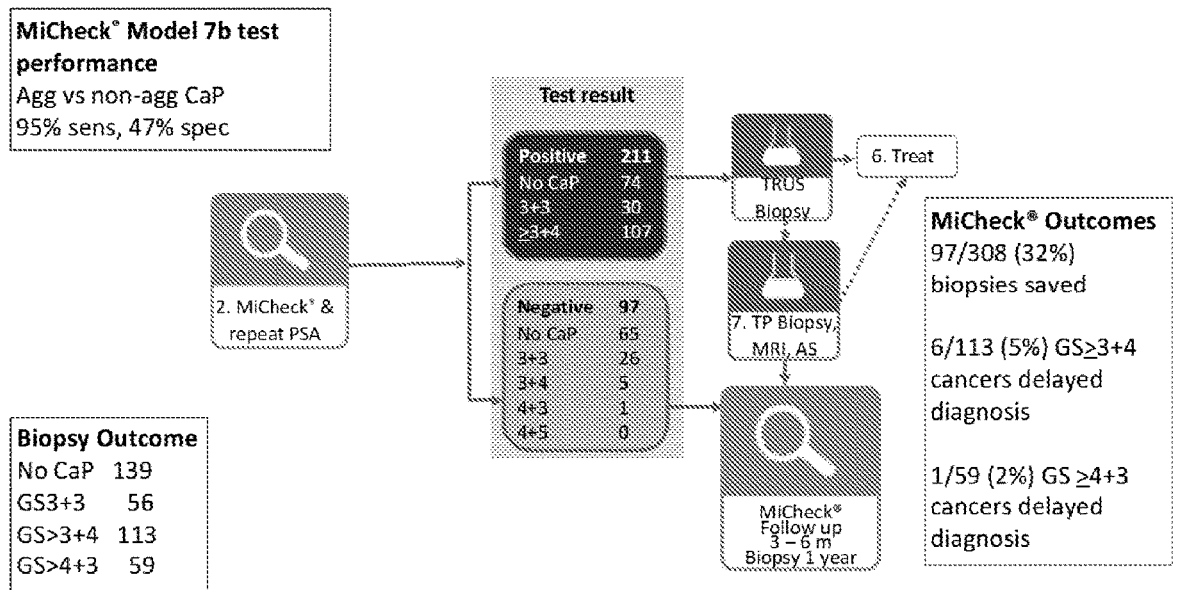
FIGURE TWENTY-SEVEN
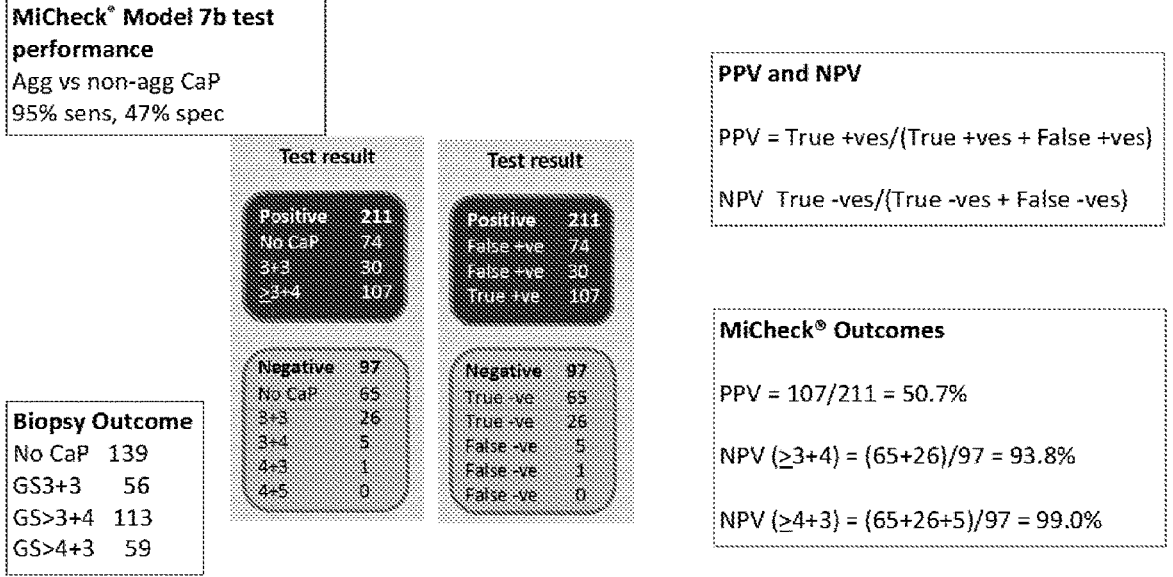
FIGURE TWENTY-EIGHT

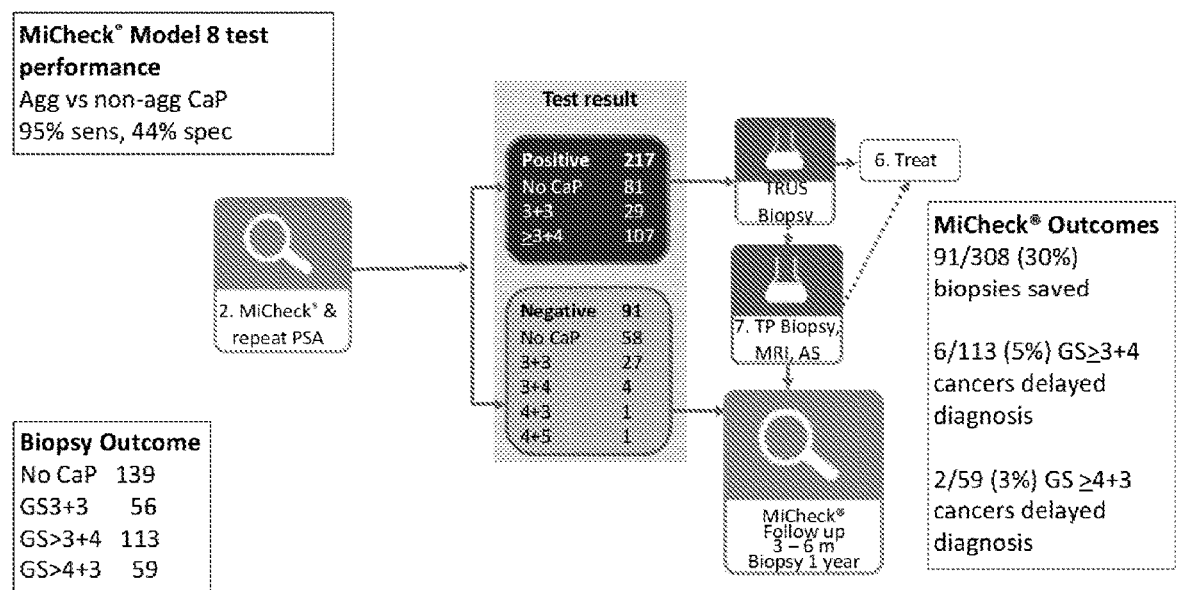
FIGURE TWENTY-NINE
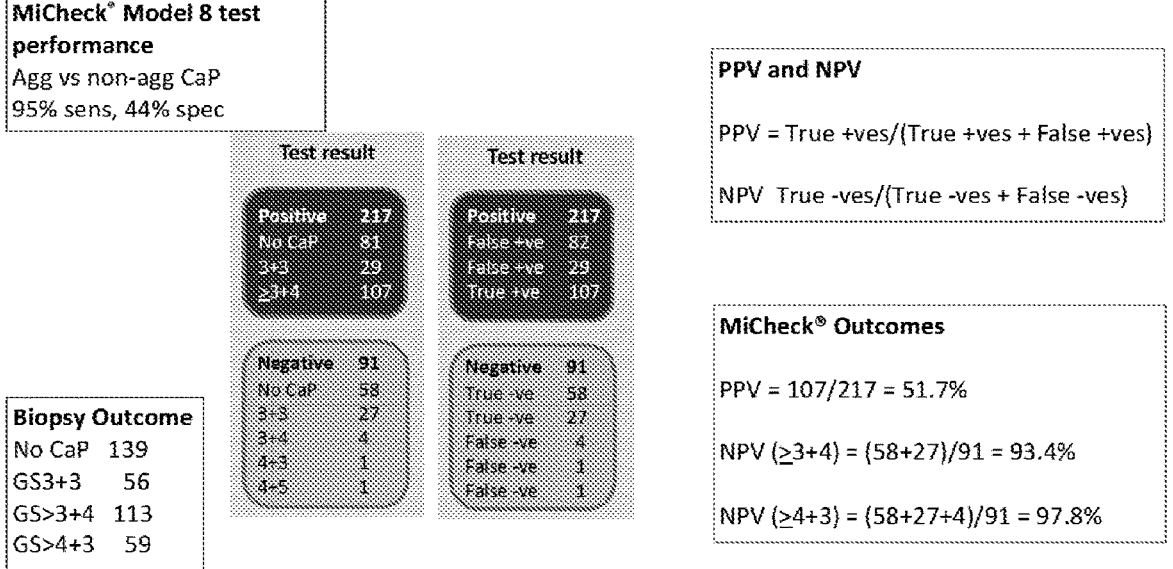
FIGURE THIRTY

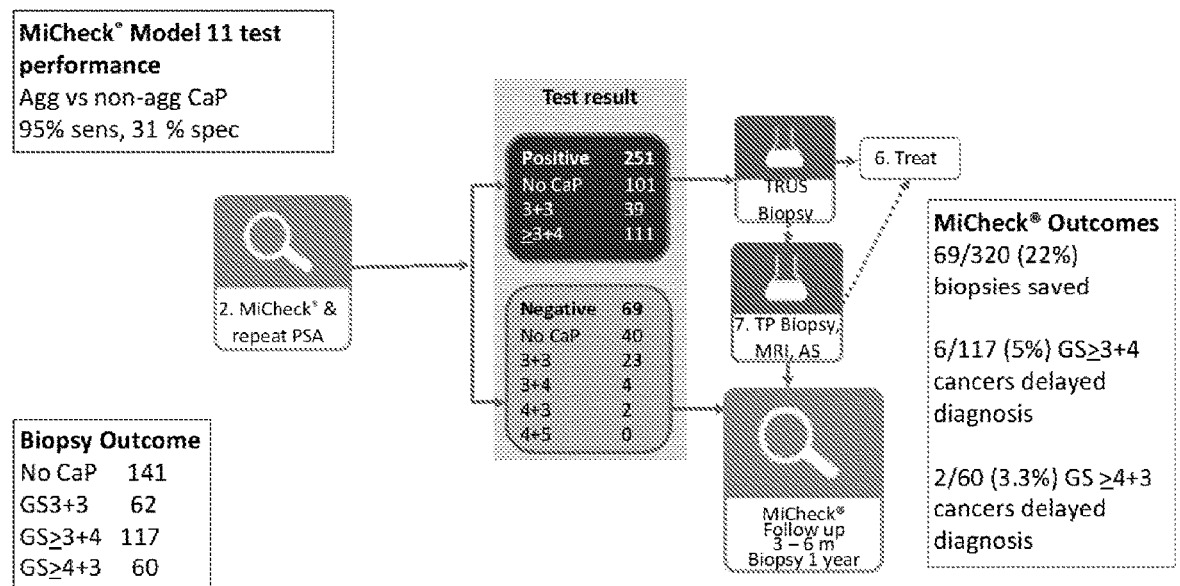
FIGURE THIRTY-ONE
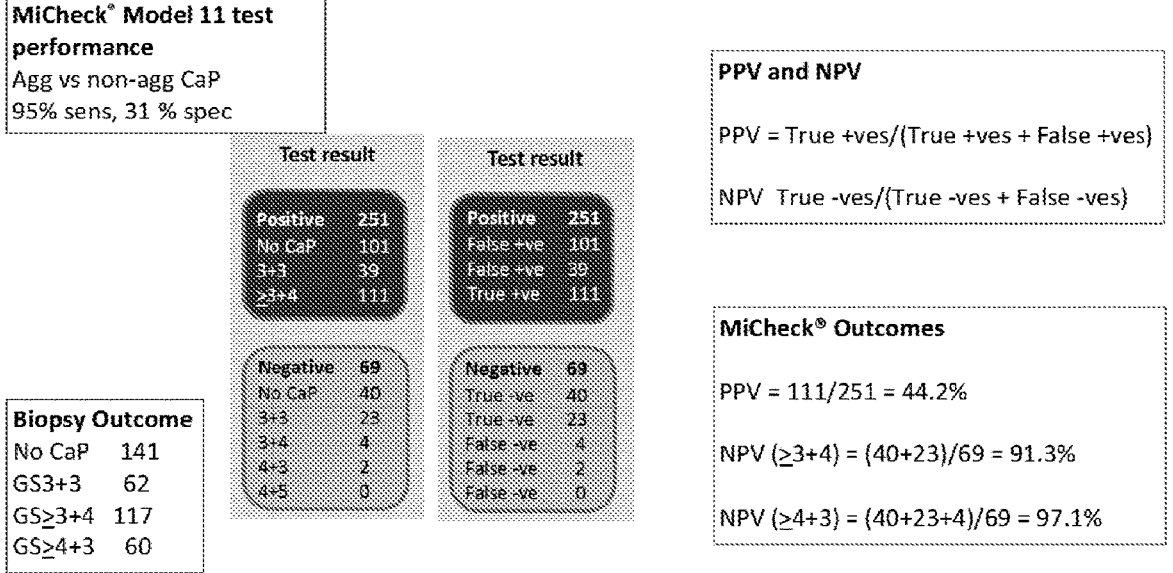
FIGURE THIRTY-TWO

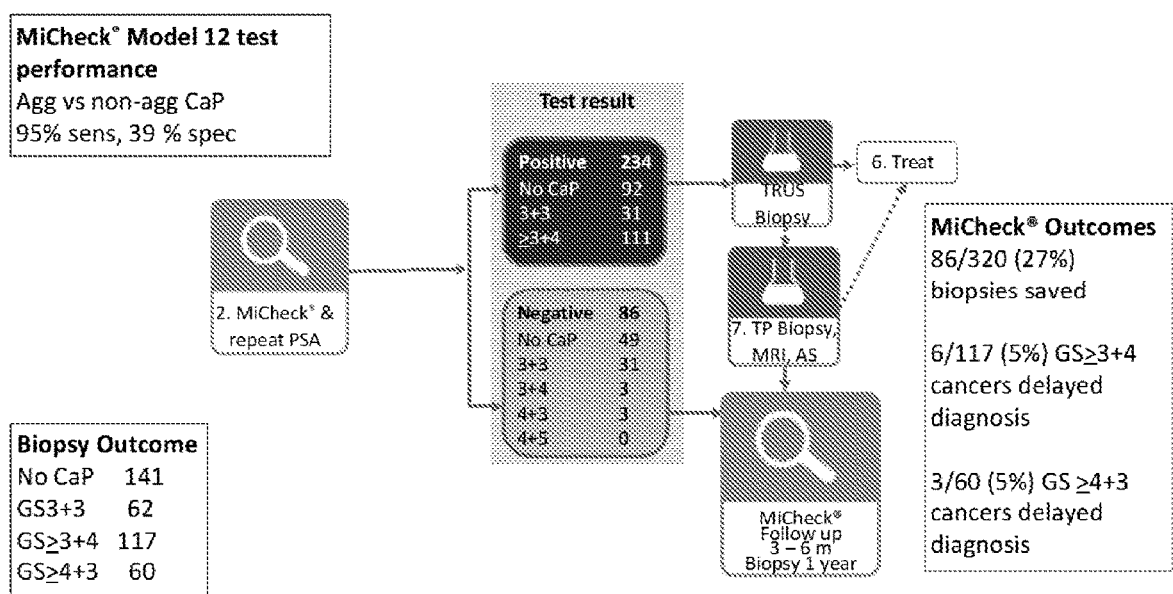
FIGURE THIRTY-THREE
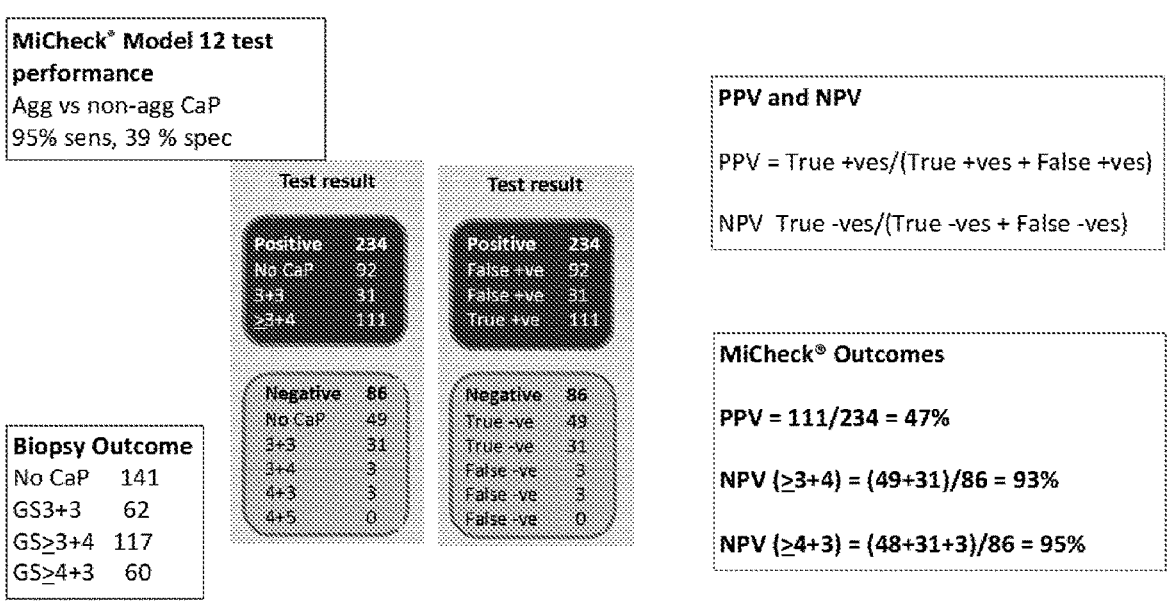
FIGURE THIRTY-FOUR

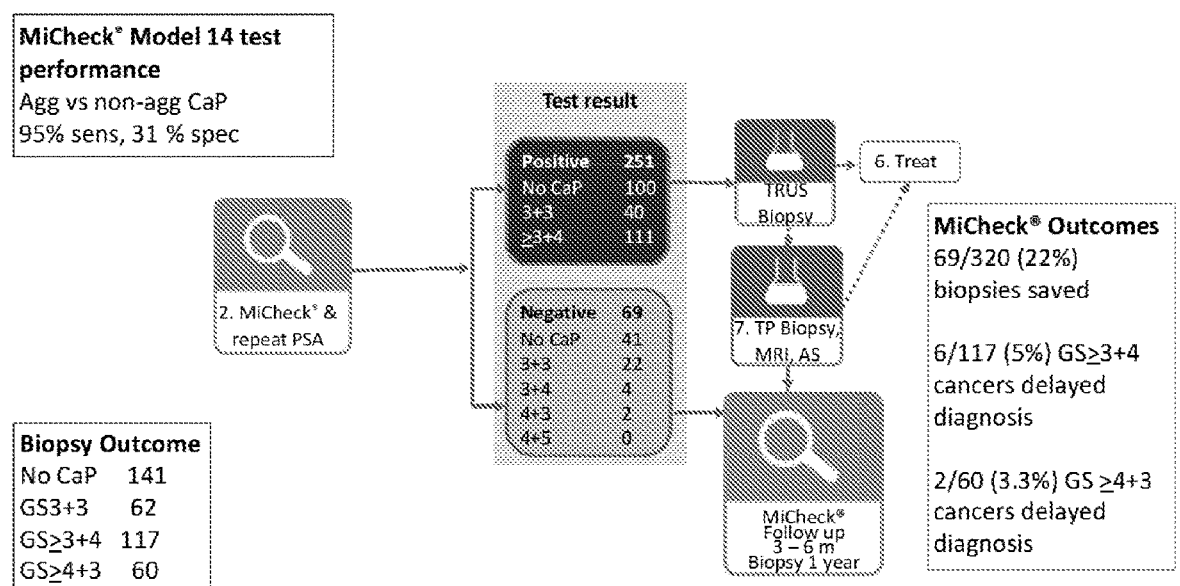
Note: This model detects 1 fewer noCaP patient in positive test and one more GS3+3 compared to Model 11
FIGURE THIRTY-FIVE
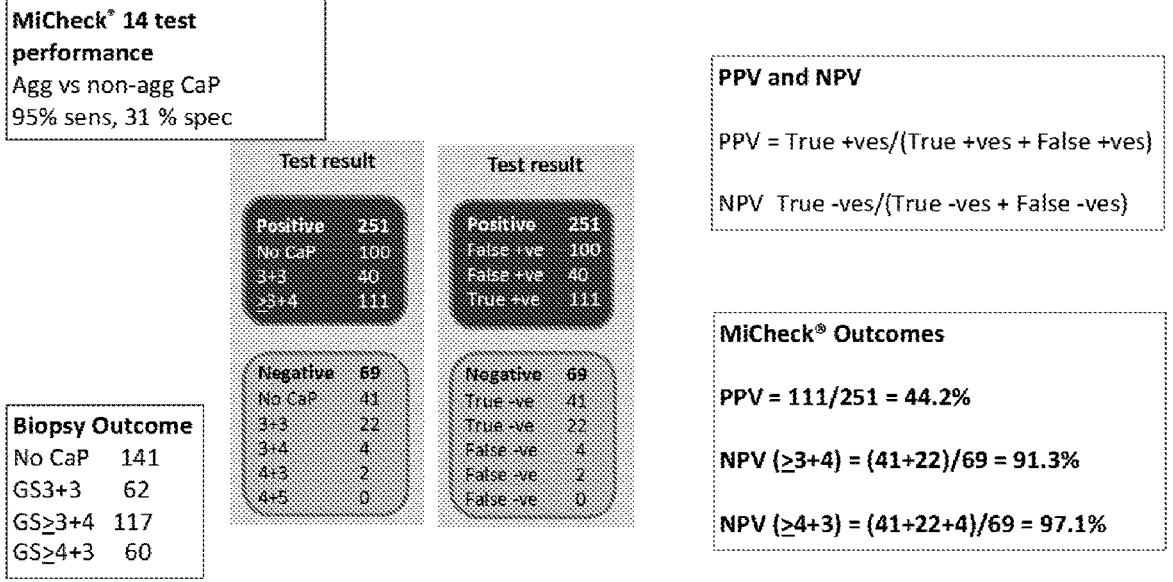
FIGURE THIRTY-SIX

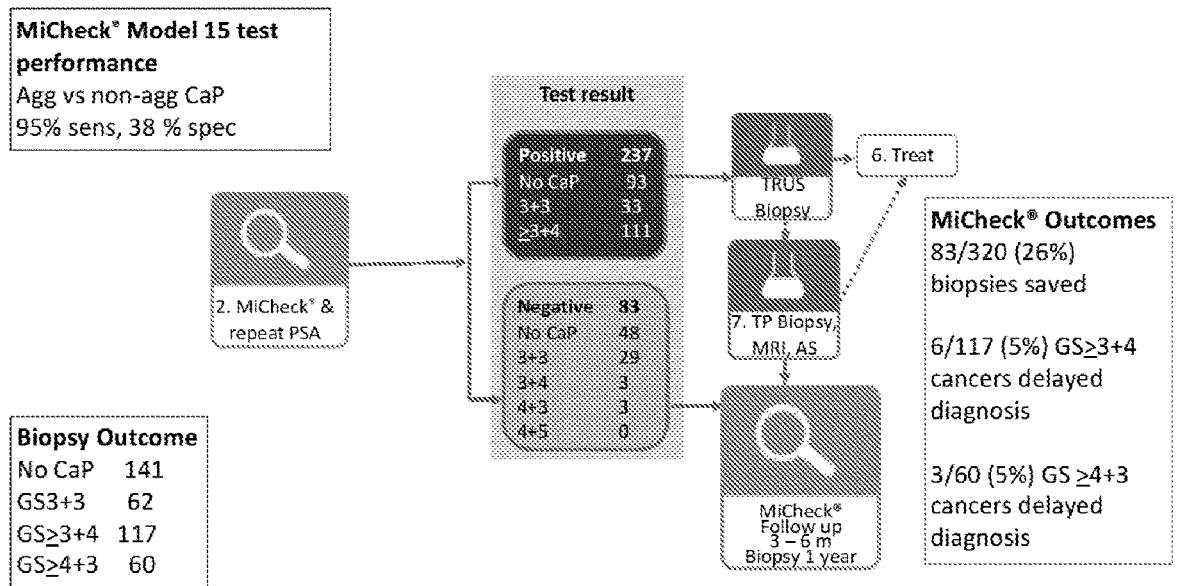
Note: This model detects 1 more noCaP patient in positive test and two more GS3+3 compared to Model 12
FIGURE THIRTY-SEVEN
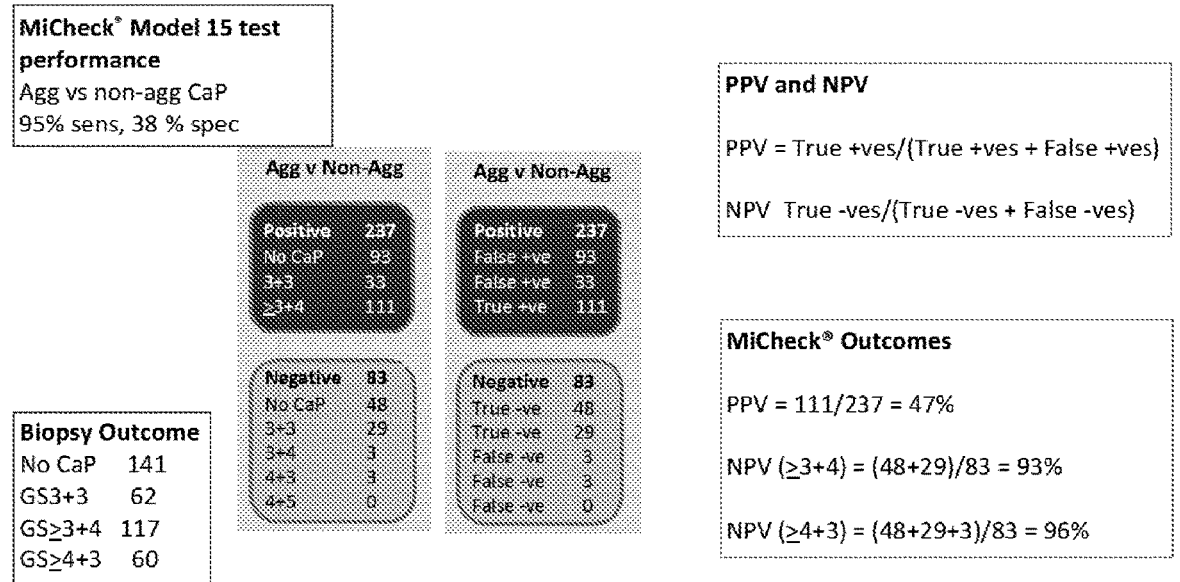
FIGURE THIRTY-EIGHT

1

BIOMARKER COMBINATIONS FOR DETERMINING AGGRESSIVE PROSTATE CANCER

INCORPORATION BY CROSS-REFERENCE

This application is a national phase application based on PCT/AU2019/051080 filed on Oct. 4, 2019, which claims priority from Australian provisional patent application numbers 2018903763 filed on Oct. 5, 2018, and 2019900406 filed on Feb. 8, 2018, the entire contents of which are incorporated herein by cross-reference.

TECHNICAL FIELD

The present invention relates generally to the fields of immunology and medicine. More specifically, the present invention relates to the diagnosis of aggressive and non-aggressive forms of prostate cancer in subjects by assessing various combinations of biomarker/s and clinical variable/s.

BACKGROUND

Prostate cancer is the most frequently diagnosed visceral cancer and the second leading cause of cancer death in males. According to the National Cancer Institute's SEER program and the Centers for Disease Control's National Center for Health Statistics, 164,690 cases of prostate cancer are estimated to have arisen in 2018 (9.5% of all new cancer cases) with an estimated 29,430 deaths (4.8% of all cancer deaths) (see SEER Cancer Statistics Factsheets: Prostate Cancer. National Cancer Institute. Bethesda, MD, http://seer.cancer.gov/statfacts/html/prost.html). The relative proportion of aggressive prostate cancers (defined as Gleason 3+4 or higher) to non-aggressive prostate cancers (defined as Gleason 3+3 or lower) differs between studies. A recent study of 1012 US men proceeding to prostate biopsy with elevated PSA demonstrated 542 men were negative for prostate cancer on biopsy, 239 had Gleason 3+3 prostate cancer and 231 had Gleason 3+4 or higher prostate cancer (Parekh et al. Eur Urol. 2015 September; 68 (3): 464-70).

Commonly used screening tests for prostate cancer include digital rectal exam (DRE) and detection of prostate specific antigen (PSA) in blood. DRE is invasive and imprecise, and the prevalence of false negative (i.e. cancer undetected) and false positive (i.e. indication of cancer where none exists) results from PSA assays is well documented. Upon a positive diagnosis with DRE or PSA screening, confirmatory diagnostic tests include transrectal ultrasound, biopsy, and transrectal magnetic resonance imaging (MRI) biopsy. These techniques are invasive and cause significant discomfort to the subject under examination.

In 2012, the United States Preventative Services Taskforce (USPTF) issued a recommendation against routine prostate cancer screening using the PSA test. This led to a decrease in the number of men proceeding to biopsy following elevated PSA test results and an increase in the proportion of men presenting with aggressive prostate cancer (Fleshner & Carlsson, Nature Reviews Urology, volume 15, pages 532-534, 2018).

A general need exists for more convenient, reliable and accurate diagnostic tests capable of discerning between aggressive and non-aggressive forms of prostate cancer and for detecting aggressive prostate cancer.

SUMMARY OF THE INVENTION

The present inventors have identified combinations of biomarker/s and clinical variable/s effective for detecting aggressive prostate cancer. Accordingly, the biomarker/clinical variable combinations disclosed herein can be used to detect the presence or absence of aggressive prostate cancer in a subject.

The present invention relates at least to the following series of numbered embodiments below:

Embodiment 1. A method for diagnosing aggressive prostate cancer (CaP) in a test subject, comprising:

(a) detecting one or more analyte/s in a biological sample from the test subject to thereby obtain an analyte level for each said analyte in the test subject's biological sample, and obtaining a measurement of two or more clinical variables from the test subject; and (b) applying a suitable algorithm and/or transformation to a combination of the clinical variable measurements and analyte level/s of the test subject to thereby generate a test subject score value for comparison to a threshold value; and (c) determining whether the test subject has aggressive CaP by comparison of the subject test score value and the threshold value, wherein:

the one or more analyte/s comprise or consist of leptin, the two or more clinical variables comprise at least two of: total PSA, DRE, subject age, prostate volume, and the threshold value is determined by:

detecting said one or more analyte/s in a series of biological samples obtained from a population of subjects having aggressive CaP and from a population of control subjects not having aggressive CaP, to thereby obtain an analyte level for each said analyte in each said biological sample of the series;

combining each said analyte level of the series with measurements of said two or more clinical variables obtained from each said subject of the populations, in a manner that allows discrimination between aggressive CaP and an absence of aggressive CaP, to thereby generate the threshold value.

Embodiment 2. The method of embodiment 1, wherein the population of control subjects comprises subjects that do not have prostate cancer and subjects that have non-aggressive prostate cancer.

Embodiment 3. A method for discerning whether a test subject has non-aggressive or aggressive prostate cancer (CaP), comprising:

(a) detecting one or more analyte/s in a biological sample from the test subject to thereby obtain an analyte level for each said analyte in the test subject's biological sample, and obtaining a measurement of two or more clinical variable/s from the test subject; and (b) applying a suitable algorithm and/or transformation to a combination of the clinical variable measurements and analyte level/s to thereby generate a test subject score value for comparison to a threshold value; and (c) determining whether the test subject has non-aggressive or aggressive CaP by comparison of the subject test score value and the threshold value, wherein the test subject has previously been determined to have prostate cancer or a likelihood of having prostate cancer (e.g. by any one or more of a PSA-based test, digital rectal examination (DRE), family history, an ultrasound-based test, magnetic resonance imaging (MRI), a urine biomarker test, an exosome-based test), the one or more analyte/s comprise or consist of leptin, the two or more clinical variables comprise at least two of: total PSA, DRE, subject age, prostate volume, and the threshold value is determined by:

detecting said one or more analyte/s in a series of biological samples obtained from a population of subjects having aggressive CaP and from a population of control subjects having non-aggressive CaP, to thereby obtain an analyte level for each said analyte in each said biological sample of the series;

combining each said analyte level of the series with measurements of said two or more clinical variables obtained from each said subject of the populations, in a manner that allows discrimination between aggressive CaP and non-aggressive CaP, to thereby generate the threshold value.

Embodiment 4. The method of embodiment 1 or embodiment 3, wherein the population of control subjects has non-aggressive CaP as defined by a Gleason score of 3+3.

Embodiment 5. The method of any one of embodiments 1 to 3, wherein the threshold value is determined prior to performing the method.

Embodiment 6. The method of any one of embodiments 1 to 5, wherein the two or more clinical variables and the one or more analyte/s comprise any one of the following:

total PSA, prostate volume, leptin, subject age, IL-7 and VEGF;

total PSA, prostate volume, leptin, subject age, IL-7, VEGF, osteopontin and CD40L;

total PSA, % free PSA, prostate volume, leptin, osteopontin and HE4.WFDC2;

total PSA, DRE, leptin, subject age, VEGF and IL-7;

total PSA, DRE, leptin, subject age, VEGF, osteopontin;

total PSA, DRE, leptin, subject age, VEGF, IL-7, GPC-1;

total PSA, DRE, leptin, subject age, VEGF, osteopontin, GPC-1;

total PSA, DRE, leptin, subject age, VEGF, IL-7, GPC-1, % free PSA;

total PSA, DRE, leptin, subject age, VEGF, osteopontin, GPC-1, % free PSA;

total PSA, DRE, leptin, subject age, prior negative biopsy, VEGF-C, osteopontin, GPC-1, CD40L, proPSA, % free PSA.

Embodiment 7. The method of any one of embodiments 1 to 6, comprising selecting a subset of the combined analyte/s and/or clinical variable measurements to generate the threshold value.

Embodiment 8. The method of any one of embodiments 1 to 7, wherein said combining of each said analyte level of the series with said measurements of the two or more clinical variables comprises combining a logistic regression score of the clinical variable measurements and analyte level/s in a manner that maximizes said discrimination, in accordance with the formula:

$$Logit\ (P) = \text{Log}\left(P/1 - P\right) = \text{intercept} +$$

$$\sum\nolimits_{i=1}^{N} \left(\text{coefficient}_i \times \text{transformed (variable}_i) P = \frac{\exp(Logit(P))}{1 + \exp(Logit(P))}\right.$$

wherein:

P is probability that the test subject has aggressive prostate cancer, the coefficient$_i$ is the natural log of the odds ratio of the variable, the transformed variable; is the natural log of the variable; value, excluding a variable age;

or in accordance with the formula:

$$Logit\ (P) =$$

$$\text{Log}\left(P/1 - P\right) = \text{intercept} + \sum\nolimits_{i=1}^{N} \left(\text{coefficient}_i \times \text{transformed (variable}_i) +\right.$$

$$\text{coefficient}_{Age} \times \text{Age}\ P = \frac{\exp(Logit(P))}{1 + \exp(Logit(P))}$$

wherein:

P is probability that the test subject has aggressive prostate cancer, the coefficient$_i$ is the natural log of the odds ratio of the variable, the transformed variable; is the natural log of the variable; value.

or in accordance with the formula:

$$Logit\ (P) = \text{Log}\left(P/1 - P\right) = \text{intercept} + \sum\nolimits_{i=1}^{N}$$

$$\left(\text{coefficient}_i \times (\text{variable}_i) + \text{coefficient}_{Age} \times \text{Age}\ P = \frac{\exp(Logit(P))}{1 + \exp(Logit(P))}\right.$$

wherein:

P is probability that the test subject has aggressive prostate cancer, and the coefficient$_i$ is the natural log of the odds ratio of the variable.

Embodiment 9. The method of any one of embodiments 1 to 8, wherein said applying a suitable algorithm and/or transformation to the combination of the clinical variable measurements and analyte level/s comprises use of an exponential function, a logarithmic function, a power function and/or a root function.

Embodiment 10. The method according to any one of embodiments 1 to 9, wherein the suitable algorithm and/or transformation applied to the combination of the clinical variable measurements and analyte level/s of the test subject is in accordance with the formula:

$$Logit\ (P) = \text{Log}\left(P/1 - P\right) = \text{intercept} +$$

$$\sum\nolimits_{i=1}^{N} \left(\text{coefficient}_i \times \text{transformed (variable}_i)\ P = \frac{\exp(Logit(P))}{1 + \exp(Logit(P))}\right.$$

wherein:

P is probability of that the test subject has aggressive prostate cancer, the coefficient$_i$ is the natural log of the odds ratio of the variable, the transformed variable; is the natural log of the variable$_i$ value, excluding a variable age;

or in accordance with the formula:

$$Logit\ (P) =$$

$$\text{Log}\left(P/1 - P\right) = \text{intercept} + \sum\nolimits_{i=1}^{N} \left(\text{coefficient}_i \times \text{transformed (variable}_i) +\right.$$

$$\text{coefficient}_{Age} \times \text{Age}\ P = \frac{\exp(Logit(P))}{1 + \exp(Logit(P))}$$

wherein:

P is probability of that the test subject has aggressive prostate cancer, the coefficient$_i$ is the natural log of the odds ratio of the variable, the transformed variable$_i$ is the natural log of the variable; value;

or in accordance with the formula:

$$Logit\ (P) = \text{Log}(P/1 - P) = \text{intercept} + \sum_{i=1}^{N}$$

$$\left(\text{coefficient}_i \times (\text{variable}_i) + \text{coefficient}_{Age} \times \text{Age}\ P = \frac{\exp(Logit(P))}{1 + \exp(Logit(P))}\right.$$

wherein:

P is probability that the test subject has aggressive prostate cancer, the coefficient$_i$ is the natural log of the odds ratio of the variable;

and said suitable algorithm and/or transformation is used to generate the subject test score that is compared to the threshold value to thereby determine whether or not the test subject has aggressive prostate cancer.

Embodiment 11. The method according to any one of embodiments 1 to 10, wherein said combining of each said analyte level of the series with measurements of said two or more clinical variables obtained from each said subject of the populations maximizes said discrimination.

Embodiment 12. The method of any one of embodiments 1 to 11, wherein said combining of each said analyte level of the series with the measurements of two or more clinical variables obtained from each said subject of the populations is conducted in a manner that:

(i) reduces the misclassification rate between the subjects having aggressive CaP and said control subjects; and/or (ii) increases sensitivity in discriminating between the subjects having aggressive CaP and said control subjects; and/or (iii) increases specificity in discriminating between the subjects having aggressive CaP and said control subjects.

Embodiment 13. The method of embodiment 12, wherein said combining in a manner that reduces the misclassification rate between the subjects having aggressive CaP and said control subjects comprises selecting a suitable true positive and/or true negative rate.

Embodiment 14. The method of embodiment 12, wherein said combining in a manner that reduces the misclassification rate between the subjects having aggressive CaP and said control subjects minimizes the misclassification rate.

Embodiment 15. The method of embodiment 12, wherein said combining in a manner that reduces the misclassification rate between the subjects having aggressive CaP and said control subjects comprises minimizing the misclassification rate between the subjects having aggressive CaP and said control subjects by identifying a point where the true positive rate intersects the true negative rate.

Embodiment 16. The method embodiment 12, wherein said selecting the threshold value from the combined clinical variable measurement/s and combined analyte level/s in a manner that increases sensitivity in discriminating between the subjects having aggressive CaP and said control subjects increases or maximizes said sensitivity.

Embodiment 17. The method embodiment 12, wherein said selecting the threshold value from the combined clinical variable measurement/s and combined analyte level/s in a manner that increases specificity in discriminating between the subjects having aggressive CaP and said control subjects increases or maximizes said specificity.

Embodiment 18. The method according to any one of embodiments 1 to 17, wherein the two or more clinical variables and the one or more analytes consist of any one of the following:

total PSA, prostate volume, leptin, subject age, IL-7 and VEGF;

total PSA, prostate volume, leptin, subject age, IL-7, VEGF, osteopontin and CD40L;

total PSA, % free PSA, prostate volume, leptin, osteopontin and HE4.WFDC2;

total PSA, DRE, leptin, subject age, VEGF and IL-7;

total PSA, DRE, leptin, subject age, VEGF, osteopontin;

total PSA, DRE, leptin, subject age, VEGF, IL-7, GPC-1;

total PSA, DRE, leptin, subject age, VEGF, osteopontin, GPC-1;

total PSA, DRE, leptin, subject age, VEGF, IL-7, GPC-1, % free PSA;

total PSA, DRE, leptin, subject age, VEGF, osteopontin, GPC-1, % free PSA;

total PSA, DRE, leptin, subject age, prior negative biopsy, VEGF-C, osteopontin, GPC-1, CD40L, proPSA, % free PSA.

Embodiment 19. The method according to any one of embodiments 1 to 18, wherein the test subject has previously received a positive indication of aggressive prostate cancer.

Embodiment 20. The method according to any one of embodiments 1 to 19, wherein the test subject has previously received a positive indication of aggressive prostate cancer by digital rectal exam (DRE) and/or by PSA testing.

Embodiment 21. The method according to any one of embodiments 1 to 20, wherein said detecting of one or more analyte/s in the biological sample from the test subject comprises:

(i) measuring one or more fluorescent signals indicative of each said analyte level;

(ii) obtaining a measurement of weight/volume of said analyte/s in the biological sample;

(iii) measuring an absorbance signal indicative of each said analyte level; or (iv) using a technique selected from the group consisting of mass spectrometry, a protein array technique, high performance liquid chromatography (HPLC), gel electrophoresis, radiolabeling, and any combination thereof.

Embodiment 22. The method according to any one of embodiments 1 to 21, wherein each said sample is contacted with first and second antibody populations for detection of each said analyte, wherein each said antibody population has binding specificity for one of said analytes, and the first and second antibody populations have different analyte binding specificities.

Embodiment 23. The method according to embodiment 22, wherein the first and/or second antibody populations are labelled.

Embodiment 24. The method according to embodiment 23, wherein the first and/or second antibody populations comprise a label selected from the group consisting of a radiolabel, a fluorescent label, a biotin-avidin amplification system, a chemiluminescence system, microspheres, and colloidal gold.

Embodiment 25. The method according to any one of embodiments 20 to 24, wherein binding of each said antibody population to the analyte is detected by a technique selected from the group consisting of: immunofluorescence, radiolabeling, immunoblotting, Western blotting, enzyme-linked immunosorbent assay (ELISA), flow cytometry, immunoprecipitation, immunohistochemistry, biofilm test, affinity ring test, antibody array optical density test, and chemiluminescence.

Embodiment 26. The method according to any one of embodiments 1 to 25, wherein the series of biological samples obtained from each said population and the test subject's biological sample are each whole blood, serum, plasma, saliva, tear/s, urine, or tissue.

Embodiment 27. The method according to any one of embodiments 1 to 26, wherein said test subject, said population of subjects having aggressive CaP, and said population of control subjects are human.

Embodiment 28. The method of any one of embodiments 1 to 27, wherein said detecting of each said analyte in the biological sample from the test subject or the series of biological samples obtained from each said population comprises detecting the analytes directly.

Embodiment 29. The method of any one of embodiments 1 to 28, wherein said detecting of each said analyte in the biological sample from the test subject or the series of biological samples obtained from each said population comprises detecting a nucleic acid encoding the analytes.

BRIEF DESCRIPTION OF THE FIGURES

Preferred embodiments of the present invention will now be described, by way of example only, with reference to the accompanying figures wherein:

FIG. One is a flow diagram showing the stages of a typical clinical diagnostic pathway for aggressive prostate cancer.

FIG. Two shows an exemplary strategy for implementation of the diagnostic methods of the present invention.

FIG. Three is a graph showing the correlation between PSA concentration (ng/ml) obtained from the medical records of patients and the trial sample PSA measured centrally.

FIG. Four is a comparison of the central biopsy results and the biopsy result obtained at the local site.

FIG. Five depicts a ROC curve analysis based on PSA levels (model fitting: logistic regression) generated under Model 1 [aggressive prostate cancer (AgCaP) versus non-aggressive prostate cancer (NoAgCaP)].

FIG. Six depicts a ROC curve analysis based on prostate volume (PV) (model fitting: logistic regression) generated under Model 2 (AgCaP versus NoAgCaP).

FIG. Seven depicts a ROC curve analysis based on leptin (model fitting: logistic regression) generated under Model 3 (AgCaP versus NoAgCaP).

FIG. Eight depicts a ROC curve analysis based on % free PSA (model fitting: logistic regression) generated under Model 4 (AgCaP versus NoAgCaP).

FIG. Nine depicts a ROC curve analysis based on PHI (model fitting: logistic regression) generated under Model 5 (AgCaP versus NoAgCaP).

FIG. Ten depicts a ROC curve analysis based on PSA, PV and leptin (model fitting: logistic regression) generated under Model 6 (AgCaP versus NoAgCaP).

FIG. Eleven depicts a ROC curve analysis based on PSA, PV, Leptin, Age, IL-7 and VEGF (model fitting: multiple logistic regression) generated under Model 7a (AgCaP versus NoAgCaP).

FIG. Twelve depicts a ROC curve analysis based on PSA, PV, Leptin, Age, IL-7 and VEGF (model fitting: multiple logistic regression) generated under Model 7b (AgCaP versus NoAgCaP).

FIG. Thirteen depicts a ROC curve analysis based on PSA, PV, leptin, Age, VEGF, IL-7, Osteopontin, and CD40L (model fitting: multiple logistic regression) generated under Model 8 (AgCaP versus NoAgCaP).

FIG. Fourteen depicts a ROC curve analysis based on PSA, % Free PSA, PV, Leptin, osteopontin and HE4.WFDC2 (model fitting: logistic regression) generated under Model 9 (AgCaP versus NoAgCaP).

FIG. Fifteen depicts a ROC curve analysis based on DRE (model fitting: logistic regression) generated under Model 10 (AgCaP versus NoAgCaP).

FIG. Sixteen depicts a ROC curve analysis based on PSA, DRE, Leptin, Age, VEGF and IL-7 (model fitting: logistic regression) generated under Model 11 (AgCaP versus NoAgCaP).

FIG. Seventeen depicts a ROC curve analysis based on PSA, DRE, Leptin, Age, VEGF and Osteopontin (model fitting: logistic regression) generated under Model 12 (AgCaP versus NoAgCaP).

FIG. Eighteen depicts a ROC curve analysis based on GPC-1 (model fitting: logistic regression) generated under Model 13 (AgCaP versus NoAgCaP).

FIG. Nineteen depicts a ROC curve analysis based on PSA, DRE, Leptin, Age, VEGF, IL-7 and GPC-1 (model fitting: logistic regression) generated under Model 14 (AgCaP versus NoAgCaP).

FIG. Twenty depicts a ROC curve analysis based on PSA, DRE, Leptin, Age, VEGF, Osteopontin and GPC-1 (model fitting: logistic regression) generated under Model 15 (AgCaP versus NoAgCaP).

FIG. Twenty-One depicts a ROC curve analysis based on PSA, DRE, Leptin, Age, VEGF, IL-7 and GPC-1 (model fitting: logistic regression) generated under Model 14b (AgCaP versus NOT-AgCaP).

FIG. Twenty-Two depicts a ROC curve analysis based on PSA, DRE, Leptin, Age, VEGF, Osteopontin and GPC-1 (model fitting: logistic regression) generated under Model 15b (AgCaP versus NOT-AgCaP).

FIG. Twenty-Three depicts a ROC curve analysis based on PSA, DRE, Leptin, Age, VEGF, IL-7, GPC-1 and % free PSA (model fitting: logistic regression) generated under Model 16 (AgCaP versus NOT-AgCaP).

FIG. Twenty-Four depicts a ROC curve analysis based on PSA, DRE, Leptin, Age, VEGF, Osteopontin, GPC-1 and % free PSA (model fitting: logistic regression) generated under Model 17 (AgCaP versus NOT-AgCaP).

FIG. Twenty-Five depicts a ROC curve analysis based on PSA, DRE, Leptin, Age, CD-40L, VEGF-C, Osteopontin, GPC-1, % free PSA, prior negative biopsy and proPSA (model fitting: logistic regression) generated under Model 18 (AgCaP versus NOT-AgCaP).

FIG. Twenty-Six depicts a comparison of ROC curves for MiCheck® model 7b, PSA, pro2PSA, % free PSA and PHI in either (A) all PSA ranges (B) PSA range 4-10 ng/ml or (C) PSA 4-10 ng/ml, Age>50 and normal DRE status FIG. Twenty-Seven shows the frequency distribution of no cancer, non-aggressive cancer and aggressive prostate cancers from the test population, together with the classifications of the Model 7b.

FIG. Twenty-Eight shows the breakdown between true and false positives and true and false negatives in the patients of Twenty-Seven, together with the positive and negative predictive values of Model 7b.

FIG. Twenty-Nine shows the frequency distribution of no cancer, non-aggressive cancer and aggressive prostate cancers from the test population, together with the classifications of Model 8.

FIG. Thirty shows the breakdown between true and false positives and true and false negatives in the patients of FIG. Twenty-Nine, together with the positive and negative predictive values of Model 8.

FIG. Thirty-One shows the frequency distribution of no cancer, non-aggressive cancer and aggressive prostate cancers from the test population, together with the classifications of Model 11.

FIG. Thirty-Two shows the breakdown between true and false positives and true and false negatives in the patients of FIG. Thirty-One, together with the positive and negative predictive values of Model 11.

FIG. Thirty-Three shows the frequency distribution of no cancer, non-aggressive cancer and aggressive prostate cancers from the test population, together with the classifications of Model 12.

FIG. Thirty-Four shows the breakdown between true and false positives and true and false negatives in the patients of FIG. Thirty-Three, together with the positive and negative predictive values of Model 12.

FIG. Thirty-Five shows the frequency distribution of no cancer, non-aggressive cancer and aggressive prostate cancers from the test population, together with the classifications of Model 14.

FIG. Thirty-Six shows the breakdown between true and false positives and true and false negatives in the patients of Thirty-Five, together with the positive and negative predictive values of Model 14.

FIG. Thirty-Seven shows the frequency distribution of no cancer, non-aggressive cancer and aggressive prostate cancers from the test population, together with the classifications of Model 15.

FIG. Thirty-Eight shows the breakdown between true and false positives and true and false negatives in the patients of FIG. Thirty-Seven, together with the positive and negative predictive values of Model 15.

Definitions

As used in this application, the singular form "a", "an" and "the" include plural references unless the context clearly dictates otherwise. For example, the phrase "an antibody" also includes multiple antibodies.

As used herein, the term "comprising" means "including." Variations of the word "comprising", such as "comprise" and "comprises," have correspondingly varied meanings. Thus, for example, a biomarker/clinical variable combination "comprising" analyte A and clinical variable A may consist exclusively of analyte A and clinical variable A, or may include one or more additional components (e.g. analyte B and/or clinical variable B).

As used herein, the terms "aggressive prostate cancer" and "aggressive CaP" refer to prostate cancer with a primary Gleason score of 3 or greater and a secondary Gleason score of 4 or greater (GS≥3+4).

As used herein, the terms "non-aggressive prostate cancer" and "non-aggressive CaP" refer to prostate cancer with a primary Gleason score of less than or equal to 3 and a secondary Gleason score of less than 4 (GS≤3+3). Primary Gleason scores of less than 3 were not reported in the subject sample set described in this application hence the term GS3+3 is also used for non-aggressive prostate cancer.

As used herein, the term "clinical variable" encompasses any factor, measurement, physical characteristic relevant in assessing prostate disease, including but not limited to: Age, prostate volume, PSA level, free PSA, total PSA, % free PSA, [−2] ProPSA, PSA velocity, PSA density, Prostate Health Index, digital rectal examination (DRE), ethnic background, family history of prostate cancer, a prior negative biopsy for prostate cancer.

As used herein, the term "total PSA" refers to a test capable of measuring free plus complexed PSA in a sample.

As used herein, the term "% free PSA" refers to the ratio of free/total PSA in a sample expressed as a percentage.

As used herein, the term "proPSA" refers to a test capable of measuring the [−2] proPSA protein in a sample.

As used herein, the term PHI refers to the Prostate Health Index value, which is a number calculated by measuring total PSA, free PSA (fPSA) and [−2] proPSA using, for example, the Beckman Coulter Access 2 analyzer and associated Hybritech assays. PHI is calculated using the formula [−2] proPSA/fPSA×√PSA.

As used herein the term "VEGF" will be understood to include its alternative designation VEGFA.

As used herein, the terms "biological sample" and "sample" encompass any body fluid or tissue taken from a subject including, but not limited to, a saliva sample, a tear sample, a blood sample, a serum sample, a plasma sample, a urine sample, or sub-fractions thereof.

As used herein, the terms "diagnosing" and "diagnosis" refer to methods by which a person of ordinary skill in the art can estimate and even determine whether or not a subject is suffering from a given disease or condition. A diagnosis may be made, for example, on the basis of one or more diagnostic indicators, such as for example, the detection of a combination of biomarker/s and clinical feature/s as described herein, the levels of which are indicative of the presence, severity, or absence of the condition. As such, the terms "diagnosing" and "diagnosis" thus also include identifying a risk of developing aggressive prostate cancer.

As used herein, the terms "subject" and "patient" are used interchangeably unless otherwise indicated, and encompass any animal of economic, social or research importance including bovine, equine, ovine, primate, avian and rodent species. Hence, a "subject" may be a mammal such as, for example, a human or a non-human mammal. As used herein, the term "isolated" in reference to a biological molecule (e.g. an antibody) is a biological molecule that is free from at least some of the components with which it naturally occurs.

As used herein, the terms "antibody" and "antibodies" include, IgG (including IgG1, IgG2, IgG3, and IgG4), IgA (including IgAQ1 and IgA2), IgD, IgE, IgM, and IgY, whole antibodies, including single-chain whole antibodies, and antigen-binding fragments thereof. Antigen-binding antibody fragments include, but are not limited to, Fv, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin or appropriate production host. Antigen-binding antibody fragments, including single-chain antibodies, may comprise the variable region/s alone or in combination with the entire or partial of the following: hinge region, CH1, CH2, and CH3 domains. Also included are any combinations of variable region/s and hinge region, CH1, CH2, and CH3 domains. Antibodies may be monoclonal, polyclonal, chimeric, multispecific, humanized, and human monoclonal and polyclonal antibodies which specifically bind the biological molecule. The antibody may be a bi-specific antibody, avibody, diabody, tribody, tetrabody, nanobody, single domain antibody, VHH domain, human antibody, fully humanized antibody, partially humanized antibody, anticalin, adnectin, or affibody.

As used herein, the terms "binding specifically" and "specifically binding" in reference to an antibody, antibody variant, antibody derivative, antigen binding fragment, and the like refers to its capacity to bind to a given target molecule preferentially over other non-target molecules. For example, if the antibody, antibody variant, antibody derivative, or antigen binding fragment ("molecule A") is capable of "binding specifically" or "specifically binding" to a given target molecule ("molecule B"), molecule A has the capacity to discriminate between molecule B and any other number of potential alternative binding partners. Accordingly, when exposed to a plurality of different but equally accessible molecules as potential binding partners, molecule A will selectively bind to molecule B and other alternative potential binding partners will remain substantially unbound by molecule A. In general, molecule A will preferentially bind to molecule B at least 10-fold, preferably 50-fold, more preferably 100-fold, and most preferably greater than 100-fold more frequently than other potential binding partners. Molecule A may be capable of binding to molecules that are not molecule B at a weak, yet detectable level. This is commonly known as background binding and is readily discernible from molecule B-specific binding, for example, by use of an appropriate control.

As used herein, the term "kit" refers to any delivery system for delivering materials. Such delivery systems include systems that allow for the storage, transport, or delivery of reaction reagents (for example labels, reference samples, supporting material, etc. in the appropriate containers) and/or supporting materials (for example, buffers, written instructions for performing an assay etc.) from one location to another. For example, kits may include one or more enclosures, such as boxes, containing the relevant reaction reagents and/or supporting materials.

It will be understood that use of the term "between" herein when referring to a range of numerical values encompasses the numerical values at each endpoint of the range. For example, a polypeptide of between 10 residues and 20 residues in length is inclusive of a polypeptide of 10 residues in length and a polypeptide of 20 residues in length.

Any description of prior art documents herein, or statements herein derived from or based on those documents, is not an admission that the documents or derived statements are part of the common general knowledge of the relevant art. For the purposes of description all documents referred to herein are hereby incorporated by reference in their entirety unless otherwise stated.

Abbreviations

As used herein the abbreviation "CaP" refers to prostate cancer.

As used herein the abbreviations "LG" and "HG" refer to "low grade" (i.e. Gleason 3+3) and "high grade" (i.e. Gleason 3+4 or higher) prostate cancer.

As used herein the abbreviation "Acc" refers to accuracy.

As used herein the abbreviation "Sens" refers to sensitivity.

As used herein the abbreviations "Spec" or "Specs" refers to specificity.

As used herein the abbreviation "Log" refers to the natural logarithm.

As used herein the abbreviation "DRE" refers to digital rectal examination.

As used herein the abbreviation "NPV" refers to negative predictive value.

As used herein the abbreviation "PPV" refers to positive predictive value.

As used herein the abbreviation "AgCaP" refers to aggressive prostate cancer defined as prostate cancer with a Gleason score of 3+4 or greater.

As used herein the abbreviation "NoAgCaP" refers to non-aggressive prostate cancer defined as prostate cancer with a Gleason score of 3+3.

As used herein the abbreviation "NOT-AgCaP" refers to samples from subjects that do not have aggressive prostate cancer. These subjects may have non-aggressive prostate cancer or not have prostate cancer at all.

DETAILED DESCRIPTION

The development of reliable, convenient, and accurate tests for the diagnosis of aggressive prostate cancer remains an important objective, particularly during early stages when therapeutic intervention has the highest chance of success. In particular, initial screening procedures such as DRE and PSA are unable to discern between non-aggressive and aggressive prostate cancer effectively. The present invention provides combinations of biomarker/s and clinical variables indicative of aggressive prostate cancer in subjects that may have previously been determined to have a form of aggressive prostate cancer, or alternatively be suspected of having a form of aggressive prostate cancer on the basis of one or more alternative diagnostic tests (e.g. DRE, PSA testing). The biomarker/clinical variable combinations may thus be used in various methods and assay formats to differentiate between subjects with aggressive prostate cancer and those who do not have aggressive prostate cancer including, for example, subjects with non-aggressive prostate cancer and subjects who do not have prostate cancer (e.g. subjects with benign prostatic hyperplasia and healthy subjects).

Aggressive Prostate Cancer

The present invention provides methods for the diagnosis of aggressive prostate cancer. The methods involve detection of one or more combinations of biomarker/s and clinical variable/s as described herein.

Persons of ordinary skill in the art are well aware of standard clinical tests and parameters used to classify different prostate cancer Gleason grades and Epstein scores (see, for example, "2018 *Annual Report on Prostate Diseases*", Harvard Health Publications (Harvard Medical School), 2018; the entire contents of which are incorporated herein by cross-reference).

As known to those of ordinary skill in the art, prostate cancer can be categorized into stages according to the progression of the disease. Under microscopic evaluation, prostate glands are known to spread out and lose uniform structure with increased prostate cancer progression.

By way of non-limiting example, prostate cancer progression may be categorized into stages using the AJCC TNM staging system, the Whitmore-Jewett system and/or the D'Amico risk categories. Ordinarily skilled persons in the field are familiar with such classification systems, their features and their use.

By way of further non-limiting example, a suitable system of grading prostate cancer well known to those of ordinary skill in the field is the "Gleason Grading System". This system assigns a grade to each of the two largest areas of cancer in tissue samples obtained from a subject with prostate cancer. The grades range from 1-5, 1 being the least aggressive form and 5 the most aggressive form. Metastases are common with grade 4 or grade 5, but seldom occur, for example, in grade 3 tumors. The two grades are then added together to produce a Gleason score. A score of 2-4 is considered low grade; 5-7 intermediate grade; and 8-10 high grade. A tumor with a low Gleason score may typically grow at a slow enough rate to not pose a significant threat to the patient during their lifetime.

As known to those skilled in the art, prostate cancers may have areas with different grades in which case individual grades may be assigned to the two areas that make up most of the prostate cancer. These two grades are added to yield the Gleason score/sum, and in general the first number assigned is the grade which is most common in the tumour. For example, if the Gleason score/sum is written as '3+4', it means most of the tumour is grade 3 and less is grade 4, for a Gleason score/sum of 7.

A Gleason score/sum of 3+4 and above may be indicative of aggressive prostate cancer according to the present invention. Alternatively, a Gleason score/sum of under 3+4 may be indicative of non-aggressive prostate cancer according to the present invention.

An alternative system of grading prostate cancer also known to those of ordinary skill in the field is the "Epstein Grading System", which assigns overall grade groups ranging from 1-5. A benefit of the Epstein system is assigning a different overall score to Gleason score 7 (3+4) and Gleason score 7 (4+3) since have very different prognoses; Gleason score '3+4' translates to Epstein grade group 2; Gleason score '4+3' translates to Epstein grade group 3.

Biomarker and Clinical Variable Signatures

In accordance with the methods of the present invention, aggressive prostate cancer can be discerned by a combined approach of measuring one or more clinical variables identified herein along with the levels of one or more of the biomarkers identified herein.

A biomarker as contemplated herein may be an analyte. An analyte as contemplated herein is to be given its ordinary and customary meaning to a person of ordinary skill in the art and refers without limitation to a substance or chemical constituent in a biological sample (for example, blood, cerebral spinal fluid, urine, tear/s, lymph fluid, saliva, interstitial fluid, sweat, etc.) that can be detected and quantified. Non-limiting examples include cytokines, chemokines, as well as cell-surface receptors and soluble forms thereof.

A clinical variable as contemplated herein may be associated with or otherwise indicative of prostate cancer (e.g. non-aggressive and/or aggressive forms). The clinical variable may additionally be associated with other disease/s or condition/s. Non-limiting examples of clinical variables relevant to the present invention include subject Age, prostate volume, PSA level (free PSA, total PSA, % free PSA, [−2] ProPSA), PSA velocity, PSA density, Prostate Health Index, digital rectal examination (DRE), ethnic background, family history of prostate cancer, prior negative biopsy for prostate cancer.

By way of non-limiting example, a combination of clinical variables and biomarkers according to the present invention can be used for discerning between non-aggressive and aggressive forms of prostate cancer, and/or for diagnosing aggressive prostate cancer based on comparisons with a mixed control population of subjects having either non-aggressive prostate cancer or no prostate cancer. The combination of clinical variables and biomarkers may comprise or consist of one, two, three, four, five, or more than five individual biomarkers, in combination with one, two, three, four, five, or more than five individual clinical variables.

Without limitation, clinical variable/s, biomarker/s and combinations thereof used for diagnosing aggressive prostate cancer in accordance with the present invention may comprise or consist of:

Total PSA
Prostate volume
Digital Rectal Examination
Leptin
Prostate volume, leptin
Total PSA, leptin
Subject age, leptin-% free PSA, leptin
Prostate volume, total PSA, leptin
Prostate volume, % free PSA, leptin
Total PSA, % free PSA, leptin
Prostate volume, subject age, leptin
Total PSA, subject age, leptin-% free PSA, subject age, leptin
Total PSA, prostate volume, leptin, subject age, IL-7, VEGF
Total PSA, prostate volume, leptin, subject age, IL-7, VEGF, osteopontin, CD40L
Total PSA, % free PSA, prostate volume, leptin, osteopontin, HB4.WFDC2
Total PSA, DRE, leptin, subject age, IL-7, VEGF
Total PSA, DRE, leptin, subject age, osteopontin, VEGF
Total PSA, DRE, leptin, subject age, IL-7, VEGF, GPC-1
Total PSA, DRE, leptin, subject age, osteopontin, VEGF, GPC-1
total PSA, DRE, leptin, subject age, VEGF, IL-7, GPC-1, % free PSA
total PSA, DRE, leptin, subject age, VEGF, osteopontin, GPC-1, % free PSA
total PSA, DRE, leptin, subject age, prior negative biopsy, VEGF-C, osteopontin, GPC-1, CD40L, proPSA, % free PSA.

Detection and Quantification of Biomarkers

A biomarker or combination of biomarkers according to the present invention may be detected in a biological sample using any suitable method known to those of ordinary skill in the art.

In some embodiments, the biomarker or combination of biomarkers is quantified to derive a specific level of the biomarker or combination of biomarkers in the sample. Level/s of the biomarker/s can be analyzed according to the methods provided herein and used in combination with clinical variables to provide a diagnosis.

Detecting the biomarker/s in a given biological sample may provide an output capable of measurement, thus providing a means of quantifying the levels of the biomarker/s present. Measurement of the output signal may be used to generate a figure indicative of the net weight of the biomarker per volume of the biological sample (e.g. pg/mL; μg/mL; ng/ml etc.).

By way of non-limiting example only, detection of the biomarker/s may culminate in one or more fluorescent signals indicative of the level of the biomarker/s in the sample. These fluorescent signals may be used directly to make a diagnostic determination according to the methods of the present invention, or alternatively be converted into a different output for that same purpose (e.g. a weight per volume as set out in the paragraph directly above).

Biomarkers according to the present invention can be detected and quantified using suitable methods known in the art including, for example, proteomic techniques and techniques which utilize nucleic acids encoding the biomarkers.

Non-limiting examples of suitable proteomic techniques include mass spectrometry, protein array techniques (e.g. protein chips), gel electrophoresis, and other methods relying on antibodies having specificity for the biomarker/s including immunofluorescence, radiolabeling, immunohistochemistry, immunoprecipitation, Western blot analysis, Enzyme-linked immunosorbent assays (ELISA), fluorescent cell sorting (FACS), immunoblotting, chemiluminescence, and/or other known techniques used to detect protein with antibodies.

Non-limiting examples of suitable techniques relying on nucleic acid detection include those that detect DNA, RNA (e.g. mRNA), cDNA and the like, such as PCR-based techniques (e.g. quantitative real-time PCR; SYBR-green dye staining), UV spectrometry, hybridization assays (e.g. slot blot hybridization), and microarrays.

Antibodies having binding specificity for a biomarker according to the present invention, including monoclonal and polyclonal antibodies, are readily available and can be purchased from a variety of commercial sources (e.g. Sigma-Aldrich, Santa Cruz Biotechnology, Abcam, Abnova, R&D Systems etc.). Additionally or alternatively, antibodies having binding specificity for a biomarker according to the present invention can be produced using standard methodologies in the art. Techniques for the production of hybridoma cells capable of producing monoclonal antibodies are well known in the field. Non-limiting examples include the hybridoma method (see Kohler and Milstein, (1975) Nature, 256:495-497; Coligan et al. section 2.5.1-2.6.7 in Methods In Molecular Biology (Humana Press 1992); and Harlow and Lane Antibodies: A Laboratory Manual, page 726 (Cold Spring Harbor Pub. 1988)), the EBV-hybridoma method for producing human monoclonal antibodies (see Cole, et al. 1985, in Monoclonal Antibodies and Cancer Therapy, Alan R. Liss, Inc., pp. 77-96), the human B-cell hybridoma technique (see Kozbor et al. 1983, Immunology Today 4:72), and the trioma technique.

In some embodiments, detection/quantification of the biomarker/s in a biological sample (e.g. a body fluid or tissue sample) is achieved using an Enzyme-linked immunosorbent assay (ELISA). The ELISA may, for example, be based on colourimetry, chemiluminescence, and/or fluorometry. An ELISA suitable for use in the methods of the present invention may employ any suitable capture reagent and detectable reagent including antibodies and derivatives thereof, protein ligands and the like.

By way of non-limiting example, in a direct ELISA the biomarker of interest can be immobilized by direct adsorption onto an assay plate or by using a capture antibody attached to the plate surface. Detection of the antigen can then be performed using an enzyme-conjugated primary antibody (direct detection) or a matched set of unlabeled primary and conjugated secondary antibodies (indirect detection). The indirect detection method may utilise a labelled secondary antibody for detection having binding specificity for the primary antibody. The capture (if used) and/or primary antibodies may derive from different host species.

In some embodiments, the ELISA is a competitive ELISA, a sandwich ELISA, an in-cell ELISA, or an ELISPOT (enzyme-linked immunospot assay).

Methods for preparing and performing ELISAs are well known to those of ordinary skill in the art. Procedural considerations such as the selection and coating of ELISA plates, the use of appropriate antibodies or probes, the use of blocking buffers and wash buffers, the specifics of the detection step (e.g. radioactive or fluorescent tags, enzyme substrates and the like), are well established and routine in the field (see, for example, "The Immunoassay Handbook. Theory and applications of ligand binding, ELISA and related techniques", Wild, D. (Ed), 4th edition, 2013, Elsevier).

In other embodiments, detection/quantification of the biomarker/s in a biological sample (e.g. a body fluid or tissue sample) is achieved using Western blotting. Western blotting is well known to those of ordinary skill in the art (see for example, Harlow and Lane. Using antibodies. A Laboratory Manual. Cold Spring Harbor, New York: Cold Spring Harbor Laboratory Press, 1999; Bold and Mahoney, Analytical Biochemistry 257, 185-192, 1997). Briefly, antibodies having binding affinity to a given biomarker can be used to quantify the biomarker in a mixture of proteins that have been separated based on size by gel electrophoresis. A membrane made of, for example, nitrocellulose or polyvinylidene fluoride (PVDF) can be placed next to a gel comprising a protein mixture from a biological sample and an electrical current applied to induce the proteins to migrate from the gel to the membrane. The membrane can then be contacted with antibodies having specificity for a biomarker of interest, and visualized using secondary antibodies and/or detection reagents.

In other embodiments, detection/quantification of multiple biomarkers in a biological sample (e.g. a body fluid or tissue sample) is achieved using a multiplex protein assay (e.g. a planar assay or a bead-based assay). There are numerous multiplex protein assay formats commercially available (e.g. Bio-rad, Luminex, EMD Millipore, R&D Systems), and non-limiting examples of suitable multiplex protein assays are described in the Examples section of the present specification.

In other embodiments, detection/quantification of biomarker/s in a biological sample (e.g. a body fluid or tissue sample) is achieved by flow cytometry, which is a technique for counting, examining and sorting target entities (e.g. cells and proteins) suspended in a stream of fluid. It allows simultaneous multiparametric analysis of the physical and/or chemical characteristics of entities flowing through an optical/electronic detection apparatus (e.g. target biomarker/s quantification).

In other embodiments, detection/quantification of biomarker/s in a biological sample (e.g. a body fluid or tissue sample) is achieved by immunohistochemistry or immunocytochemistry, which are processes of localizing proteins in a tissue section or cell, by use of antibodies or protein binding agent having binding specificity for antigens in tissue or cells. Visualization may be enabled by tagging the antibody/agent with labels that produce colour (e.g. horseradish peroxidase and alkaline phosphatase) or fluorescence (e.g. fluorescein isothiocyanate (FITC) or phycoerythrin (PE)).

Persons of ordinary skill in the art will recognize that the particular method used to detect biomarker/s according to the present invention or nucleic acids encoding them is a matter of routine choice that does not require inventive input.

Measurement of Clinical Variables

A clinical variable or a combination of clinical variables according to the present invention may be assessed/measured/quantified using any suitable method known to those of ordinary skill in the art.

In some embodiments, the clinical variable/s may comprise relatively straightforward parameter/s (e.g. age) accessible, for example, via medical records.

In other embodiments, the clinical variable/s may require assessment by medical and/or other methodologies known to those of ordinary skill in the art. For example, prostate volume may require measurement by techniques using ultrasound (e.g. transabdominal ultrasonography, transrectal ultrasonography), magnetic resonance imaging, and the like. DRE results are typically scored as normal or abnormal/suspicious.

Clinical variable/s relevant to the diagnostic methods of the present invention may be assessed, measured, and/or quantified using additional or alternative methods including, by way of example, digital rectal exam, biopsy and/or MRI fusion.

Clinical variable/s such as PSA level, free PSA, total PSA, % free PSA, [−2] ProPSA, may be determined by use of clinical immunoassays such as the Beckman Coulter Access 2 analyzer and associated Hybritech assays or other similar assays. PHI can be derived from these measurements using the formula [−2] proPSA/fPSA×√PSA PSA velocity.

Analysis of Biomarkers, Clinical Variables and Diagnosis

According to methods of the present invention, the assessment of a given combination of clinical variable/s and biomarker/s may be used as a basis to diagnose aggressive prostate cancer, or determine an absence of aggressive prostate cancer in a subject of interest.

In relation to assessing biomarker component/s of the combination, the methods generally involve analyzing the targeted biomarker/s in a given biological sample or a series of biological samples to derive a quantitative measure of the biomarker/s in the sample. Suitable biomarker/s include, but are not limited to, those biomarkers and biomarker combinations referred to above in the section entitled "Biomarker and clinical variable signatures", and the Examples of the present application. By way of non-limiting example only, the quantitative measure may be in the form of a fluorescent signal or an absorbance signal as generated by an assay designed to detect and quantify the biomarker/s. Additionally or alternatively, the quantitative measure may be provided in the form of weight/volume measurements of the biomarker/s in the sample/s.

Similarly, in relation to assessing clinical variable components of the combination, assessment of features such as, for example, subject age and/or prostate volume can be made and a representative value generated (e.g. a numerical value). Suitable clinical variable/s include, but are not limited to, those clinical variable/s referred to above in the section entitled "*Biomarker and clinical variable signatures*", and the Examples of the present application.

In some embodiments, the methods of the present invention may comprise a comparison of levels of the biomarker/s and clinical variable/s in patient populations known to suffer from aggressive prostate cancer, known to suffer from non-aggressive cancer, or known not to suffer from prostate cancer (e.g. benign prostatic hyperplasia patient populations and/or healthy patient populations). For example, levels of biomarker/s and measures of clinical variable/s can be ascertained from a series of biological samples obtained from patients having an aggressive prostate cancer compared to patients having a non-aggressive prostate cancer. Aggressive prostate cancer may be characterized by a minimum Gleason grade or score/sum (e.g. at least 7 (e.g. 3+4 or 4+3, 5+2), or at least 8 (e.g. 4+4, 5+3 or 3+5).

The level of biomarker/s observed in samples from each individual population and clinical variable/s of the individuals within each population may be collectively analyzed to determine a threshold value that can be used as a basis to provide a diagnosis of aggressive prostate cancer, or an absence of aggressive prostate cancer. For example, a biological sample from a patient confirmed or suspected to be suffering from aggressive prostate cancer can be analyzed and the levels of target biomarker/s according to the present invention determined in combination with an assessment of clinical variable/s. Comparison of levels of the biomarker/s and the clinical variable/s in the patient's sample to the threshold value/s generated from the patient populations can serve as a basis to diagnose aggressive prostate cancer or an absence of aggressive prostate cancer.

Accordingly, in some embodiments the methods of the present invention comprise diagnosing whether a given patient suffers from aggressive prostate cancer. The patient may have been previously confirmed to have or suspected of having prostate cancer, for example, as a result of a DRE and/or PSA test. In such situations, it is advantageous for the patient to determine whether the patient is likely to have aggressive prostate cancer or not, in accordance with the methods described herein avoiding the need for a prostate biopsy.

Without any particular limitation, a diagnostic method according to the present invention may involve discerning whether a subject has or does not have aggressive prostate cancer. The method may comprise obtaining a first series of biological samples from a first group of patients biopsy-confirmed to be suffering from non-aggressive prostate cancer, and a second series of biological samples from a second group of patients biopsy-confirmed to be suffering from aggressive prostate cancer. A threshold value for discerning between the first and second patient groups may be generated by measuring clinical variable/s such as subject age and/or prostate volume and/or DRE status and detecting levels/concentrations of one, two, three, four, five or more than five biomarkers in the first and second series of biological samples to thereby obtain a biomarker level for each biomarker in each biological sample of each series. Clinical variables and prostate volume are considered "variables" in determining the presence or absence of aggressive prostate cancer. The variables may be combined in a manner that allows discrimination between samples from the first and second group of patients. A threshold value or probability score may be selected from the combined variable values in a suitable manner such as any one or more of a method that: reduces the misclassification rate between the first and second group of patients; increases or maximizes the sensitivity in discriminating between the first and second group of patients; and/or increases or maximizes the specificity in discriminating between the first and second group of patients; and/or increases or maximises the accuracy in discriminating between the first and second group of patients. A suitable algorithm and/or transformation of individual or combined variable values obtained from the test subject and its biological sample may be used to generate the variable values for comparison to the threshold value. In some embodiments, one or more variables used in deriving the threshold value and/or the test subject score are weighted.

In some embodiments, the subject may receive a negative diagnosis for aggressive prostate cancer if the subject's score generated from the combined biomarker level/s and clinical variable/s is less than the threshold value. In some embodiments, the subject receives a positive diagnosis for aggressive prostate cancer if the subject's score generated from the combined biomarker level/s and clinical variable/s is less than the threshold value. In some embodiments, the subject receives a negative diagnosis for aggressive prostate cancer if the subject's score generated from the combined biomarker level/s and clinical variable/s is more than the threshold value. In some embodiments, the patient receives a positive diagnosis for aggressive prostate cancer if the subject's score generated from the combined biomarker level/s and clinical variable/s is more than the threshold value.

Suitable and non-limiting methods for conducting these analyses are described in the Examples of the present application.

One non-limiting example of such a method is Receiver Operating Characteristic (ROC) curve analysis. Generally, the ROC analysis may involve comparing a classification for each patient tested to a 'true' classification based on an appropriate reference standard. Classification of multiple patients in this manner may allow derivation of measures of sensitivity and specificity. Sensitivity will generally be the proportion of correctly classified patients among all of those that are truly positive, and specificity the proportion of correctly classified cases among all of those that are truly negative. In general, a trade-off may exist between sensitivity and specificity depending on the threshold value selected for determining a positive classification. A low threshold may generally have a high sensitivity but relatively low specificity. In contrast, a high threshold may generally have a low sensitivity but a relatively high specificity. A ROC curve may be generated by inverting a plot of sensitivity versus specificity horizontally. The resulting inverted horizontal axis is the false positive fraction, which is equal to the specificity subtracted from 1. The area under the ROC curve (AUC) may be interpreted as the average sensitivity over the entire range of possible specificities, or the average specificity over the entire range of possible sensitivities. The AUC represents an overall accuracy measure and also represents an accuracy measure covering all possible interpretation thresholds.

While methods employing an analysis of the entire ROC curve are encompassed, it is also intended that the methods may be extended to statistical analysis of a partial area (partial AUC analysis). The choice of the appropriate range along the horizontal or vertical axis in a partial AUC analysis may depend at least in part on the clinical purpose. In a clinical setting in which it is important to detect the presence of aggressive prostate cancer with high accuracy, a range of relatively high false positive fractions corresponding to high sensitivity (low false negatives) may be used. Alternatively, in a clinical setting in which it is important to exclude the presence of aggressive prostate cancer, a range of relatively low false positive fractions equivalent to high specificities (high true positives) may be used.

Subjects, Samples and Controls

A subject or patient referred to herein encompasses any animal of economic, social or research importance including bovine, equine, ovine, canine, primate, avian and rodent species. A subject or patient may be a mammal such as, for example, a human or a non-human mammal. Subjects and patients as described herein may or may not suffer from aggressive prostate cancer, or may or may not suffer from a non-aggressive prostate cancer.

In accordance with methods of the present invention, clinical variable/s of a given subject may be assessed and the output combined with levels of biomarker/s measured in a sample from the subject.

A sample used in accordance the methods of the present invention may be in a form suitable to allow analysis by the skilled artisan. Suitable samples include various body fluids such as blood, plasma, serum, semen, urine, tear/s, cerebral spinal fluid, lymph fluid, saliva, interstitial fluid, sweat, etc. The urine may be obtained following massaging of the prostate gland.

The sample may be a tissue sample, such as a biopsy of the tissue, or a superficial sample scraped from the tissue. The tissue may be from the prostate gland. In another embodiment the sample may be prepared by forming a suspension of cells made from the tissue.

The methods of the present invention may, in some embodiments, involve the use of control samples.

A control sample is any corresponding sample (e.g. tissue sample, blood, plasma, serum, semen, tear/s, or urine) that is taken from an individual without aggressive prostate cancer. In certain embodiments, the control sample may comprise or consist of nucleic acid material encoding a biomarker according to the present invention.

In some embodiments, the control sample can include a standard sample. The standard sample can provide reference amounts of biomarker at levels considered to be control levels. For example, a standard sample can be prepared to mimic the amounts or levels of a biomarker described herein in one or more samples (e.g. an average of amounts or levels from multiple samples) from one or more subjects, who may or may not have aggressive prostate cancer.

In some embodiments control data may be utilized. Control data, when used as a reference, can comprise compilations of data, such as may be contained in a table, chart, graph (e.g. database or standard curve) that provide amounts or levels of biomarker/s and/or clinical variable feature/s considered to be control levels. Such data can be compiled, for example, by obtaining amounts or levels of the biomarker in one or more samples (e.g. an average of amounts or levels from multiple samples) from one or more subjects, who may or may not have aggressive prostate cancer. Clinical variable control data can be obtained by assessing the variable in one or more subjects who may or may not have aggressive prostate cancer.

Kits

Also contemplated herein are kits for performing the methods of the present invention. The kits may comprise reagents suitable for detecting one or more biomarker/s described herein, including, but not limited to, those biomarker and biomarker combinations referred to in the section above entitled "Biomarker and clinical variable signatures".

By way of non-limiting example, the kits may comprise one or a series of antibodies capable of binding specifically to one or a series of biomarkers described herein.

Additionally or alternatively, the kits may comprise reagents and/or components for determining clinical variable/s of a subject (e.g. PSA levels), and/or for preparing and/or conducting assays capable of quantifying one or more biomarker/s described herein (e.g. reagents for performing an ELISA, multiplex bead-based Luminex assay, flow cytometry, Western blot, immunohistochemistry, gel electrophoresis (as suitable for protein and/or nucleic acid separation) and/or quantitative PCR.

Additionally or alternatively, the kits may comprise equipment for obtaining and/or processing a biological sample as described herein, from a subject.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

The present invention will now be described with reference to specific example(s), which should not be construed as in any way limiting.

Example 1: Background & Study Design 1.1 Clinical Diagnostic Pathways

A typical clinical diagnostic pathway for aggressive prostate cancer is shown in FIG. One.

In brief:

1. Primary care physician refers patient with raised PSA result to a urologist.
2. Urologist repeats PSA test.
3. If above the age-adjusted PSA cut-off, the patient proceeds to biopsy.
4. If the biopsy shows a Gleason score 3+4 (or above) treatment with various modalities such as surgery, radiation, drugs in initiated.
5. If biopsy shows Gleason score of 3+3 physician may consider transperineal biopsy, MRI or active surveillance.

FIG. Two outlines an exemplary strategy for implementation of the diagnostic methods of the present invention. Briefly:

1. The primary care physician refers patient with raised PSA result to a urologist.
2. The urologist repeats PSA and performs diagnostic method according to the present invention
3. If the method provides a 'no aggressive cancer' determination the patient does not proceed to biopsy but is followed up in 3-6 months, with possible biopsy at 1 year
4. If the method provides an aggressive diagnosis the urologist orders a biopsy. If the biopsy shows Gleason score 3+4 (or above) treat with various modalities such as surgery, radiation, drugs.
5. If the biopsy shows Gleason score of 3+3 a transperineal biopsy, MRI or active surveillance can be considered.

1.2 Overview of Model Development

A summary of the strategy used to identify model components follows below:

Samples were collected from a representative contemporary US patient population ('CUSP' prospective trial).

Samples were measured using current prostate cancer diagnosis tests: PSA, % free PSA, Prostate Health Index (PHI). Note that proPSA values are obtained from the PHI test measurements.

Measurements of clinical variables used in risk calculators were made (age, ethnic background, PSA, DRE, prostate volume, family history, prior biopsy results).

The performance of clinical tests/factors at differentiating aggressive vs non-aggressive CaP in this cohort were determined.

Samples were measured using a panel of multiple biomarkers.

Univariate analysis of clinical variables and individual biomarkers at differentiating aggressive vs non-aggressive CaP in this cohort was carried out.

Models were developed combining clinical tests/factors and biomarkers and adding up to 5 biomarkers Models were also developed using existing clinical tests/factors and adding either one, two or three new markers (note this approach minimizes the number of new markers that need to be added to existing tests).

1.3 Patient Cohort and Trial Parameters 1

A prospective clinical trial was designed to collect a representative contemporary patient population from the United States of America. This meant that the study had representative frequencies of different ethnic groups in the USA and also reflected the contemporary prevalence of either no cancer, non-aggressive prostate cancer or aggressive prostate cancer. All patients who were recruited to the trial presented on the basis of an elevated age adjusted PSA and underwent biopsy at their local clinical site. Serum and plasma samples were collected together with a blood sample for standardized PSA test (performed in a central lab on an Abbott Architect machine). In addition to the biopsy assessment at the local site, a central biopsy review was performed by a single pathologist. The central PSA value and central biopsy classification were used for model development. Correlation of central PSA with the PSA used for enrolment into the trial was high (FIG. Three). Similarly, there was overall a high correlation between site Gleason and central Gleason scores (FIG. Four), however central Gleason score showed upgrading of 14 non-aggressive cancers to aggressive cancer and one down grade from aggressive to non-aggressive cancer.

The prospective non-randomized case-control study was designed having primary and secondary endpoints:

Primary endpoint: detection of prostate cancer vs non-prostate cancer patients

Secondary endpoint: differentiation of aggressive (defined as Gleason≥3+4) vs non-aggressive (defined as Gleason 3+3) prostate cancer The study was conducted in 12 US research centers and accrued a total of 384 subjects:

Arm 1 (Healthy Normal): 52 patients

Arm 2 (Prostate Biopsy): 332 (100%) patients

Cohort A: 148 patients (45%), no cancer

Cohort B: 64 patients (19%), GS=6, CaP

Cohort C: 120 patients (36%), GS≥7 (≥3+4), CaP

Serum and plasma samples were collected, and standardized PSA test and centralized pathology were reviewed (both Gleason Score and Epstein scores).

Inclusion criteria were as follows:

ARM 1: Healthy Normal (HN)

Subjects 50 years or older

Low PSA (performed at most 12 months prior) with low PSA defined as: <1.5 ng/ml between ages 50 and 60, <3 ng/mL above age 60

Signed informed consent

ARM 2: Prostate Biopsy

Subjects 40 years or older

All subjects who were referred for or had undergone either a de novo or a repeat prostate biopsy for high PSA where high PSA was defined as: ≥1 ng/ml between ages 40 and 49, ≥2 ng/ml between ages 50 and 60, ≥3 ng/mL for age 60 and above Signed informed consent.

Exclusion criteria for ARM 1 were as follows:

1. Any subject with medical history of cancer except basal skin cancer or squamous skin cancer.
2. Any subject without PSA result or with PSA not within approved timeframe of at most 12 months.
3. Any subject who has had a DRE, ejaculated, or undertaken vigorous bike riding within 72 hours of blood draw.
4. Any subject with other lower urinary tract manipulation (defined as urological surgery, including prostate biopsy) in the previous 6 weeks from blood draw.
5. Any subject with benign prostatic hyperplasia as defined by the investigators review.
6. Any subject taking Saw Palmetto was excluded unless there is a minimum wash out of 30 days since last dose.
7. Any subject taking Androgen Deprivation Therapy
8. Any subject taking Casadex is excluded unless there is a minimum wash out of 30 days since the last dose.

9. Any patient currently taking an experimental agent-placebo control or unknown agent 10. Any subject taking 5 alpha reductase inhibitors is excluded unless there is a minimum 6 weeks washout since the last dose of finasteride and a minimum of 6 months wash out since the last dose of Dutasteride.

11. Any subject confirmed by the investigator to currently be suffering from prostatitis, proctodynia, or urinary tract infection.

ARM 2 prostate cancer biopsy exclusion criteria were as follows:

1. Any subject with medical history of cancer other than prostate cancer except basal or squamous skin cancer.

2. Any subject without PSA result or with PSA not within approved timeframe of at most 12 months.

3. Any subject who has had a DRE, ejaculated, or undertaken vigorous bike riding within 72 hours of blood draw 4. Any subject with other lower urinary tract manipulation (defined as urological surgery, including prostate biopsy) in the previous 6 weeks from blood draw.

5. Any subject taking Saw Palmetto is excluded unless there is a minimum wash out of 30 days since the last dose.

6. Any subject taking Androgen Deprivation Therapy 7. Any subject taking Casadex is excluded unless there is a minimum wash out of 30 days since the last dose.

8. Any patient currently taking an experimental agent-placebo control or unknown agent.

9. Any subject taking 5 alpha reductase inhibitors is excluded unless there is a minimum of 6 weeks wash-out since the last dose of finasteride and a minimum of 6 months wash out since the last dose of Dutasteride.

10. Any subject confirmed by the investigator to currently be suffering from prostatitis, proctodynia or urinary tract infection.

Study patient characteristics are outlined in Tables 1~4 below.

TABLE 1

| patient characteristics-age and BMI (CaP-prostate cancer, LG CaP-Gleason 3 + 3 prostate cancer, HG CaP Gleason ≥3 + 4 prostate cancer) | | | | | | |
|---|---|---|---|---|---|
| Dimension | All patients | Arm 1 Non-CaP | Arm 2 Non-CaP | Arm 2 CaP | Arm 2 LG CaP | Arm 2 HG CaP |
| Total | 384 | 52 | 148 | 184 | 64 | 120 |
| Age Mean (SD) | 64 (8.0) | 59 (6.1) | 64 (7.7) | 65 (8.2) | 62 (7.5) | 66 (8.2) |
| Age Median (Range) | 64 (40-85) | 58 (50-74) | 65 (40-82) | 65 (45-85) | 62 (45-79) | 66 (48-85) |
| >50 years, N (%) | 372 (97%) | 52 (100%) | 141 (95%) | 179 (97%) | 61 (95%) | 118 (98%) |
| BMI Mean (SD) | 30 (5.9) | 31 (6.0) | 29 (4.8) | 30 (6.6) | 30 (6.7) | 29 (6.4) |
| BMI Median (Range) | 29 (18-73) | 29 (22-50) | 29 (20-44) | 28 (18-72) | 29 (21-60) | 28 (18-73) |

TABLE 2

| patient characteristics-DRE and Gleason/Epstein scores (DRE: Digital Rectal Exam) | | | | | | |
|---|---|---|---|---|---|
| DRE status and Gleason score | All patients | Arm 1 Non-CaP | Arm 2 Non-CaP | Arm 2 CaP | Arm 2 LG CaP | Arm 2 HG CaP |
| DRE status | | | | | | |
| Normal | 264 (69%) | 30 (58%) | 115 (78%) | 119 (65%) | 49 (77%) | 70 (58%) |
| Suspicious* | 55 (14%) | 1 (2%) | 15 (10%) | 39 (21%) | 7 (11%) | 32 (27%) |
| Unknown | 65 (17%) | 21 (40%) | 18 (12%) | 26 (14%) | 8 (15%) | 18 (15%) |
| Gleason Score/Epstein, N (%) | | | | | | |
| 6/1 | | | | 64 (35%) | 64 (100%) | |
| 7 (3 + 4)/2 | | | | 58 (32%) | | 58 (48%) |
| 7 (4 + 3)/3 | | | | 43 (23%) | | 43 (36%) |
| 8/4 | | | | 5 (3%) | | 5 (4%) |
| 9/5 | | | | 14 (8%) | | 14 (12%) |

TABLE 3

| patient characteristics-prostate volume and family history | | | | | | |
|---|---|---|---|---|---|
| Dimension | All patients | Arm 1 Non-CaP | Arm 2 Non-CaP | Arm 2 CaP | Arm 2 LG CaP | Arm 2 HG CaP |
| Prostate Vol (cc)* Mean (SD) | 52 (30) | — | 64 (35) | 42 (19) | 46 (18) | 40 (20) |
| Prostate Vol (cc)* Median (Range) | 43 (13-189) | — | 52 (15-189) | 38 (13-121) | 40 (18-95) | 37 (13-121) |

TABLE 3-continued

| | | Arm 1 | | | Arm 2 | |
| Dimension | All patients | Non-CaP | Arm 2 Non-CaP | Arm 2 CaP | LG CaP | Arm 2 HG CaP |
|---|---|---|---|---|---|---|
| | | | 1$^{st}$ Deg Family History | | | |
| Yes | 100 (26%) | 10 (19%) | 33 (22%) | 57 (31%) | 25 (39%) | 32 (27%) |
| No | 244 (64%) | 36 (69%) | 98 (66%) | 110 (60%) | 33 (52%) | 77 (64%) |
| Unknown | 40 (10%) | 6 (12%) | 17 (11%) | 17 (9%) | 6 (9%) | 11 (9%) |

TABLE 4 patient characteristics-PSA with different strata

| Central PSA | All patients | Arm 1 Non-CaP | Arm 2 Non-CaP | Arm 2 CaP | Arm 2 LG CaP | Arm 2 HG CaP |
|---|---|---|---|---|---|---|
| Mean (SD) | 7.4 (14) | 1.1 (0.7) | 5.8 (3.0) | 10.4 (20) | 5.8 (3) | 12.8 (24) |
| Median (Range) | 5.5 (0.2-237) | 0.8 (0.2-2.7) | 5.0 (1.2-18) | 6.7 (1.5-237) | 5.6 (1.5-17.3) | 7.5 (2.4-237) |
| <2 ng/ml, N (%) | 46 (12%) | 42 (81%) | 3 (2%) | 1 (1%) | 1 (2%) | 0 (0%) |
| 2-10 ng/ml, N (%) | 287 (75%) | 10 (19%) | 135 (91%) | 142 (77%) | 58 (91%) | 84 (70%) |
| 4-10 ng/ml, N (%) | 221 (58%) | 0 (0%) | 100 (68%) | 121 (66%) | 42 (66%) | 79 (66%) |
| 3-15 ng/ml, N (%) | 281 (73%) | 0 (0%) | 127 (86%) | 154 (84%) | 54 (84%) | 100 (83%) |
| 10-20 ng/ml, N (%) | 42 (11%) | 0 (0%) | 11 (7%) | 31 (17%) | 5 (8%) | 26 (22%) |
| >20 ng/ml, N (%) | 10 (3%) | 0 (0%) | 0 (0%) | 10 (5%) | 0 (0%) | 10 (8%) |
| >50 yr + PSA 4-10, N (%) | 213 (55%) | — | 97 (66%) | 116 (63%) | 39 (61%) | 77 (64%) |
| >50 yr + PSA 4-10 + Normal DRE, N (%) | 154 (44%) | — | 77 (52%) | 77 (42%) | 33 (52%) | 44 (37%) |

1.4 Sample Collection

Whole blood samples taken from patients were stored at 4° C. and subjected to centrifugation within 2 hours of collection to separate serum components, which were stored at −20° C. Samples were shipped from the collection sites then thawed, aliquoted, and stored at −80° C.

1.5 Multi-Analyte Arrays

Patient serum samples were thawed at room temperature then transferred to a 1.5 mL centrifuge tubes. The samples were spun at 20,000 g for 5 mins at room temperature. The middle fraction of each sample, avoiding any pellet or lipid layer, was transferred to 96-well plates and diluted with appropriate buffer. These sample plates were stored at −80° C. until they could be processed and run at the Australian Proteome Analysis Facility as per the manufacturer's instructions. The samples were analyzed using a Bioplex 200 analyzer according to manufacturer's instructions. Two custom kits were obtained from R&D systems for this analysis:

The cytokines and growth factors contained in each kit were as follows:

29-plex: NT-proANP, Prolactin, ANGPTL3, Kallikrein 3.PSA, Endoglin, HGF, VEGF-C, CD31.Pecam1, Tie-2, SCF, VEGF R2.KDR.Flk-1, ErbB2.Her2, CXCL13.BLC.BCA-1, IL-7, FGF-b, HE4.WFDC-2, Angiopoietin-1, MADCAM-1, Leptin, BDNF, CD40 Ligand, IL-18, IL-6 R Alpha, uPA.Urokinase, PDGF-AB, Osteopontin, Mesothelin, EGF, CXCL12.SDF-1 alpha 3-plex: VEGF (VEGFA), G-CSF, Glypican-1

1.6 Prostate Health Index (PHI) Testing

Samples were sent for testing at Sullivan Nicolaides laboratories in Brisbane Australia. The PHI test consists of measurement of total PSA, free PSA and [−2] ProPSA components which are then combined using an algorithm to give a PHI score. The percent free PSA (% free PSA) can be calculated by dividing the free PSA concentration by the total PSA concentration and expression as a percentage.

1.7 Model Development and Results

Samples from patients diagnosed with biopsy-confirmed prostate cancer from Arm 2 of the clinical trial were used for development of models differentiating aggressive (Gleason≥3+4) from non-aggressive prostate cancer patients.

A combined database was generated linking the clinical and demographic factors to the analyte sample values. Following initial investigations, analyte concentrations derived from serum rather than plasma were used.

Samples were measured using 29-plex and 3-plex Luminex kits. Extremely hemolyzed samples were excluded during model development. Measured sample analyte concentrations that were higher than the top standard of the recombinant protein standard curve were set at the value of the highest standard. Measured protein concentrations that were lower than the bottom standard of the recombinant protein standard curve were set at the value of the lowest standard.

Clinical data was available for 184 CaP patients (64 non-aggressive and 120 aggressive cancer patients). 5 samples were removed due to extreme hemolysis leaving 179 CaP patients (62 non-aggressive CaP and 117 AgCaP) available for analysis. 169 of these patients (56 non-aggressive CaP, 113 AgCaP) had Prostate Volume data, 179 of these patients (117 AgCaP vs 62 Non-Ag CaP) had DRE data, 176 patients had % free PSA and PHI (62 non-aggressive CaP, 114 AgCaP). 166 patients (56 non-aggressive and 110 AgCaP) had every data component (including PV, % PSA, and PHI) for analysis.

The goal of the model development was to improve on currently available clinical tests such as PSA, prostate volume, % free PSA or PHI in the ability to accurately predict the presence of aggressive vs non-aggressive prostate cancer. Exploratory model development work indicated Leptin as a frequent component of high performing multivariate models, therefore it was selected for more detailed investigation.

Model development and ROC analyses (aggressive prostate cancer versus non-aggressive prostate cancer) were performed for PSA (Model 1), prostate volume (Model 2) and Leptin (Model 3), % free PSA (model 4) and PHI (Model 5).

TABLE 5

| No | Variable | Transformation | Log Odd ratio |
|---|---|---|---|
| 1 | (Intercept) | | −3.1011 |
| | Central.PSA | Log | 1.9875 |

TABLE 6

| Metric | Threshold | Sens | Specs | Acc | Youden |
|---|---|---|---|---|---|
| Max Acc | 0.450 | 0.95 | 0.29 | 72.07 | 1.24 |
| Max Youden | 0.706 | 0.52 | 0.86 | 63.69 | 1.38 |

TABLE 7

| | Variable | Raw Value | Transformation | Transformed Value | Co-efficient | Partial products |
|---|---|---|---|---|---|---|
| 1 | Intercept | 1 | None | | −3.1011 | −3.1011 |
| 2 | Central PSA | 5 | Log | 1.609438 | 1.9875 | 3.198758 |

$\mathrm{Logit}(P) = \log(P/1 - P) = \mathrm{intercept} + \sum \log \text{ odds ratio}_i \times$    SUM    0.097658

$\log(\mathrm{marker}_i)$ $$P = \frac{\exp(\mathrm{Logit}(P))}{1 + \exp(\mathrm{Logit}(P))}$$    0.5243951

The probability of the patient having aggressive CaP is 0.524
If the cutpoint is set at the Youden value of ~0.706, the patient would be classified as having non-aggressive prostate cancer (a) ROC Analyses on PSA-Model 1
Algorithm outputs for Model 1 (PSA) are indicated below: P is probability of that a patient has aggressive prostate cancer. In other words, the risk of prostate cancer of a patient is P.

*Logit (P) =*

$\mathrm{Log}(P/1 - P) = \mathrm{intercept} + \sum_{i=1}^{N} (\mathrm{coefficient}_i \times \mathrm{transformed}\ (\mathrm{variable}_i))$ In the case of model 1, there is 1 variable. The transformation of PSA is applied, then multiplied by the co-efficient. Finally the resulting products are summed to give the Log it(P) value, which is then used to determine the probability of aggressive cancer using the formula:

$$P_{(Aggressive\ prostate\ cancer)} = \frac{\exp(Logit(P))}{1 + \exp(Logit(P))}$$

For example,
Log it (P)$_{Model\ 1}$=−3.1011+1.9875*log (Central. PSA)

P(Aggressive Prostate Cancer) =

$$\frac{\exp(-3.1011 + 1.9875 * \log(\mathrm{Central}.PSA))}{1 + \exp(-3.1011 + 1.9875 * \log(\mathrm{Central}.PSA))}$$

The results of a ROC curve analysis performed on PSA levels under Model 1 are shown in FIG. Five/Tables 5-7.

(b) ROC Analyses on Prostate Volume (PV)-Model 2
Algorithm outputs for Model 2 (PV) are indicated below: P is probability of that a patient has aggressive prostate cancer. In other words, the risk of prostate cancer of a patient is P.

$\mathrm{Logit}\ (P) = \mathrm{Log}(P/1 - P)$ $= \mathrm{intecept} + \sum_{i=1}^{n} (\mathrm{coefficient}_i \times \mathrm{transformed}(\mathrm{variable}_i))$ In the case of model 2, there is 1 variable. The transformation of PV is applied, then multiplied by the coefficient. Finally the resulting products are summed to give the Log it(P) value. This is then used to determine the probability of aggressive cancer using the formula:

$$P_{(Aggressive\ prostate\ cancer)} = \frac{\exp(\mathrm{Logit}(P))}{1 + \exp(\mathrm{Logit}(P))}$$

For example,
Log it (P)$_{Model\ 2}$=4.1767−0.9440*log(Prostate Volume).

P(Aggressive Prostate Cancer) =

$$\frac{\exp(4.1767 - 0.9440 * \log(\mathrm{Prostate\ Volume}))}{1 + \exp(4.1767 - 0.9440 * \log(\mathrm{Prostate\ Volume}))}$$

The results of a ROC curve analysis performed on PV under Model 2 are shown in FIG. Six/Tables 8-10.

TABLE 8

| No | Variable | Transformation | Log Odd ratio |
|----|----------|----------------|---------------|
| | (Intercept) | | 4.1767 |
| 1 | Prostate Volume | Log | −0.9440 |

TABLE 9

| Metric | Threshold | Sens | Specs | Acc | Youden |
|--------|-----------|------|-------|-----|--------|
| Max Acc | 0.510 | 0.97 | 0.10 | 68.05 | 1.06 |
| Max Youden | 0.632 | 0.76 | 0.46 | 66.27 | 1.23 |

TABLE 10

| | Variable | Raw Value | Transformation | Transformed Value | Co-efficient | Partial products |
|---|----------|-----------|----------------|-------------------|--------------|------------------|
| 1 | Intercept | 1 | None | | 4.1767 | 4.1767 |
| 2 | Prostate Volume | 56 | Log | 4.025352 | −0.9440 | −3.799932 |

$$\text{Logit}(P) = \log\left(P/1 - P\right) = \text{intercept} + \sum \text{log odds ratio}_i \times \log(\text{marker}_i)$$

| | |
|---|---|
| SUM | 0.3767677 |

$$P = \frac{\exp(\text{Logit}(P))}{1 + \exp(\text{Logit}(P))}$$    0.5930933

The probability of the patient having aggressive CaP is 0.593
If the cutpoint is set at the Youden value of ~0.63, the patient would be classified as having non-aggressive prostate cancer (c) ROC Analyses on Leptin—Model 3

Algorithm outputs for Model 3 (leptin) are indicated below:

P is probability of that a patient has aggressive prostate cancer. In other words, the risk of prostate cancer of a patient is P.

$$\text{Logit}(P) = \log\left(P/1 - P\right)$$
$$= \text{intecept} + \sum_{i=1}^{n}(\text{coefficient}_i \times \text{transformed}(\text{variable}_i))$$

In the case of model 3, there is 1 variable. The transformation of Leptin is applied, then multiplied by the coefficient. Finally the resulting products were summed to give the Log it(P) value. This was then used to determine the probability of aggressive cancer using the formula:

$$P_{(Aggressive\ prostate\ cancer)} = \frac{\exp(\text{Logit}(P))}{1 + \exp(\text{Logit}(P))}$$

For example, $$\text{Log it }(P)_{Model\ 3} = 3.7217 - 0.3403 * \log(\text{Leptin}).$$

$$P(\text{Aggressive Prostate Cancer}) = \frac{\exp(3.7217 - 0.3403 * \log(\text{Leptin}))}{1 + \exp(3.7217 - 0.3403 * \log(\text{Leptin}))}$$

The results of a ROC curve analysis performed on leptin under Model 3 are shown in FIG. Seven/Tables 11-13.

TABLE 11

| No | Variable | Transformation | Log Odd ratio |
|----|----------|----------------|---------------|
| | (Intercept) | | 3.7217 |
| 1 | Leptin | Log | −0.3403 |

TABLE 12

| Metric | Threshold | Sens | Specs | Acc | Youden |
|--------|-----------|------|-------|-----|--------|
| Max Acc | 0.515 | 1 | 0.04 | 68.05 | 1.04 |
| Max Youden | 0.719 | 0.26 | 0.89 | 46.74 | 1.15 |

TABLE 13

| | Variable | Raw Value | Transformation | Transformed Value | Co-efficient | Partial products |
|---|----------|-----------|----------------|-------------------|--------------|------------------|
| 1 | Intercept | 1 | None | | 3.7217 | 3.7217 |
| 2 | Leptin | 21859.78 | Log | 9.992404 | −0.3403 | −3.400415 |

$$\text{Logit}(P) = \log\left(P/1 - P\right) = \text{intercept} + \sum \text{log odds ratio}_i \times \log(\text{marker}_i)$$

| | |
|---|---|
| SUM | 0.3212849 |

TABLE 13-continued

| Variable | Raw Value | Transformation | Transformed Value | Co-efficient | Partial products |
|---|---|---|---|---|---|
| | | | $P = \dfrac{\exp(\text{Logit}(P))}{1 + \exp(\text{Logit}(P))}$ | | 0.5796374 |

The probability of the patient having aggressive CaP is 0.580
If the cutpoint is set at the Youden value of ~0.719, the patient would be classified as
having non-aggressive prostate cancer (d) ROC Analyses for % Free PSA-Model 4

Algorithm outputs for Model 4 are indicated below:

P is probability of that a patient has aggressive prostate cancer. In other words, the risk of prostate cancer of a patient is P.

$$\text{Logit}(P) = \text{Log}(P/1 - P)$$

$$= \text{intecept} + \sum\nolimits_{i=1}^{n} (\text{coefficient}_i \times \text{transformed}(\text{variable}_i))$$

In the case of model 4, there is 1 variable. The transformation of each variable is applied, then multiplied by

TABLE 14

| No | Variable | Transformation | Log Odd ratio |
|---|---|---|---|
| | (Intercept) | | 5.740625 |
| 1 | % Free.PSA | Log | −1.953958 |

TABLE 15

| Metric | Threshold | Sens | Specs | Acc | Youden |
|---|---|---|---|---|---|
| Max Acc | 0.5481467 | 0.816 | 0.484 | 69.9 | 1.3 |
| Max Youden | 0.6944809 | 0.596 | 0.774 | 65.91 | 1.4 |

TABLE 16

| | Variable | Raw Value | Transformation | Transformed Value | Co-efficient | Partial products |
|---|---|---|---|---|---|---|
| 1 | Intercept | 1 | None | 1 | 5.740625 | 5.740625 |
| 2 | %free PSA | 14.2 | Log | 2.653242 | −1.953958 | −5.18432 |

$$\text{Logit}(P) = \log (P/1 - P) = \text{intercept} + \sum \log \text{ odds ratio}_i \times \log(\text{marker}_i)$$

SUM     0.556302

$$P = \dfrac{\exp(\text{Logit}(P))}{1 + \exp(\text{Logit}(P))}$$

0.635596

The probability of the patient having aggressive CaP is 0.636
If the cutpoint is set at the Youden value of ~0.694, the patient would be classified as
having non-aggressive prostate cancer the co-efficient. Finally the resulting products are summed to give the Log it(P) value. This is then used to determine the probability of aggressive cancer using the formula:

$$P_{(\text{Aggressive prostate cancer})} = \frac{\exp(\text{Logit}(P))}{1 + \exp(\text{Logit}(P))}$$

For example, $$\text{Log it}(P)_{Model\ 4} = 5.740625 - 1.953958 * \text{Log} (\% \text{ Free.PSA})$$

$$P_{(\text{Aggressive Prostate Cancer})} = \frac{\exp(5.740625 - 1.953958 * \text{Log}(\%\text{Free}.PSA)}{1 + \exp(5.740625 - 1.953958 * \text{Log}(\%\text{Free}.PSA))}$$

The results of a ROC curve analysis performed on % Free PSA under Model 4 are shown in FIG. Eight/Tables 14-16.

(e) ROC Analyses on PHI-Model 5

Algorithm outputs for Model 5 (PHI) are indicated below:

P is probability of that a patient has aggressive prostate cancer. In other words, the risk of prostate cancer of a patient is P.

$$\text{Logit}(P) = \text{Log}(P/1 - P)$$

$$= \text{intecept} + \sum\nolimits_{i=1}^{n} (\text{coefficient}_i \times \text{transformed}(\text{variable}_i))$$

In the case of model 5, there is 1 variable. The transformation of each variable is applied, then multiplied by the co-efficient. Finally the resulting products are summed to give the Log it(P) value. This is then used to determine the probability of aggressive cancer using the formula:

$$P_{(Aggressive\ prostate\ cancer)} = \frac{\exp(\text{Logit}(P))}{1 + \exp(\text{Logit}(P))}$$

For example,

Log it $(P)_{Model\ 5} = -8.765445 + 2.397622*\log\ (PHI)$.

$$P_{(Aggressive\ Prostate\ Cancer)} = \frac{\exp(-8.765445 + 2.397622*\log(PHI))}{1 + \exp(-8.765445 + 2.397622*\log(PHI))}$$

The results of a ROC curve analysis performed on PHI under Model 5 are shown in FIG. Nine/Tables 17-19.

TABLE 17

| No | Variable | Transformation | Log Odd ratio |
|---|---|---|---|
| | (Intercept) | | −8.765445 |
| 1 | PHI | Log | 2.397622 |

TABLE 18

| Metric | Threshold | Sens | Specs | Acc | Youden |
|---|---|---|---|---|---|
| Max Acc | 0.4746821 | 0.90 | 0.36 | 70.5 | 1.3 |
| Max Youden | 0.7332056 | 0.51 | 0.90 | 64.8 | 1.4 |

TABLE 19

| | Variable | Raw Value | Transformation | Transformed Value | Co-efficient | Partial products |
|---|---|---|---|---|---|---|
| 1 | Intercept | 1 | None | 1 | −8.765445 | −8.76545 |
| 2 | PHI | 14.2 | Log | 2.653242 | 2.397622 | 6.361471 |

$$\text{Logit}(P) = \log\ (P/1-P) = \text{intercept} + \sum \log\ \text{odds\ ratio}_i \times \log(\text{marker}_i)$$

SUM  −2.40397

$$P = \frac{\exp(\text{Logit}(P))}{1 + \exp(\text{Logit}(P))} \qquad 0.08287$$

The probability of the patient having aggressive CaP is 0.083
If the cutpoint is set at the Youden value of ~0.733, the patient would be classified as
having non-aggressive prostate cancer (f) ROC Analyses on PSA, PV and Leptin-Model 6

Algorithm outputs for Model 6 (PSA, PV and leptin) are indicated below:

P is probability of that a patient has aggressive prostate cancer. In other words, the risk of prostate cancer of a patient is P.

$$\text{Logit}(P) = \text{Log}(P/1-P)$$
$$= \text{intecept} + \sum_{i=1}^{n} (\text{coefficient}_i \times \text{transformed}(\text{variable}_i)$$

In the case of model 6, there are 3 variables. The transformations of each variable are applied, then multiplied by the co-efficients. Finally the resulting products are summed to give the Log it(P) value. This is then used to determine the probability of aggressive cancer using the formula:

$$P_{(Aggressive\ prostate\ cancer)} = \frac{\exp(\text{Logit}(P))}{1 + \exp(\text{Logit}(P))}$$

For example,

Log it $(P)_{Model\ 6} = 3.5843 + 2.0527*\log\ (\text{Central. PSA}) - 1.1245*\log\ (\text{ProstateVolume}) - 0.2974*\log\ (\text{Leptin})$ $$P(\text{Aggressive prostate cancer}) =$$

$$\frac{\exp(3.5843 + 2.0527*\log(Central.PSA) - 1.1245*\log(ProstateVolume) - 0.2974*\log(\text{Leptin}))}{1 + \exp(3.5843 + 2.0527*\log(Central.PSA) - 1.1245*\log(ProstateVolume) - 0.2974*\log(\text{Leptin}))}$$

The results of a ROC curve analysis performed on PSA, PV and leptin under Model 6 are shown in FIG. Ten/Tables 20-22.

TABLE 20

| No | Variable | Transformation | Log Odd ratio |
|---|---|---|---|
| | (Intercept) | | 3.5843 |
| 1 | Central.PSA | Log | 2.0527 |
| 2 | Prostate volume | Log | −1.1245 |
| 3 | Leptin | Log | −0.2974 |

TABLE 21

| Metric | Threshold | Sens | Specs | Acc | Youden |
|---|---|---|---|---|---|
| Max Acc | 0.471 | 0.93 | 0.41 | 75.74 | 1.34 |
| Max Youden | 0.705 | 0.66 | 0.80 | 70.41 | 1.46 |

TABLE 22

| | Variable | Raw Value | Transformation | Transformed Value | Co-efficient | Partial products |
|---|---|---|---|---|---|---|
| 1 | Intercept | 1 | None | | −0.4229547 | −0.4229547 |
| 2 | Central PSA | 5 | Log | 1.609438 | 1.7680206 | 2.845519 |
| 3 | Prostate volume | 56 | Log | 4.025352 | −1.1836569 | −4.764635 |
| 4 | Leptin | 21859.78 | Log | 9.992404 | −0.4264460 | −4.26122 |

$$\text{Logit}(P) = \log\left(P/1 - P\right) = \text{intercept} + \sum \log \text{ odds ratio}_i \times \log(\text{marker}_i)$$

| | | |
|---|---|---|
| SUM | | −6.60329 |

$$P = \frac{\exp(\text{Logit}(P))}{1 + \exp(\text{Logit}(P))}$$ 0.001354

The probability of the patient having aggressive CaP is 0.001354
If the cutpoint is set at the Youden value of ~0.705, the patient would be classified as having non-aggressive prostate cancer PSA, PV and Leptin formed a core combination. Additional models were then developed using these three components as a core/unifying feature and incorporating additional analytes to improve performance.

To further develop multi-variate models, the following steps were used:

1. Imported the combined data set into the R[1] computer program loaded with the following packages BMA[2], VSURF[3,4], caret[5], ROCR[6], pROC[7], stats packages.

[1] R Core Team (2017). R: A language and environment for statistical computing. R Foundation for Statistical Computing, Vienna, Austria. ISBN 3-900051-07-0, URL http://www.R-project.org/

[2] Adrian Raftery, Jennifer Hoeting, Chris Volinsky, Ian Painter and Ka Yee Yeung (2018). BMA: Bayesian Model Averaging. R package version 3.18.8. https://CRAN.R-project.org/package=BMA

[3] Genuer, R. and Poggi, J. M. and Tuleau-Malot, C. (2010), Variable selection using random forests, Pattern Recognition Letters 31 (14), 2225-2236

[4] Genuer, R. and Poggi, J. M. and Tuleau-Malot, C. (2015), VSURF: An R Package for Variable Selection Using Random Forests, The R Journal 7 (2): 19-33

[5] Max Kuhn. Contributions from Jed Wing, Steve Weston, Andre Williams, Chris Keefer, Allan Engelhardt, Tony Cooper, Zachary Mayer, Brenton Kenkel, the R Core Team, Michael Benesty, Reynald Lescarbeau, Andrew Ziem, Luca Scrucca, Yuan Tang, Can Candan and Tyler Hunt. (2018). caret: Classification and Regression Training. R package version 6.0-79. https://CRAN.R-project.org/package=caret

[6] Xavier Robin, Natacha Turck, Alexandre Hainard, et al. (2011) "PROC: an open-source package for R and S+ to analyze and compare ROC curves". BMC Bioinformatics, 7, 77. DOI: 10.1186/1471-2105-12-77

[7] Sing T, Sander O, Beerenwinkel N and Lengauer T (2005). "ROCR: visualizing classifier performance in R." _Bioinformatics_, *21*(20), pp. 7881. <URL: http://rocr.bioinf.mpi-sb.mpg.de>

2. Bayesian Model Averaging (BMA) and Random Forest (RF) functions in R used to generate models using subsets of the 22 analytes and 3 clinical variables.

22 analytes: VEGF, G-CSF, Glypican-1, NT-proANP, Kallikrein 3, HGF, VEGF-C, Tie-2, VEGF R2/KDR/Flk-1, ErbB2/Her2, CXCL13.BLC.BCA-1, IL-7, HE4.WFDC2, MADCAM-1, Leptin, CD40L, IL-18, IL.6.R.Alpha, uPA.Urokinase, PDGF.AB, osteopontin, mesothelin.

3 clinical variables: PSA, age, PV

3. Bayesian Model Averaging (BMA) accounts for the model uncertainty inherent in the variable selection problem by averaging over the best models in the model class according to approximate posterior model probability. The number specifying the maximum ratio for excluding models in Occam's window was set to 20. BMA resulted in the posterior probability that the presence in top models is non-zero (in percent) for each variable.

Top 10 variables having highest posterior probability that each variable is present in the top models were selected for further analysis. They were: Central PSA, age, osteopontin, Prostate Volume, IL-7, VEGF, CD40L, CXCL13.BLC.BCA-1, Leptin, MADCAM-1.

Random Forest (RF) takes a series of random subsets of variables to develop multiple decision trees. Classification (AgCaP or not) is based on agreement between most of the decision trees. In each decision tree, the importance of each variable was calculated.

There are three steps in variable selection procedure: thresholding step, interpretation step, and prediction step. However, in this study there was focus only on the thresholding step. Specifically, RF was dedicated to eliminating irrelevant variables from the data set based on their mean variable importance. Only variables with high mean variable importance (higher than a derived threshold) were shown in results.

14 variables were selected from the Random Forest approach: Central.PSA, IL-7, Prostate Volume, VEGF-C, age, Leptin, Osteopontin, VEGF, Mesothelin, Tie-2, HE4.WFDC2, PDGF.AB, CD40L, Kallikrein 13 analytes (IL-7, VEGF-C, Leptin, Osteopontin, VEGE, mesothelin, Tie-2, HE4.WFDC2, PDGF.AB, CD40L, Kallikrein, CXCL13.BLC.BCA-1, MADCAM-1) and 3 clinical variables (PSA, age, PV) appeared at high frequency in either BMA or RF results. These 16 variables were chosen for further investigation and model development. Of these variables, five (leptin, VEGF, IL-7, Osteopontin, and CD40L) analytes and three clinical variables (PSA, age, PV) overlapped between the BMA and RF results.

4. Based on the population of 169 CaP patients with complete data, a series of multiple logistic regression models were fitted using subsets of variables from the top 13 analytes and 3 clinical variables with the following restrictions: maximum number of variables per model was 8; Kallikrein 3 variable was excluded as it is a redundant measurement of Central.PSA. Note that all the variables (except for age) were transformed by natural log function before the modelling.

5. After the model fitting based on the population, weightings and formula were derived as results of the multiple logistic regression function.

6. The AUCs of models were calculated on the same data set (169 CaP patients) and compared.

7. When the number of maximum number of variables per model was set to 5, the preferred set of markers was: Central.PSA, PV, leptin, Age, IL-7, and VEGF. Models 7a and 7b contain the core components of PSA, PV and $$P_{(Aggressive\ prostate\ cancer)} =$$

38 compared to a chosen cutpoint to call the test positive or negative within defined sensitivity/specificity parameters.

(g) ROC Analyses on PSA, PV, Leptin, Age, IL-7 and VEGF-Model 7a

Algorithm outputs for Model 7a (PSA, PV, Leptin, Age, IL-7 and VEGF) are indicated below:

P is probability of that a patient has aggressive prostate cancer. In other words, the risk of prostate cancer of a patient is P.

$$\mathrm{Logit}(P) = \mathrm{Log}(P/1 - P) = \mathrm{intercept} + \sum_{i=1}^{n} (\mathrm{coefficient}_i \times \mathrm{variable}_i)$$

In the case of model 7a, there are 6 variables. Each variable is multiplied by the co-efficients. Finally the resulting products are summed to give the Log it(P) value. This is then used to determine the probability of aggressive cancer using the formula:

$$P_{(Aggressive\ prostate\ cancer)} = \frac{\exp(\mathrm{Logit}(P))}{1 + \exp(\mathrm{Logit}(P))}$$

For example,

Log it $(P)_{Model\ 7a}$=−6.75+0.2021*Central.PSA+−0.02569*ProstateVolume+−0.000037*Leptin+0.08445*Age+0.008446*VEGF+0.1127*IL-7

$$\frac{\exp(-6.75 + 0.2021 * \mathrm{Central}.PSA + -0.02569 * ProstateVolume - 3.657e - 05 * \mathrm{Leptin} + 0.08445 * \mathrm{Age} + 0.008446 * VEGF + 0.1127 * IL - 7)}{1 + \exp(-6.75 + 0.2021^* \mathrm{Central}.PSA + -0.02569^* ProstateVolume - 3.657e - 05^* \mathrm{Leptin} + 0.08445^* \mathrm{Age} + 0.008446^* VEGF + 0.1127 * IL - 7)}$$

Leptin together with three additional components (Age, IL-7 and VEGF). The models differ in that model 7b uses a log transformation of values (except Age) whereas model 7a does not.

8. Model 8 included 8 variables (Central.PSA, PV, leptin, Age, VEGF, IL-7, Osteopontin, and CD40L) and provided the highest AUC score (0.87)

9. Model 9 was developed by mandating Central.PSA, PV and % free PSA and limiting the number of additional variables to 3. Model 9 consists of Central.PSA, PV, Leptin, % free PSA, HE4.WDC-2 and osteopontin 10. Models 7a, 7b, 8 and 9 were applied on the whole population of 169 CaP patients. Based on their profile, each patient had one risk of AgCaP, which is the outcome of the respective model, ranging from 0 to 100%. Optimal sensitivity/specificity thresholds of each model were determined at which the model had the maximum accuracy or maximum Youden index (=sensitivity+specificity−1).

11. The cut point was determined based on either a defined sensitivity, the point of maximum Youden index or the point of maximum accuracy. This gives defined sensitivity/specificity performance for a "positive/negative" test.

12. For assessing a patient, the variable values are entered into the model, and the output value is a probability of that patient having aggressive CaP. This can then be The results of a ROC curve analysis performed on PSA, PV, Leptin, Age, IL-7 and VEGF under Model 7a are shown in FIG. Eleven/Tables 23-25.

TABLE 23

| No | Variable | Transformation | Log Odd ratio |
|---|---|---|---|
| | (Intercept) | | −6.75 |
| 1 | Central.PSA | None | 0.2021 |
| 2 | ProstateVolume | None | −0.02569 |
| 3 | Leptin | None | −3.657e−05 |
| 4 | Age | None | 0.08445 |
| 5 | VEGF | None | 0.008446 |
| 6 | IL–7 | None | 0.1127 |

TABLE 24

| Metric | Threshold | Sens | Specs | Acc | Youden |
|---|---|---|---|---|---|
| Max Acc | 0.501 | 0.90 | 0.63 | 81.07 | 1.53 |
| Max Youden | 0.514 | 0.89 | 0.64 | 81.07 | 1.54 |

TABLE 25

| | Variable | Raw Value | Transformation | Transformed Value | Co-efficient | Partial products |
|---|---|---|---|---|---|---|
| 1 | Intercept | 1 | None | | −6.75 | −6.75 |
| 2 | Central PSA | 5 | None | 5 | 0.2021 | 1.0105 |
| 3 | Prostate volume | 56 | None | 56 | −0.02569 | −1.43864 |
| 4 | Leptin | 21859.78 | None | 21859.78 | −3.7E−05 | −0.80881 |
| 5 | Age | 58 | None | 58 | 0.08445 | 4.8981 |
| 6 | IL-7 | 7.11 | None | 7.11 | 0.1127 | 0.801297 |
| 7 | VEGF | 47.78 | None | 47.78 | 0.008446 | 0.40355 |

$$\text{Logit}(P) = \log\left(P/1 - P\right) = \text{intercept} + \sum \log \text{ odds ratio}_i \times \text{marker}_i$$

| SUM | −1.884 |
|---|---|

$$P = \frac{\exp(\text{Logit}(P))}{1 + \exp(\text{Logit}(P))} \qquad 0.1330104$$

The probability of the patient having aggressive CaP is 0.1330104
If the cutpoint is set at the Youden value of ~0.515, the patient would be classified as having non-aggressive prostate cancer Algorithm outputs for Model 7b (PSA, PV, Leptin, Age, IL-7 and VEGF) are indicated below:

P is probability of that a patient has aggressive prostate cancer. In other words, the risk of prostate cancer of a patient is P.

$\text{Logit}(P) =$ $$\text{Log}(P/1 - P). = \text{intercept} + \sum_{i=1}^{n} (\text{coefficient}_i \times \text{transformed}(\text{variable}_i).$$

In the case of model 7b, there are 6 variables. The transformations of each variable (except for age) are applied, then multiplied by the co-efficients. Finally the resulting products are summed to give the Log it(P) value. This is then used to determine the probability of aggressive cancer using the formula:

$$P_{(Aggressive\ prostate\ cancer)} = \frac{\exp(\text{Logit}(P))}{1 + \exp(\text{Logit}(P))}$$

For example,

Log it (P)$_{Model\ 7b}$=−5.20325+1.67631*Log (Central.PSA)−1.34584*Log(ProstateVolume)−0.42687*Log (Leptin)+0.0876*Age+0.65834*Log(VEGF)+ 1.25366*Log (IL−7)

$$P_{(Agressive\ prostate\ cancer)} =$$

$$\frac{\begin{array}{c}\exp(-5.20325 + 1.67631*\text{Log}(Central.PSA) - \\ 1.34584*\text{Log}(ProstateVolume) - 0.42687*\text{Log}(Leptin) + \\ 0.0876*\text{Age} + 0.65834*\text{Log}(VEGF) + \\ 1.25366*\text{Log}(IL-7))\end{array}}{\begin{array}{c}1 + \exp(-5.20325 + 1.67631*\text{Log}(Central.PSA) - \\ 1.34584*\text{Log}(ProstateVolume) - 0.42687*\text{Log}(Leptin) + \\ 0.0876*\text{Age} + 0.65834*\text{Log}(VEGF) + \\ 1.25366*\text{Log}(IL-7))\end{array}}$$

The results of a ROC curve analysis performed on PSA, PV, Leptin, Age, IL-7 and VEGF under Model 7b are shown in FIG. Twelve/Tables 26-28.

TABLE 26

| No | Variable | transformation | Log Odd ratio |
|---|---|---|---|
| | (Intercept) | | −5.20325 |
| 1 | Central.PSA | Log | 1.67631 |
| 2 | ProstateVolume | Log | −1.34584 |
| 3 | Leptin | Log | −0.42687 |
| 4 | Age | None | 0.0876 |
| 5 | VEGF | Log | 0.65834 |
| 6 | IL-7 | Log | 1.25366 |

TABLE 27

| Metric | Threshold | Sens | Specs | Acc | Youden |
|---|---|---|---|---|---|
| Max Acc | 0.578 | 0.87 | 0.71 | 81.66 | 1.58 |
| Max Youden | 0.60 | 0.83 | 0.77 | 81.07 | 1.60 |

TABLE 28

|   | Variable | Raw Value | Transformation | Transformed Value | Co-efficient | Partial products |
|---|----------|-----------|----------------|-------------------|--------------|------------------|
| 1 | Intercept | 1 | None | 1 | −5.20325 | −5.20325 |
| 2 | Central PSA | 5 | Log | 1.609438 | 1.67631 | 2.697917014 |
| 3 | Prostate volume | 56 | Log | 4.025352 | −1.34584 | −5.417479736 |
| 4 | Leptin | 21859.78 | Log | 9.992404 | −0.42687 | −4.265457495 |
| 5 | Age | 58 | None | 58 | 0.0876 | 5.0808 |
| 6 | IL-7 | 7.11 | Log | 1.961502 | 0.65834 | 1.291335227 |
| 7 | VEGF | 47.78 | Log | 3.866607 | 1.25366 | 4.847410532 |

$$\text{Logit}(P) = \log\left(P/1 - P\right) = \text{intercept} + \sum \log\ \text{odds ratio}_i \times \log(\text{marker}_i)$$

SUM         −0.968724459

$$P = \frac{\exp(\text{Logit}(P))}{1 + \exp(\text{Logit}(P))} \qquad 0.275134818$$

The probability of the patient having aggressive CaP is 0.275
If the cutpoint is set at the Youden value of 0.6, the patient would be classified as
having non-aggressive prostate cancer (h) ROC Analyses on PSA, PV, Leptin, Age, IL-7, VEGF, Osteopontin and CD40L-Model 8

Algorithm outputs for Model 8 are indicated below:

P is probability of that a patient has aggressive prostate cancer. In other words, the risk of prostate cancer of a patient is P.

$$\text{Logit}(P) =$$

$$\text{Log}(P/1 - P) = \text{intercept} + \sum_{i=1}^{n} (\text{coefficient}_i \times \text{transformed}(\text{variable}_i))$$

In the case of model 8, there are 8 variables. The transformations of each variable (except for age) are applied, then multiplied by the co-efficients. Finally the resulting products were summed to give the Log it(P) value. This was then used to determine the probability of aggressive cancer using the formula:

$$P_{(Aggressive\ prostate\ cancer)} = \frac{\exp(\text{Logit}(P))}{1 + \exp(\text{Logit}(P))}$$

For example,

Log it (P)$_{Model\ 8}$=−0.4229547+0.1035684*age−1.1836569*log(ProstateVolume)+1.7680206*log(Central. PSA)−0.4264460*log(Leptin)+0.5401469*VEGF+1.4127687*IL. 7.−1.2848626*osteopontin+0.7690301*CD40. Ligand The results of a ROC curve analysis performed on Central.PSA, PV, leptin, Age, VEGF, IL-7, Osteopontin, and CD40L under Model 8 are shown in FIG. Thirteen/Tables 29-31.

TABLE 29

| No | Variable | transformation | Log Odd ratio |
|----|----------|----------------|---------------|
|    | (Intercept) |              | −0.42295 |
| 1  | Central.PSA | Log          | 1.76802 |
| 2  | ProstateVolume | Log       | −1.18366 |
| 3  | Leptin | Log               | −0.42645 |
| 4  | Age | None                 | 0.10357 |
| 5  | VEGF | Log                | 0.54015 |
| 6  | IL-7 | Log                | 1.41277 |
| 7  | Osteopontin | Log          | −1.28486 |
| 8  | CD40L | Log               | 0.76903 |

TABLE 30

| Metric | Threshold | Sens | Specs | Acc | Youden |
|--------|-----------|------|-------|-----|--------|
| Max Acc | 0.52 | 0.90 | 0.71 | 84.02 | 1.62 |
| Max Youden | 0.53 | 0.89 | 0.75 | 84.02 | 1.64 |

$$P_{(Aggressive\ prostate\ cancer)} = \frac{\exp(-0.4229547 + 0.1035684 * \text{age} - 1.1836569 * \log(ProstateVolume) + 1.7680206 * \log(Central.PSA) - 0.4264460 * \log(\text{Leptin}) + 0.5401469 * VEGF + 1.4127687 * IL.7. - 1.2848626 * \text{osteopontin} + 0.7690301 * CD40.\text{Ligand})}{1 + \exp(-0.4229547 + 0.1035684 * \text{age} - 1.1836569 * \log(ProstateVolume) + 1.7680206 * \log(Central.PSA) - 0.4264460 * \log(\text{Leptin}) + 0.5401469 * VEGF + 1.4127687 * IL.7. - 1.2848626 * \text{osteopontin} + 0.7690301 * CD40.\text{Ligand})}$$

TABLE 31

|   | Variable | Raw Value | Transformation | Transformed Value | Co-efficient | Partial products |
|---|---|---|---|---|---|---|
| 1 | Intercept | −0.4229547 | None | | 1 | −0.4229547 |
| 2 | Central PSA | 5 | Log | 1.609438 | 1.7680206 | 2.845519 |
| 3 | Prostate volume | 56 | Log | 4.025352 | −1.1836569 | −4.764635 |
| 4 | Leptin | 21859.78 | Log | 9.992404 | −0.4264460 | −4.261221 |
| 5 | Age | 58 | None | 58 | 0.1035684 | 6.006967 |
| 6 | IL-7 | 7.11 | Log | 1.961502 | 1.4127687 | 2.771149 |
| 7 | VEGF | 47.78 | Log | 3.866607 | 0.5401469 | 2.088536 |
| 8 | Osteopontin | 19920.44 | Log | 9.899502 | −1.2848626 | −12.719499 |
| 9 | CD40L | 2640.17 | Log | 7.878599 | 0.7690301 | 6.058880 |

$$\text{Logit}(P) = \log\left(P/1 - P\right) = \text{intercept} + \sum \text{log odds ratio}_i \times$$
$$\log(\text{marker}_i)$$

SUM    −2.39726

$$P = \frac{\exp(\text{Logit}(P))}{1 + \exp(\text{Logit}(P))} \qquad 0.08338187$$

The probability of the patient having aggressive CaP is 0.083
If the cutpoint is set at the Youden value of ~0.53, the patient would be classified as having
non-aggressive prostate cancer 12 analytes were chosen for mandated model development based on their performance in previous modelling approaches (VEGF, Glypican-1, NT-proANP, CXCL13.BLC.BCA-1, Tie-2, HE4.WFDC2, uPA.Urokinase, osteopontin, CD40L, Leptin, IL-7, ErbB2/Her2). 3 clinical variables (Central PSA, % FreePSA, PV) were subjected to multiple logistic regression analysis with the following restriction: only the best 2 or 3 variables were to be added to PSA, % free PSA and prostate volume. AUCs were calculated for each model and compared to that of the base model (PSA, % free PSA and prostate volume) using DeLong's test as well as bootstrap[8] method. Models with a statistically higher AUC were reported.

$$P_{(Aggressive\ prostate\ cancer)} = \frac{\exp(\text{Logit}(P))}{1 + \exp(\text{Logit}(P))}$$

For example,

Log it(P) Model 9=5.0147+1.8264*Log (Central.PSA)−0.7433*Log (ProstateVolume)−0.4531*Log (Leptin)−1.0442*Log (% Free.PSA)+1.4347*Log (HE4.WFDC2)+1.1126*Log (osteopontin)

$$P_{(Aggressive\ prostate\ cancer)} = \frac{\exp(5.0147 + 1.8264^*\text{Log}(\text{Central}.PSA) - 0.7433^*\text{Log}(ProstateVolume) - 0.4531^*\text{Log}(\text{Leptin}) - 1.0442^*\text{Log}(\%\text{Free}.PSA) + 1.4347^*\text{Log}(HE4.WFDC.2) + 1.1126^*\text{Log}(\text{osteopontin})}{1 + \exp(5.0147 + 1.8264^*\text{Log}(\text{Central}.PSA) - 0.7433^*\text{Log}(ProstateVolume) - 0.4531^*\text{Log}(\text{Leptin}) - 1.0442^*\text{Log}(\%\text{Free}.PSA) + 1.4347^*\text{Log}(HE4.WFDC.2) + 1.1126^*\text{Log}(\text{osteopontin})}$$

Model 9 based on Central PSA, % Free PSA, PV, Leptin, osteopontin and HE4.WFDC2 yielded best AUC (0.84). Leptin was present in this model despite not being a mandated variable, further supporting its utility in differentiating patients with aggressive prostate cancer.

Algorithm outputs for Model 9 are indicated below:

P is probability of that a patient has aggressive prostate cancer. In other words, the risk of prostate cancer of a patient is P.

Logit(P) =

$$\text{Log}(P/1 - P) = \text{intercept} + \sum_{i=1}^{n} (\text{coefficient}_i \times \text{transformed}(\text{variable}_i)$$

In the case of model 9, there are 6 variables. The transformations of each variable are applied, then multiplied by the co-efficients. Finally the resulting products are summed to give the Log it(P) value. This is then used to determine the probability of aggressive cancer using the formula:

The results of a ROC curve analysis performed on central PSA, % Free PSA, PV, Leptin, osteopontin and HE4.WFDC2 under Model 9 are shown in FIG. Fourteen/Tables 32-34.

TABLE 32

| No | Variable | Transformation | Log Odd ratio |
|---|---|---|---|
| | (Intercept) | | 5.0147 |
| 1 | Central.PSA | Log | 1.8264 |
| 2 | Prostate Volume | Log | −0.7433 |
| 3 | Leptin | Log | −0.4531 |
| 4 | %.Free.PSA | Log | −1.0442 |
| 5 | HE4.WFDC.2 | Log | 1.4347 |
| 6 | osteopontin | Log | −1.1126 |

TABLE 33

| Metric | Threshold | Sens | Specs | Acc | Youden |
|--------|-----------|------|-------|------|--------|
| Max Acc | 0.63781 | 0.78 | 0.79 | 78.31 | 1.57 |
| Max Youden | 0.63781 | 0.78 | 0.79 | 78.31 | 1.57 |

TABLE 34

| | Variable | Raw Value | Transformation | Transformed Value | Co-efficient | Partial products |
|---|----------|-----------|----------------|-------------------|--------------|------------------|
| 1 | Intercept | 1 | None | 1 | 5.0147 | 5.0147 |
| 2 | Central PSA | 5 | Log | 1.609438 | 1.8264 | 2.939477563 |
| 3 | Prostate volume | 56 | Log | 4.025352 | −0.7433 | −2.992044142 |
| 4 | Leptin | 21859.78 | Log | 9.992404 | −0.4531 | −4.527558252 |
| 5 | %free PSA | 14.2 | Log | 2.653242 | −1.0442 | −2.770515296 |
| 6 | HE4/WFDC-2 | 3886.01 | Log | 8.265138 | 1.4347 | 11.85799349 |
| 7 | Osteopontin | 19920.44 | Log | 9.899502 | −1.1126 | −11.01418593 |

$$\text{Logit}(P) = \log\left(P/1 - P\right) = \text{intercept} + \sum \log \text{ odds ratio}_i \times \log(\text{marker}_i)$$

SUM    −1.492132564

$$P = \frac{\exp(\text{Logit}(P))}{1 + \exp(\text{Logit}(P))} \qquad 0.183601857$$

The probability of the patient having aggressive CaP is 0.184
If the cutpoint is set at the Youden value of ~0.64, the patient would be classified as
having non-aggressive prostate cancer DRE status is easier to obtain than prostate volume and also differentiated aggressive from non-aggressive prostate cancer well in the test population. Algorithm outputs for DRE (Model 10) are indicated below:

P is probability of that a patient has aggressive prostate cancer. In other words, the risk of prostate cancer of a patient is P.

$$\text{Logit}(P) =$$

$$\text{Log}(P/1 - P) = \text{intercept} + \sum_{i=1}^{n} (\text{coefficient}_i \times \text{transformed}(\text{variable}_i))$$

In the case of model 1b, there are 1 variable. The transformations of DRE is applied, then multiplied by the coefficients. Finally the resulting products are summed to give the Log it(P) value. This is then used to determine the probability of aggressive cancer using the formula:

$$P_{(\text{Aggressive prostate cancer})} = \frac{\exp(\text{Logit}(P))}{1 + \exp(\text{Logit}(P))}$$

For example,

Log it $(P)_{\text{Model DRE}}$=0.4470+1.0411*DRE (1 if suspicious, 0 if others).

$$P(\text{Aggressive prostate cancer}) = \frac{\exp(0.4470 + 1.0411 * DRE)}{1 + \exp(0.4470 + 1.0411 * DRE)}$$

The results of a ROC curve analysis performed on DRE under Model 10 are shown in FIG. Fifteen/Tables 35-37.

TABLE 35

| No | Variable | Transformation | Log Odd ratio |
|----|----------|----------------|---------------|
| | (Intercept) | None | 0.4470 |
| 1 | DRE (suspicious) | None | 1.0411 |

TABLE 36

| Metric | Threshold | Sens | Specs | Acc |
|--------|-----------|------|-------|------|
| Max Acc | 0.6099291 | 1 | 0 | 65.36 |
| Max Youden | 0.8157895 | 0.27 | 0.89 | 48.05 |

TABLE 37

| | Variable | Raw Value | Transformation | Transformed Value | Co-efficient | Partial products |
|---|----------|-----------|----------------|-------------------|--------------|------------------|
| 1 | Intercept | 1 | None | | 0.4470 | 0.4470 |
| 2 | DRE (Suspicious) | 0 | None | | 1.0411 | 0 |

TABLE 37-continued

| Variable | Raw Value | Transformation | Transformed Value | Co-efficient | Partial products |
|---|---|---|---|---|---|
| $\text{Logit}(P) = \log\left(P/1 - P\right) = \text{intercept} + \sum \log \text{ odds ratio}_i \times \log(\text{marker}_i)$ | | | | SUM | 0.4470 |
| $P = \dfrac{\exp(\text{Logit}(P))}{1 + \exp(\text{Logit}(P))}$ | | | | | 0.609925721 |

The probability of the patient having aggressive CaP is 0.6099
If the cutpoint is set at the Youden value of ~0.82, the patient would be classified as
having non-aggressive prostate cancer DRE was substituted for prostate volume and new models developed using combinations that had performed well with prostate volume. Algorithm outputs for Model 11 (PSA, DRE, Leptin, Age, IL-7 and VEGF) are indicated below:

P is probability of that a patient has aggressive prostate cancer. In other words, the risk of prostate cancer of a patient is P.

Logit (P) =

$$\text{Log}\left(P/1 - P\right) = \text{intercept} + \sum_{i=1}^{n} (\text{coefficient}_i \times \text{transformed (variable}_i)$$

In the case of model 1, there are 1 variable. The transformations of PSA is applied, then multiplied by the co-efficients. Finally the resulting products are summed to give the Log it(P) value. This is then used to determine the probability of aggressive cancer using the formula:

$$P(\text{Aggressive prostate cancer}) = \frac{\exp(\text{Logit}(P))}{1 + \exp(\text{Logit}(P))}$$

For example,
Log it $(P)_{Model}$=−9.05328+0.06691×Age+1.32477× DRE+1.78725*log(Central. PSA)−0.45548×log (Leptin)+0.77175×log(VEGF)+1.05352×log(IL−7)

$P(\text{Aggressive prostate cancer}) =$ $$\frac{\exp(-9.05328 + 0.06691 \times \text{Age} + 1.32477 \times DRE + 1.78725 * \log(\text{Central}.PSA) - 0.45548 \times \log(\text{Leptin}) + 0.77175 \times}{1 + \exp(-9.05328 + 0.06691 \times \text{Age} + 1.32477 \times DRE + 1.78725 * \log(\text{Central}.PSA) - 0.45548 \times \log(\text{Leptin}) + 0.77175}+$$

The results of a ROC curve analysis performed on PSA, DRE, Leptin, Age, IL-7 and VEGF under Model 11 are shown in FIG. Sixteen/Tables 38-40. Model 11 retained a good AUC of 0.827 compared to the original model 7b (AUC 0.840) indicating that DRE could be substituted for prostate volume with acceptable AUC performance.

TABLE 38

| No | Variable | Transformation | Log Odd ratio |
|---|---|---|---|
| | (Intercept) | | −9.05328 |
| 1 | age | | 0.06691 |
| 2 | DRE | | 1.32477 |
| 3 | Central.PSA | Log | 1.78725 |
| 4 | Leptin..51 | Log | −0.45548 |
| 5 | VEGF..26. | Log | 0.77175 |
| 6 | IL.7..29. | Log | 1.05352 |

TABLE 39

| Metric | Threshold | Sens | Specs | Acc |
|---|---|---|---|---|
| Max Acc | 0.5004626 | 0.90 | 0.60 | 79.1 |
| Max Youden | 0.6039236 | 0.75 | 0.82 | 77.7 |

TABLE 40

| | Variable | Raw Value | Transformation | Transformed Value | Co-efficient | Partial products |
|---|---|---|---|---|---|---|
| 1 | Intercept | 1 | None | 1 | −9.05328 | −9.05328 |
| 2 | Age | 58 | None | 58 | 0.06691 | 3.88078 |
| 3 | DRE (suspicious) | 0 | None | 0 | 1.32477 | 0 |
| 4 | Central PSA | 5 | Log | 1.609438 | 1.78725 | 2.876468 |
| 5 | Leptin | 21859.78 | Log | 9.992404 | −0.45548 | −4.55134 |
| 6 | VEGF | 7.11 | Log | 1.961502 | 0.77175 | 1.513789 |
| 7 | IL-7 | 47.78 | Log | 3.866607 | 1.05352 | 4.073548 |

TABLE 40-continued

| Variable | Raw Value | Transformation | Transformed Value | Co-efficient | Partial products |
|---|---|---|---|---|---|
| $\text{Logit}(P) = \log\left(P/1 - P\right) = \text{intercept} + \sum \log \text{ odds ratio}_i \times \log(\text{marker}_i)$ | | | | SUM | −1.26004 |
| $P = \dfrac{\exp(\text{Logit}(P))}{1 + \exp(\text{Logit}(P))}$ | | | | | 0.220968 |

The probability of the patient having aggressive CaP is 0.220968
If the cutpoint is set at the Youden value of ~0.603, the patient would be classified as
having non-aggressive prostate cancer DRE had been successfully substituted for prostate volume with model 11. A similar substitution was therefore performed using Osteopontin (another analyte that appeared in high performing models) instead of IL-7 to generate a combination of DRE, PSA, Age, Leptin, VEGF and Osteopontin (Model 12). Algorithm outputs for model 12 are shown below:

P is probability of that a patient has aggressive prostate cancer. In other words, the risk of prostate cancer of a patient is P.

$\text{Logit}(P) =$ $$\text{Log}\left(P/1 - P\right) = \text{intercept} + \sum_{i=1}^{n} (\text{coefficient}_i \times \text{transformed (variable}_i))$$

In the case of model 1, there are 1 variable. The transformations of PSA is applied, then multiplied by the co-efficients. Finally the resulting products are summed to give the Log it(P) value. This is then used to determine the probability of aggressive cancer using the formula:

$$P_{(Aggressive\ prostate\ cancer)} = \frac{\exp(\text{Logit}(P))}{1 + \exp(\text{Logit}(P))}$$

For example,
Log it $(P)_{Model}$=−0.7819839+0.0639165×Age+1.2799035×DRE+1.2799035+log(Central. PSA)−0.4206831×log (Leptin)+0.8441242×log (VEGF)−0.6754611×log (Osteopontin)

$P(\text{Aggressive prostate cancer}) =$ $$\frac{\begin{aligned}&\exp(-0.7819839 + 0.0639165 \times \text{Age} + 1.2799035 \times DRE + \\ &1.2799035 * \log(\text{Central}.PSA) - 0.4206831 \times \log(\text{Leptin}) + \\ &0.8441242 \times \log(VEGF) - 0.6754611 \times \log(\text{Osteopontin}))\end{aligned}}{\begin{aligned}&1 + \exp(-0.7819839 + 0.0639165 \times \text{Age} + 1.2799035 \times DRE + \\ &1.2799035 * \log(\text{Central}.PSA) - 0.4206831 \times \log(\text{Leptin}) + \\ &0.8441242 \times \log(VEGF) - 0.6754611 \times \log(\text{Osteopontin}))\end{aligned}}$$

The results of a ROC curve analysis performed on PSA, DRE, Leptin, Age, VEGF and Osteopontin under Model 12 are shown in FIG. Seventeen/Tables 41-43. Model 12 retained a good AUC of 0.83 compared to the original model 11 (AUC 0.827) indicating that osteopontin could be substituted for IL-7 with acceptable AUC performance.

TABLE 41

| No | Variable | Transformation | Log Odd ratio |
|---|---|---|---|
| | (Intercept) | | −0.7819839 |
| 1 | age | | 0.0639165 |
| 2 | DRE | | 1.2799035 |
| 3 | Central.PSA | Log | 2.0504175 |
| 4 | Leptin..51 | Log | −0.4206831 |
| 5 | VEGF..26. | Log | 0.8441242 |
| 6 | Osteopontin | Log | −0.6754611 |

TABLE 42

| Metric | Threshold | Sens | Specs | Acc |
|---|---|---|---|---|
| Max Acc | 0.4497495 | 0.94 | 0.52 | 79.33 |
| Max Youden | 0.6111408 | 0.76 | 0.79 | 77.09 |

TABLE 43

| | Variable | Raw Value | Transformation | Transformed Value | Co-efficient | Partial products |
|---|---|---|---|---|---|---|
| 1 | Intercept | 1 | None | 1 | −0.7819839 | −0.78198 |
| 2 | Age | 58 | None | 58 | 0.0639165 | 3.707157 |
| 3 | DRE (suspicious) | 0 | None | 0 | 1.2799035 | 0 |
| 4 | Central PSA | 5 | Log | 1.609438 | 2.0504175 | 3.30002 |
| 5 | Leptin | 21859.78 | Log | 9.992404 | −0.4206831 | −4.20364 |
| 6 | VEGF | 7.11 | Log | 1.961502 | 0.8441242 | 1.655751 |
| 7 | Osteopontin | 19920.44 | Log | 9.899502 | −0.6754611 | −6.68673 |

$$\text{Logit}(P) = \log\left(P/1 - P\right) = \text{intercept} + \sum \log \text{ odds ratio}_i \times \log(\text{marker}_i)$$

SUM −3.00942

$$P = \frac{\exp(\text{Logit}(P))}{1 + \exp(\text{Logit}(P))}$$

0.047002

The probability of the patient having aggressive CaP is 0.5243951
If the cutpoint is set at the Youden value of ~0.706, the patient would be classified as
having non-aggressive prostate cancer Glypican-1 has previously performed well in differentiating prostate cancer from normal or benign patient samples (Campbell et al, 2017, Levin et al 2018)[8,9]. Algorithm outputs for GPC-1 under model 13 are shown below:

[8] Campbell et al 2017. Detection of glypican-1 (GPC-1) expression in urine cell sediments in prostate cancer. PLOS One. 2018 Apr. 19; 13 (4): e0196017. doi: 10.1371/journal.pone.0196017. eCollection 2018.
[9] Levin et al 2018. Development of a reliable assay to measure glypican-1 in plasma and serum reveals circulating glypican-1 as a novel prostate cancer biomarker. Oncotarget. 2018 Apr. 27; 9 (32): 22359-22367. doi: 10.18632/oncotarget.25009. eCollection 2018 Apr. 27.

P is probability of that a patient has aggressive prostate cancer. In other words, the risk of prostate cancer of a patient is P.

$$\text{Logit}(P) =$$

$$\log\left(P/1 - P\right) = \text{intercept} + \sum_{i=1}^{n} (\text{coefficient}_i \times \text{transformed } (\text{variable}_i)$$

In the case of model 1, there are 1 variable. The transformations of PSA is applied, then multiplied by the co-efficients. Finally the resulting products are summed to give the Log it(P) value. This is then used to determine the probability of aggressive cancer using the formula:

$$P_{(Aggressive\ prostate\ cancer)} = \frac{\exp(Logit(P))}{1 + \exp(Logit(P))}$$

For example, $$\text{Log it } (P)_{Model} = 1.8437572 - 0.1248303 + \log(\text{GPC}-1)$$

$$P(\text{Aggressive prostate cancer}) =$$

$$\frac{\exp(1.8437572 - 0.1248303 * \log(GPC - 1))}{1 + \exp(1.8437572 - 0.1248303 * \log(GPC - 1))}$$

The results of a ROC curve analysis performed on Glypican-1 under Model 13 are shown in FIG. Eighteen/Tables 44-46

TABLE 44

| No | Variable | Transformation | Log Odd ratio |
|---|---|---|---|
| | (Intercept) | | 1.8437572 |
| 1 | GPC-1 | Log | −0.1248303 |

TABLE 45

| Metric | Threshold | Sens | Specs | Acc |
|---|---|---|---|---|
| Max Acc | 0.6364949 | 0.99 | 0.02 | 65.4 |
| Max Youden | 0.6490466 | 0.75 | 0.32 | 60.4 |

TABLE 46

| | Variable | Raw Value | Transformation | Transformed Value | Co-efficient | Partial products |
|---|---|---|---|---|---|---|
| 1 | Intercept | 1 | None | 1 | 1.8437572 | 1.843757 |
| 2 | GPC-1 | 13407.45 | Log | 9.503566 | −0.1248303 | −1.18633 |

$$\text{Logit}(P) = \log\left(P/1 - P\right) = \text{intercept} + \sum \log \text{ odds ratio}_i \times \log(\text{marker}_i)$$

SUM 0.657424

TABLE 46-continued

| Variable | Raw Value | Transformation | Transformed Value | Co-efficient | Partial products |
|---|---|---|---|---|---|
| | | | $P = \dfrac{\exp(\text{Logit}(P))}{1 + \exp(\text{Logit}(P))}$ | | 0.658682 |

The probability of the patient having aggressive CaP is 0.658682
If the cutpoint is set at the Youden value of ~0.649, the patient would be classified as
having aggressive prostate cancer The results from the ROC curve analysis and worked example indicate that on its own GPC-1 has limited ability to differentiate aggressive and non-aggressive prostate cancer in this patient trial set, despite performing well in other sample sets.

To test whether GPC-1 could contribute to the performance of the biomarker combinations identified previously, it was added as to the analyte combinations used for Models 11 and 12 to generate Model 14 (DRE, PSA, Age, Leptin, VEGF, IL-7 and GPC-1) and Model 15 (DRE, PSA, Age, Leptin, VEGF, Osteopontin and GPC-1) respectively.

Algorithms for Model 14 are shown below:

P is probability of that a patient has aggressive prostate cancer. In other words, the risk of prostate cancer of a patient is P.

$Logit\ (P) =$ $$Log\left(P/1 - P\right) = \text{intercept} + \sum_{i=1}^{n} (\text{coefficient}_i \times \text{transformed (variable}_i)$$

In the case of model 1, there are 1 variable. The transformations of PSA is applied, then multiplied by the co-efficients. Finally the resulting products are summed to give the Log it(P) value. This is then used to determine the probability of aggressive cancer using the formula:

$$P_{(Aggressive\ prostate\ cancer)} = \frac{\exp(\text{Logit}(P))}{1 + \exp(\text{Logit}(P))}$$

For example,

Log it $(P)_{Model\ 1} = -4.5807193 + 0.0686203 \times Age + 1.3580828 \times DRE + 1.7851868 + log(Central.\ PSA) -$ 0.4064453×log (Leptin)+0.8059637×log (VEGF)+ 1.1115531×log (IL−7)−0.5485615×log (GPC1)

$P(\text{Aggressive prostate cancer}) =$ $$\frac{\begin{array}{l}\exp(-4.5807193 + 0.0686203 \times \text{Age} + \\ 1.3580828 \times DRE + 1.7851868 * \log(\text{Central}.PSA) - \\ 0.4064453 \times \log(\text{Leptin}) + 0.8059637 \times \log(VEGF) + \\ 1.115531 \times \log\ (IL - 7) - 0.5485615 \times \log(GPC - 1))\end{array}}{\begin{array}{l}1 + \exp(-4.5807193 + 0.068620223 \times \text{Age} + \\ 1.3580828 \times DRE + 1.7851868 * \log(\text{Central}.PSA) - \\ 0.4064453 \times \log(\text{Leptin}) + 0.8059637 \times \log(VEGF) + \\ 1.1115531 \times \log(IL - 7) - 0.5485615 \times \log(GPC - 1))\end{array}}$$

The results of a ROC curve analysis performed under Model 14 are shown in FIG. Nineteen/Tables 47-49.

TABLE 47

| No | Variable | Transformation | Log Odd ratio |
|---|---|---|---|
| | (Intercept) | | −4.5807193 |
| 1 | age | | 0.0686203 |
| 2 | DRE | | 1.3580828 |
| 3 | Central.PSA | Log | 1.7851868 |
| 4 | Leptin..51 | Log | −0.4064453 |
| 5 | VEGF..26. | Log | 0.8059637 |
| 6 | IL.7..29. | Log | 1.1115531 |
| 7 | GPC-1 | Log | −0.5485615 |

TABLE 48

| Metric | Threshold | Sens | Specs | Acc |
|---|---|---|---|---|
| Max Acc | 0.4898448 | 0.92 | 0.61 | 81.0 |
| Max Youden | 0.5509978 | 0.86 | 0.69 | 79.9 |

TABLE 49

| | Variable | Raw Value | Transformation | Transformed Value | Co-efficient | Partial products |
|---|---|---|---|---|---|---|
| 1 | Intercept | 1 | None | 1 | −4.5807193 | −4.58072 |
| 2 | Age | 58 | None | 58 | 0.0686203 | 3.979977 |
| 3 | DRE (suspicious) | 0 | None | 0 | 1.3580828 | 0 |
| 4 | Central PSA | 5 | Log | 1.609438 | 1.7851868 | 2.873147 |
| 5 | Leptin | 21859.78 | Log | 9.992404 | −0.4064453 | −4.06137 |
| 6 | VEGF | 7.11 | Log | 1.961502 | 0.8059637 | 1.580899 |
| 7 | IL-7 | 47.78 | Log | 3.866607 | 1.1115531 | 4.297939 |

TABLE 49-continued

| | Variable | Raw Value | Transformation | Transformed Value | Co-efficient | Partial products |
|---|---|---|---|---|---|---|
| 8 | GPC-1 | 13407.45 | Log | 9.503566 | −0.5485615 | −5.21329 |

$$\text{Logit}(P) = \log\left(P/1 - P\right) = \text{intercept} + \sum \log \text{ odds ratio}_i \times$$
$$\log(\text{marker}_i)$$

| | |
|---|---|
| | SUM −1.12341 |

$$P = \frac{\exp(\text{Logit}(P))}{1 + \exp(\text{Logit}(P))}$$   0.245379

The probability of the patient having aggressive CaP is 0.245379
If the cutpoint is set at the Youden value of ~0.550, the patient would be classified as
having non-aggressive prostate cancer Algorithms for Model 15 (DRE, PSA, Age, Leptin, VEGF, Osteopontin, GPC-1) are shown below:

P is probability of that a patient has aggressive prostate cancer. In other words, the risk of prostate cancer of a patient is P.

$\text{Logit}(P) =$ $$\text{Log}\left(P/1 - P\right) = \text{intercept} + \sum_{i=1}^{n}(\text{coefficient}_i \times \text{transformed (variable}_i))$$

In the case of model 1, there are 1 variable. The transformations of PSA is applied, then multiplied by the co-efficients. Finally the resulting products are summed to give the. Log it(P) value. This is then used to determine the probability of aggressive cancer using the formula:

$$P_{(\text{Aggressive prostate cancer})} = \frac{\exp(\text{Logit}(P))}{1 + \exp(\text{Logit}(P))}$$

For example, $\text{Log it (P)}_{Model} = 0.7699219 + 0.0642377 \times \text{Age} + 1.2897028 \times \text{DRE} + 2.0477033 \quad \log(\text{Central.PSA}) - 0.4024161 \times \log (\text{Leptin}) + 0.8531346 \times \log (\text{VEGF}) - 0.6665009 \times \log (\text{Osteopontin}) - 0.1922037 \times \log (\text{GPC1})$ $P(\text{Aggressive prostate cancer}) =$ $$\frac{\begin{array}{l}\exp(0.7699219 + 0.0642377 \times \text{Age} + \\ 1.2897028 \times DRE + 2.0477033 * \log(\text{Central}.PSA) - \\ 0.4024161 \times \log(\text{Leptin}) + 0.8531346 \times \log(VEGF) - \\ 0.6665009 \times \log\ (\text{Osteopontin}) - 0.1922037 \times \log(GPC1))\end{array}}{\begin{array}{l}1 + \exp(0.7699219 + 0.0642377 \times \text{Age} + \\ 1.2897028 \times DRE + 2.0477033 * \log(\text{Central}.PSA) - \\ 0.4024161 \times \log(\text{Leptin}) + 0.8531346 \times \log(VEGF) - \\ 0.6665009 \times \log(\text{Osteopontin}) - 0.1922037 \times \log(GPC1))\end{array}}$$

The results of a ROC curve analysis performed under Model 15 are shown in FIG. Twenty/Tables 50-52.

TABLE 50

| No | Variable | Transformation | Log Odd ratio |
|---|---|---|---|
| | (Intercept) | | 0.7699219 |
| 1 | age | | 0.0642377 |
| 2 | DRE | | 1.2897028 |
| 3 | Central.PSA | Log | 2.0477033 |
| 4 | Leptin | Log | −0.4024161 |
| 5 | VEGF | Log | 0.8531346 |
| 6 | osteopontin | Log | −0.6665009 |
| 7 | GPC-1 | Log | −0.1922037 |

TABLE 51

| Metric | Threshold | Sens | Specs | Acc |
|---|---|---|---|---|
| Max Acc | 0.5835473 | 0.79 | 0.77 | 78.2 |
| Max Youden | 0.5835473 | 0.79 | 0.77 | 78.2 |

TABLE 52

| | Variable | Raw Value | Transformation | Transformed Value | Co-efficient | Partial products |
|---|---|---|---|---|---|---|
| 1 | Intercept | 1 | None | 1 | 0.7699219 | 0.769922 |
| 2 | Age | 58 | None | 58 | 0.0642377 | 3.725787 |
| 3 | DRE (suspicious) | 0 | None | 0 | 1.2897028 | 0 |
| 4 | Central PSA | 5 | Log | 1.609438 | 2.0477033 | 3.295652 |
| 5 | Leptin | 21859.78 | Log | 9.992404 | −0.4024161 | −4.0211 |
| 6 | VEGF | 7.11 | Log | 1.961502 | 0.8531346 | 1.673425 |
| 7 | Osteopontin | 19920.44 | Log | 9.899502 | −0.6665009 | −6.59803 |

TABLE 52-continued

| | Variable | Raw Value | Transformation | Transformed Value | Co-efficient | Partial products |
|---|---|---|---|---|---|---|
| 8 | GPC-1 | 13407.45 | Log | 9.503566 | −0.1922037 | −1.82662 |

$$\text{Logit}(P) = \log\left(P/1 - P\right) = \text{intercept} + \sum \log \text{ odds ratio}_i \times \log(\text{marker}_i)$$

SUM    −2.98097

$$P = \frac{\exp(\text{Logit}(P))}{1 + \exp(\text{Logit}(P))}$$

0.048293

The probability of the patient having aggressive CaP is 0.048293
If the cutpoint is set at the Youden value of ~0.583, the patient would be classified as
having non-aggressive prostate cancer The co-efficients of models 14 and 15 were optimised for the 320 evaluable patient population and ROC curves generated to generate models 14b and 15b. These models both generated AUCs of 0.78.

The results of a ROC curve analysis of model 14b are shown in FIG. Twenty One and Tables 53 and 54

TABLE 53

| Variable | Transformation | Coefficients |
|---|---|---|
| (Intercept) | None | −4.26174 |
| age | None | 0.02629 |
| DRE (suspicious) | None | 1.23361 |
| Leptin..51. | Log | 0.01532 |
| Central.PSA | Log | 1.75012 |
| VEGF..26. | Log | 0.24167 |
| Glypican.1..18. | Log | −0.33408 |
| IL.7..29. | log | 0.22626 |

TABLE 54

| Metric | Threshold | Sens | Specs | Acc |
|---|---|---|---|---|
| Max Acc | 0.4207465 | 0.56 | 0.82 | 73% |
| Max Youden | 0.3140104 | 0.77 | 0.68 | 71% |
| 90% Sens | 0.2265336 | 0.90 | 0.49 | 64% |
| 95% Sens | 0.1941881 | 0.95 | 0.36 | 58% |

The results of a ROC curve analysis of model 15b are shown in FIG. Twenty Two and Tables 55 and 56

TABLE 55

| Variable | Transformation | Coefficients |
|---|---|---|
| (Intercept) | None | −1.27921 |
| age | None | 0.02995 |
| DRE (suspicious) | None | 1.25389 |
| Leptin..51. | Log | 0.01584 |
| Central.PSA | Log | 1.81229 |
| VEGF..26. | Log | 0.29007 |
| Glypican.1..18. | Log | −0.23037 |
| osteopontin..54. | Log | −0.40648 |

TABLE 56

| Metric | Threshold | Sens | Specs | Acc |
|---|---|---|---|---|
| Max Acc | 0.4255975 | 0.55 | 0.84 | 73% |
| Max Youden | 0.29268 | 0.84 | 0.62 | 70% |

TABLE 56-continued

| Metric | Threshold | Sens | Specs | Acc |
|---|---|---|---|---|
| 90% Sens | 0.23212836 | 0.90 | 0.48 | 63% |
| 95% Sens | 0.1755499 | 0.95 | 0.31 | 54% |

To improve the performance of the algorithms, further models were developed by adding % free PSA (Models 16 and 17).

Model 16 consisted of total PSA, DRE, leptin, subject age, VEGF, IL-7, GPC-1, % free PSA and had an AUC of 0.83. The results of a ROC curve analysis of model 16 are shown in FIG. Twenty Three and Tables 57 and 58

TABLE 57

| Variable | Transformation | Coefficients |
|---|---|---|
| Intercept | None | −2.96938 |
| age | None | 0.0646 |
| DRE (suspicious) | None | 1.24482 |
| Leptin..51. | Log | −0.09042 |
| Central.PSA | Log | 1.03407 |
| VEGF..26. | Log | 0.15471 |
| Glypican.1..18. | Log | 0.19431 |
| IL.7..29. | Log | 0.33706 |
| % freePSA | Log | −2.43722 |

TABLE 58

| Metric | Threshold | Sens | Specs | Acc |
|---|---|---|---|---|
| Max Acc | 0.3642402 | 0.45 | 0.96 | 77% |
| Max Youden | 0.6456393 | 0.77 | 0.76 | 76% |
| 90% Sens | 0.18478217 | 0.90 | 0.51 | 65% |
| 95% Sens | 0.13624859 | 0.95 | 0.39 | 59% |

Model 17 consisted of total PSA, DRE, leptin, subject age, VEGF, osteopontin, GPC-1, % free PSA and had an AUC of 0.83
The results of a ROC curve analysis of model 17 are shown in FIG. Twenty Four and Tables 59 and 60

TABLE 59

| Variable | Transformation | Coefficients |
|---|---|---|
| (Intercept) | None | −0.23634 |
| age | None | 0.06684 |
| DRE (suspicious) | None | 1.27017 |
| Leptin..51. | Log | −0.09274 |
| Central.PSA | Log | 1.11534 |

US 12,618,843 B2

59

TABLE 59-continued

| Variable | Transformation | Coefficients |
|---|---|---|
| VEGF..26. | Log | 0.19596 |
| Glypican.1..18. | Log | 0.28369 |
| osteopontin..54. | Log | -0.33707 |
| % freePSA | Log | -2.40324 |

TABLE 60

| Metric | Threshold | Sens | Specs | Acc |
|---|---|---|---|---|
| Max Acc | 0.4530268 | 0.64 | 0.84 | 77% |
| Max Youden | 0.3229175 | 0.81 | 0.73 | 76% |
| 90% Sens | 0.21539157 | 0.90 | 0.58 | 65% |
| 95% Sens | 0.14210313 | 0.95 | 0.37 | 58% |

(n) Development of Additional Models for AgCaP Vs NOT AgCaP (i.e. Non-Aggressive CaP and No Cap)

Further models were developed for AgCaP vs NOT-AgCaP using 320 evaluable patients (62 CaP, 117 AgCaP and 141 no CaP). The variables chosen for model development consisted of both clinical factors and soluble analytes and were as follows:

PSA, patient Age, VEGF, Glypican-1, NTProANP, VEGF-C, Tie2, VEGFR2, ErbB2 Her2, CXCK13/BLC/BCA1, IL-7, HE4, Leptin, CD40L, uPA/Urokinase, Osteopontin, pro2PSA, % free PSA, Race, prior biopsy status, DRE and family history.

Model 18 was derived from Bayesian Model Averaging (BMA) analysis and logistic regression modelling and contained the following components:

total PSA, DRE, leptin, subject age, prior negative biopsy, VEGF-C, osteopontin, GPC-1, CD40L, proPSA, % free PSA Model 18 has an AUC of 0.88 at differentiating AgCaP from NOT AgCaP.

The results of a ROC curve analysis of model 18 are shown in FIG. Twenty-Five and Tables 61 and 62

TABLE 61

| Variable | Transformation | Coefficients |
|---|---|---|
| (Intercept) | None | -1.56456 |
| age | None | 0.0803 |

60

TABLE 61-continued

| Variable | Transformation | Coefficients |
|---|---|---|
| DRE (suspicious) | None | 1.43254 |
| Leptin..51. | Log | -0.22202 |
| CD40.Ligand..74. | Log | 0.2475 |
| Prior negative biosy | None | -1.00958 |
| Central.PSA | Log | -0.63633 |
| VEGF-C..38. | Log | 0.73594 |
| Glypican.1..18. | Log | 0.22249 |
| % freePSA | Log | -4.2971 |
| osteopontin..54. | Log | -0.56006 |
| proPSA | Log | 2.42583 |

TABLE 62

| | Cut-point | Sens | Spec | Acc |
|---|---|---|---|---|
| Max Youden | 0.4687652 | 0.70 | 0.89 | 82.4 |
| Max Acc | 0.4687652 | 0.70 | 0.89 | 82.4 |
| 90% Sens | 0.1967927 | 0.90 | 0.64 | 72.6 |
| 95% Sens | 0.1268048 | 0.95 | 0.49 | 64.8 |

1.5 Performance of Different Models at Fixed Sensitivities of 90% and 95% for the Differentiation of AgCaP Vs noAgCaP The specificity of the different models, components and current tests (PSA, % free PSA and PHI) for differentiating AgCaP vs noAgCaP were examined at the Youden Index and at fixed sensitivities of 90% and 95% (Table 63). Models 7a and b, 8, 9, 11, 12, 14 and 15 showed consistently higher specificities than other tests at these cutpoints.

Inclusion of GPC-1 marginally increased the AUC (0.828 vs 0.827) for Model 14 compared to Model 11 and also increased the specificity (63% vs. 60%) at the 90% sensitivity threshold (see Table 63). Model 14 also showed higher sensitivity at the Youden index compared to Model 12 (86% Sensitivity vs 75%). As the Youden index is considered the point on the ROC curve that gives the most stable test performance characteristics, inclusion of GPC-1 may be beneficial in algorithms that require a high sensitivity. Inclusion of GPC-1 in model 15 did not change the AUC or the performance at the Youden index compared to model 12, but resulted in slightly lower specificities at 90% (58% vs 55%) and 95% (50% vs 47%).

TABLE 63

| Model | Components | AUC (95% confidence interval) | Max Youden Sens | Max Youden Spec | Sens | Spec | Sens | Spec |
|---|---|---|---|---|---|---|---|---|
| 1 | PSA | 0.738 (0.663-0.813) | 0.52 | 0.86 | 0.90 | 0.33 | 0.95 | 0.26 |
| 2 | Prostate Volume (PV) | 0.614 (0.526-0.702) | 0.76 | 0.46 | 0.90 | 0.14 | 0.95 | 0.09 |
| 3 | Leptin | 0.574 (0.484-0.665) | 0.26 | 10.89 | 0.90 | 0.16 | 0.95 | 0.11 |
| 4 | % free PSA | 0.713 (0.635-0.791) | 0.60 | 10.77 | 0.90 | 0.24 | 0.95 | 0.16 |
| 5 | PHI | 0.745 (0.673-0.818) | 0.52 | 0.89 | 0.90 | 0.36 | 0.95 | 0.24 |
| 6 | PSA, PV, Leptin | 0.789(0.719-0.859) | 0.66 | 0.80 | 0.90 | 0.43 | 10.95 | 0.30 |
| 7a | PSA, PV, Leptin, Age, VEGF, IL-7 | 0.832 (0.77-0.90) | 0.90 | 0.63 | 0.90 | 0.63 | 0.95 | 0.39 |
| 7b | PSA, PV, Leptin, Age, VEGF, IL-7 | 0.840 (0.76-0.91) | 0.83 | 0.77 | 0.90 | 0.55 | 0.95 | 0.38 |

TABLE 63-continued

| Model | Components | AUC (95% confidence interval) | Max Youden | | | | | |
|---|---|---|---|---|---|---|---|---|
| | | | Sens | Spec | Sens | Spec | Sens | Spec |
| 8 | PSA, PV, Leptin, Age, VEGF, IL-7, osteopontin, CD40L | 0.866 (0.81-0.93) | 0.89 | 0.75 | 0.90 | 0.71 | 10.95 | 0.43 |
| 9 | PSA, PV, Leptin, % free PSA, HE4, osteopontin | 0.838 (0.78-0.90) | 0.78 | 0.79 | 0.90 | 0.55 | 0.95 | 0.30 |
| 10 | DRE | 0.576 (0.52-0.63) | 0.27 | 0.89 | n/a | n/a | n/a | n/a |
| 11 | PSA, DRE, Leptin, Age, VEGF, IL-7 | 0.827 (0.763-0.891) | 0.75 | 0.82 | 0.90 | 0.60 | 0.95 | 0.37 |
| 12 | PSA, DRE, Leptin, Age, VEGF, osteopontin | 0.830 (0.766-0.894) | 0.76 | 0.79 | 0.90 | 0.58 | 0.95 | 0.50 |
| 13 | GPC-1 | 0.489 (0.400-0.579) | 0.75 | 0.32 | 0.90 | 0.06 | 0.95 | 0.05 |
| 14 | PSA, DRE, Leptin, Age, VEGF, IL-7, GPC-1 | 0.828 (0.764-0.892) | 0.86 | 0.69 | 0.90 | 0.63 | 0.95 | 0.36 |
| 15 | PSA, DRE, Leptin, Age, VEGF, osteopontin, GPC-1 | 0.830 (0.766-0.894) | 0.79 | 0.77 | 0.90 | 0.55 | 0.95 | 0.47 |

1.6 Performance of Different Models at Fixed Sensitivities of 90% and 95% for the Differentiation of AgCaP Vs NOT-AgCaP The specificity of the different models for differentiating AgCaP vs NOT-AgCaP were examined at the Youden Index and at fixed sensitivities of 90% and 95% (Table 64).

Inclusion of % free PSA increased the AUCs of Models 16 and 17 compared to the parent models 14b and 15b and showed higher specificities than other tests at the 90% and 95% sensitivity cutpoints. Model 18 had the highest AUC performance of AgCaP vs NOT AgCaP (0.88).

TABLE 64

| Model | Components | AUC (95% confidence interval) | Max Youden | | | | | |
|---|---|---|---|---|---|---|---|---|
| | | | Sens | Spec | Sens | Spec | Sens | Spec |
| 14b | PSA, DRE, Leptin, Age, VEGF, IL-7, GPC-1 | 0.78 (0.73-0.83) | 0.78 | 0.68 | 0.90 | 0.49 | 0.95 | 0.36 |
| 15b | PSA, DRE, Leptin, Age, VEGF, osteopontin, GPC-1 | 0.78 (0.73-0.83) | 0.84 | 0.62 | 0.90 | 0.48 | 0.95 | 0.31 |
| 16 | PSA, DRE, Leptin, Age, VEGF, IL-7, GPC-1, % free PSA | 0.83 (0.79-0.88) | 0.77 | 0.76 | 0.90 | 0.51 | 0.95 | 0.39 |
| 17 | PSA, DRE, Leptin, Age, VEGF, osteopontin, GPC-1, % free PSA | 0.83 (0.79-0.88) | 0.60 | 0.77 | 0.90 | 0.58 | 0.95 | 0.37 |
| 18 | PSA, DRE, Leptin, Age, CD-40L, VEGF-C, osteopontin, GPC-1, % free PSA, prior negative biopsy, proPSA | 0.88 (0.84-0.92) | 0.70 | 0.89 | 0.90 | 0.64 | 0.95 | 0.49 |

1.7 Comparison of Model 7b Results with Other Clinical Tests in Different PSA Ranges-Total PSA, % Free PSA and PHI-AgCaP Vs noAgCaP The performance of model 7b was compared to existing clinical tests for prostate cancer (PSA, pro2PSA, % free PSA and PHI) at differentiating between aggressive and non-aggressive prostate cancer in this patient sample set. FIG. twenty-six shows ROC curves for MiCheck® model 7b with PSA, pro2PSA, % free PSA and PHI in different groups of patients. Panel A shows patients with all PSA values, panel B shows the performance of the tests in patients with PSA values from 4-10 ng/ml, while panel C shows performance of the test in patients with normal DRE, >50 years of age and PSA 4-10 ng/ml (the indication for the PHI test). In all groups, the Model 7b algorithm shows a higher ROC curve than the other tests.

Table 65 shows the comparative performance (AUC, sensitivity, specificity) of these tests together with the odds ratios, and p values. The Model 7b algorithm is superior to all other tests in all patient subgroups and is statistically significantly different for all tests in all groups with the exception of PHI in the normal DRE, >50 years of age and PSA 4-10 ng/ml subgroup (likely due to small numbers in this group).

TABLE 65

| Component | All PSA range 62 Non AgCaP vs 117 AgCaP | | |
| --- | --- | --- | --- |
| | Odds ratio | AUC | p value |
| Pro2PSA | 1.04 (1.01-1.08) | 0.638 (0.552-0.725) | 0.01 |
| Central PSA | 1.30 (1.13-1.49) | 0.734 (0.655-0.812) | <0.001 |
| % free PSA | 0.89 (0.84-0.95) | 0.695 (0.613-0.778) | <0.001 |
| PHI | 1.04 (1.02-1.07) | 0.739 (0.664-0.815) | <0.001 |
| MiCheck ® | 289.38 (46.47-1802.26) | 0.827 (0.761-0.893) | <0.001 |

| Comparison of p values | All PSA range 62 Non AgCaP vs 117 AgCaP |
| --- | --- |
| Central PSA vs pro2PSA | 0.029 |
| Central PSA vs % Free PSA | 0.428 |
| Central PSA vs PHI | 0.007 |
| Central PSA vs MiCheck ® | 0.0001 |
| pro2PSA vs % Free PSA | 0.44 |
| pro2PSA vs PHI | 0.89 |
| pro2PSA vs MiCheck ® | 0.011 |
| % Free PSA vs PHI | 0.353 |
| % Free PSA vs MiCheck ® | 0.006 |
| PHI vs MiCheck ® | 0.04 |

| Component | PSA 4-10 ng/ml 41 Non AgCaP vs 77 AgCaP | | |
| --- | --- | --- | --- |
| | Odds ratio | AUC | p value |
| Pro2PSA | 1.03 (0.99-1.07) | 0.564 (0.454-0.673) | 0.207 |
| Central PSA | 1.41 (1.06-1.89) | 0.628 (0.524-0.733) | 0.02 |
| % free PSA | 0.93 (0.86-0.99) | 0.625 (0.518-0.733) | 0.032 |
| PHI | 1.04 (1.01-1.07) | 0.671 (0.571-0.772) | 0.003 |
| MiCheck ® | 242.77 (22.89-2574.66) | 0.797 (0.709-0.885) | 5.15E−06 |

| Comparison of p values | PSA 4-10 ng/ml 41 Non AgCaP vs 77 AgCaP |
| --- | --- |
| Central PSA vs pro2PSA | 0.296 |
| Central PSA vs % Free PSA | 0.531 |
| Central PSA vs PHI | 0.0329 |
| Central PSA vs MiCheck ® | 0.001 |
| pro2PSA vs % Free PSA | 0.967 |
| pro2PSA vs PHI | 0.493 |
| pro2PSA vs MiCheck ® | 0.003 |
| % Free PSA vs PHI | 0.485 |
| % Free PSA vs MiCheck ® | 0.01 |
| PHI vs MiCheck ® | 0.05 |

| Component | PSA 4-10 ng/ml normal DRE 32 No CaP vs 43 AgCaP | | |
| --- | --- | --- | --- |
| | Odds ratio | AUC | p value |
| Pro2PSA | 1.03 (0.98-1.08) | 0.598 (0.461-0.734) | 0.249 |
| Central PSA | 1.55 (1.08-2.22) | 0.663 (0.537-0.789) | 0.017 |
| % free PSA | 0.94 (0.86-1.02) | 0.594 (0.460-0.728) | |
| PHI | 1.05 (1.02-1.09) | 0.694 (0.571-0.816) | 0.006 |
| MiCheck ® | 233.43 (15.21-3581.66) | 0.819 (0.718-0.919) | 9.09E−05 |

| Comparison of p values | PSA 4-10 ng/ml normal DRE 32 Non AgCaP vs 43 AgCaP |
| --- | --- |
| Central PSA vs pro2PSA | 0.376 |
| Central PSA vs % Free PSA | 0.979 |
| Central PSA vs PHI | 0.177 |
| Central PSA vs MiCheck ® | 0.009 |
| pro2PSA vs % Free PSA | 0.444 |
| pro2PSA vs PHI | 0.67 |
| pro2PSA vs MiCheck ® | 0.015 |
| % Free PSA vs PHI | 0.198 |
| % Free PSA vs MiCheck ® | 0.003 |
| PHI vs MiCheck ® | 0.082 |

1.7 Detection of Patients with Aggressive CaP Using the Test Assay

Models 7b, 8, 11, 12, 14 and 15 were developed to differentiate non-aggressive from aggressive prostate cancer patients. In clinical use, they would be applied to patients who present with elevated PSA and would be used to guide a biopsy decision as shown in FIG. two. To test the models' utility in this situation, they were applied to data from all evaluable patient from Arm 2 of the trial using the cutpoints previously determined for each model. The test result for each patient was classified as positive or negative and the number of each were established. The breakdown of each group was determined in terms of no cancer, non-aggressive (GS3+3) and aggressive (GS 3+4 and above) to determine true positives, true negatives, false positives, false negatives, positive predictive values (PPV) and negative predictive values (NPVs). Model 7b (FIGS. twenty-seven and twenty-eight), Model 8 (FIGS. twenty-nine and thirty), Model 11. (FIGS. thirty-one and thirty-two), Model 12 (FIGS. thirty-three and thirty-four), Model 14 (FIGS. thirty-five and thirty-six) and Model 15 (FIGS. thirty-seven and thirty-eight) were evaluated with a cutpoint at 95% sensitivity. The frequency distribution of no cancer, non-aggressive cancer and aggressive prostate cancers is shown for each test population, together with the classifications of the respective test. At the chosen cutpoints, the detection rates for aggressive cancers are shown. The number of biopsies that could be saved as a result of negative test results are also shown together with the number of Gleason≥3+4 or Gleason≥4+3 cancers missed.

The results are summarised in Table 66. Note that the specificities at 95% sensitives may be different to Table 63 as those shown in Table 66 refer to the performance on the larger data set that also contains patients with no prostate cancer, whereas Table 63 shows performance in the aggressive and non-aggressive cancer set only.

Inclusion of GPC-1 resulted in a small increase the number of total cancers detected for Models 14 and 15 compared to Models 11 and 12. The increase was due to an increase in the detection of GS3+3 cancers with no loss in detection of GS≥3+4 cancers.

The invention claimed is:

1. A method for diagnosing aggressive prostate cancer (CaP) in a test subject, comprising:
   (a) detecting one or more analyte/s in a biological sample from the test subject to thereby obtain an analyte level for each said analyte in the test subject's biological sample, and obtaining a measurement of two or more clinical variables from the test subject; and
   (b) applying a suitable algorithm and/or transformation to a combination of the clinical variable measurements and analyte level/s of the test subject to thereby generate a test subject score value for comparison to a threshold value;
   (c) determining that the test subject has aggressive CaP when the subject test score value is above the threshold value; and
   (d) treating the subject diagnosed with aggressive CaP with one or more of surgery, radiation, or drugs,
   wherein:
   the one or more analyte/s comprise or consist of leptin,
   the two or more clinical variables comprise at least two of: total prostate-specific antigen (PSA), digital rectal examination (DRE), subject age, prostate volume, and
   the threshold value is determined by:
   detecting said one or more analyte/s in a series of biological samples obtained from a population of subjects having aggressive CaP and from a population of control subjects not having aggressive CaP, to thereby obtain an analyte level for each said analyte in each said biological sample of the series;

TABLE 66

| Model | Components | Sens | Spec | Positive | Negative | Biopsies saved (%) | Missed GS ≥ 3 + 4 (%) | Missed GS ≥ 4 + 3 (%) | PPV GS ≥ 3 + 4 | NPV GS ≥ 3 + 4 | NPV GS ≥ 4 + 3 |
|---|---|---|---|---|---|---|---|---|---|---|---|
| 7b | PSA, PV, Leptin, Age, VEGF, IL-7 | 0.95 | 0.47 | 211 | 97 | 32% | 6 (5%) | 1 (2%) | 51% | 94% | 99% |
| 8 | PSA, PV, Leptin, Age, VEGF, IL-7, osteopontin, CD40L | 0.95 | 0.44 | 217 | 91 | 30% | 6 (5%) | 2 (3%) | 52% | 93% | 98% |
| 11 | PSA, DRE, Leptin, Age, VEGF, IL-7 | 0.95 | 0.31 | 251 | 69 | 22% | 6 (5%) | 2 (3%) | 44% | 91% | 97% |
| 12 | PSA, DRE, Leptin, Age, VEGF, osteopontin | 0.95 | 0.39 | 234 | 86 | 27% | 6 (5%) | 3 (5%) | 47% | 93% | 95% |
| 14 | PSA, DRE, Leptin, Age, VEGF, IL-7, GPC-1 | 0.95 | 0.31 | 251 | 69 | 22% | 6 (5%) | 2 (3%) | 44% | 91% | 97% |
| 15 | PSA, DRE, Leptin, Age, VEGF, osteopontin, GPC-1 | 0.95 | 0.38 | 237 | 83 | 26% | 6 (5%) | 3 (5%) | 47% | 93% | 96% |

Table 66 indicates that the different models all have high negative predictive values for GS≥3+4 prostate cancers. Models containing prostate volume have higher specificities and biopsies saved that those using DRE.

combining each of said one or more analyte levels of the series with measurements of said two or more clinical variables obtained from each said subject from the population of subjects having aggressive CaP and from each subject from the population of control subjects, in a manner that allows discrimination between aggressive CaP and an absence of aggressive CaP, to thereby generate the threshold value;

and wherein the two or more clinical variables and the one or more analyte/s comprise any one of the following:

total PSA, prostate volume, leptin, subject age, IL-7 and VEGF;

total PSA, prostate volume, leptin, subject age, IL-7, VEGF, osteopontin and CD40L;

total PSA, % free PSA, prostate volume, leptin, osteopontin and HE4.WFDC2;

total PSA, DRE, leptin, subject age, VEGF and IL-7;

total PSA, DRE, leptin, subject age, VEGF, osteopontin;

total PSA, DRE, leptin, subject age, VEGF, IL-7, GPC-1;

total PSA, DRE, leptin, subject age, VEGF, osteopontin, GPC-1;

total PSA, DRE, leptin, subject age, VEGF, IL-7, GPC-1, % free PSA;

total PSA, DRE, leptin, subject age, VEGF, osteopontin, GPC-1, % free PSA;

total PSA, DRE, leptin, subject age, prior negative biopsy, VEGF-C, osteopontin, GPC-1, CD40L, proPSA, % free PSA.

2. The method of claim 1, wherein the population of control subjects comprises subjects that do not have prostate cancer and subjects that have non-aggressive prostate cancer.

3. A method for discerning whether a test subject has non-aggressive or aggressive prostate cancer (CaP), comprising:

(a) detecting one or more analyte/s in a biological sample from the test subject to thereby obtain an analyte level for each said analyte in the test subject's biological sample, and obtaining a measurement of two or more clinical variable/s from the test subject; and (b) applying a suitable algorithm and/or transformation to a combination of the clinical variable measurements and analyte level/s to thereby generate a test subject score value for comparison to a threshold value;

(c) determining that the test subject has aggressive CaP when the subject test score value is above the threshold value or determining that the test subject has non-aggressive CaP when the subject test score value is below the threshold value; and (d) treating the subject diagnosed with aggressive CaP with one or more of surgery, radiation, or drugs, wherein the test subject has previously been determined to have prostate cancer or a likelihood of having prostate cancer (e.g. by any one or more of a PSA-based test, digital rectal examination (DRE), family history, an ultrasound-based test, magnetic resonance imaging (MRI), a urine biomarker test, an exosome-based test), the one or more analyte/s comprise or consist of leptin, the two or more clinical variables comprise at least two of:

total PSA, DRE, subject age, prostate volume, and the threshold value is determined by:

detecting said one or more analyte/s in a series of biological samples obtained from a population of subjects having aggressive CaP and from a population of control subjects having non-aggressive CaP, to thereby obtain an analyte level for each said analyte in each said biological sample of the series;

combining each of said one or more analyte levels of the series with measurements of said two or more clinical variables obtained from each subject from the population of subjects having aggressive CaP and from each subject from the population of control subjects, to thereby generate the threshold value;

and wherein the two or more clinical variables and the one or more analyte/s comprise any one of the following:

total PSA, prostate volume, leptin, subject age, IL-7 and VEGF;

total PSA, prostate volume, leptin, subject age, IL-7, VEGF, osteopontin and CD40L;

total PSA, % free PSA, prostate volume, leptin, osteopontin and HE4.WFDC2;

total PSA, DRE, leptin, subject age, VEGF and IL-7;

total PSA, DRE, leptin, subject age, VEGF, osteopontin;

total PSA, DRE, leptin, subject age, VEGF, IL-7, GPC-1;

total PSA, DRE, leptin, subject age, VEGF, osteopontin, GPC-1;

total PSA, DRE, leptin, subject age, VEGF, IL-7, GPC-1, % free PSA;

total PSA, DRE, leptin, subject age, VEGF, osteopontin, GPC-1, % free PSA;

total PSA, DRE, leptin, subject age, prior negative biopsy, VEGF-C, osteopontin, GPC-1, CD40L, proPSA, % free PSA.

4. The method of claim 1 or claim 3, wherein the population of control subjects has non-aggressive CaP as defined by a Gleason score of 3+3.

5. The method of claim 1 or 3, comprising selecting a subset of the combined analyte/s and/or clinical variable measurements to generate the threshold value.

6. The method of claim 1 or 3, wherein said combining of each of said one or more analyte levels of the series with said measurements of the two or more clinical variables comprises combining a logistic regression score of the two or more clinical variable measurements and the one or more analyte level/s in a manner that maximizes said discrimination, in accordance with the formula:

$$\text{Logit}(P) = \text{Log}(P/1 - P) = \text{intercept} +$$

$$\sum_{i=1}^{N} \left( \text{coefficient}_i \times \text{transformed (variable}_i) \right) \quad P = \frac{\exp(\text{Logit}(P))}{1 + \exp(\text{Logit}(P))}$$

wherein:

P is probability that the test subject has aggressive prostate cancer, the coefficient$_i$ is the natural log of the odds ratio of the variable, the transformed variable$_i$ is the natural log of the variable$_i$ value, excluding a variable age;

or in accordance with the formula:

$$\text{Logit}(P) =$$

$$\text{Log}(P/1 - P) = \text{intercept} + \sum_{i=1}^{N} \left( \text{coefficient}_i \times \text{transformed (variable}_i) + \right.$$

$$\left. \text{coefficient}_{Age} \times \text{Age} \quad P = \frac{\exp(\text{Logit}(P))}{1 + \exp(\text{Logit}(P))} \right.$$

wherein:

P is probability that the test subject has aggressive prostate cancer, the coefficient$_i$ is the natural log of the odds ratio of the variable, the transformed variable$_i$ is the natural log of the variable$_i$ value, or in accordance with the formula:

$$\text{Logit}(P) = \text{Log}\left(P/1 - P\right) = \text{intercept} + \sum_{i=1}^{N}$$

$$\left(\text{coefficient}_i \times (\text{variable}_i) + \text{coefficient}_{Age} \times \text{Age}\ \ P = \frac{\exp(\text{Logit}(P))}{1 + \exp(\text{Logit}(P))}\right)$$

wherein:

P is probability that the test subject has aggressive prostate cancer, and the coefficient$_i$ is the natural log of the odds ratio of the variable.

7. The method of claim 1 or 3, wherein said applying a suitable algorithm and/or transformation to the combination of the clinical variable measurements and analyte level/s comprises use of an exponential function, a logarithmic function, a power function and/or a root function.

8. The method of claim 1 or 3, wherein the suitable algorithm and/or transformation applied to the combination of the clinical variable measurements and analyte level/s of the test subject is in accordance with the formula:

$$\text{Logit}(P) = \text{Log}\left(P/1 - P\right) = \text{intercept} +$$

$$\sum_{i=1}^{N}\left(\text{coefficient}_i \times \text{transformed}\ (\text{variable}_i)P = \frac{\exp(\text{Logit}(P))}{1 + \exp(\text{Logit}(P))}\right)$$

wherein:

P is probability of that the test subject has aggressive prostate cancer, the coefficient$_i$ is the natural log of the odds ratio of the variable, the transformed variable$_i$ is the natural log of the variable$_i$ value, excluding a variable age;

or in accordance with the formula:

$$\text{Logit}(P) =$$

$$\text{Log}\left(P/1 - P\right) = \text{intercept} + \sum_{i=1}^{N}\left(\text{coefficient}_i \times \text{transformed}\ (\text{variable}_i) +\right.$$

$$\left.\text{coefficient}_{Age} \times \text{Age}\ \ P = \frac{\exp(\text{Logit}(P))}{1 + \exp(\text{Logit}(P))}\right)$$

wherein:

P is probability of that the test subject has aggressive prostate cancer, the coefficient$_i$ is the natural log of the odds ratio of the variable, the transformed variable$_i$ is the natural log of the variable$_i$ value;

or in accordance with the formula:

$$\text{Logit}(P) = \text{Log}\left(P/1 - P\right) = \text{intercept} + \sum_{i=1}^{N}$$

$$\left(\text{coefficient}_i \times (\text{variable}_i) + \text{coefficient}_{Age} \times \text{Age}\ \ P = \frac{\exp(\text{Logit}(P))}{1 + \exp(\text{Logit}(P))}\right)$$

wherein:

P is probability that the test subject has aggressive prostate cancer, the coefficient$_i$ is the natural log of the odds ratio of the variable;

and said suitable algorithm and/or transformation is used to generate the subject test score that is compared to the threshold value to thereby determine whether or not the test subject has aggressive prostate cancer.

9. The method of claim 1 or 3, wherein said combining of each said analyte level of the series with measurements of said two or more clinical variables obtained from each said subject of the populations maximizes said discrimination.

10. The method of claim 1 or 3, wherein said combining of each said analyte level of the series with the measurements of two or more clinical variables obtained from each said subject of the populations is conducted in a manner that:

(i) reduces the misclassification rate between the subjects having aggressive CaP and said control subjects; and/or (ii) increases sensitivity in discriminating between the subjects having aggressive CaP and said control subjects; and/or (iii) increases specificity in discriminating between the subjects having aggressive CaP and said control subjects.

11. The method of claim 10, wherein said combining in a manner that reduces the misclassification rate between the subjects having aggressive CaP and said control subjects comprises selecting a suitable true positive and/or true negative rate and/or minimizes the misclassification rate optionally by identifying a point where the true positive rate intersects the true negative rate.

12. The method of claim 10, wherein said selecting the threshold value from the combined clinical variable measurement/s and combined analyte level/s in a manner that increases specificity and/or sensitivity in discriminating between the subjects having aggressive CaP and said control subjects increases or maximizes said specificity.

13. The method of claim 1 or 3, wherein the two or more clinical variables and the one or more analytes consist of any one of the following:

total PSA, prostate volume, leptin, subject age, IL-7 and VEGF;

total PSA, prostate volume, leptin, subject age, IL-7, VEGF, osteopontin and CD40L;

total PSA, % free PSA, prostate volume, leptin, osteopontin and HE4.WFDC2;

total PSA, DRE, leptin, subject age, VEGF and IL-7;

total PSA, DRE, leptin, subject age, VEGF, osteopontin;

total PSA, DRE, leptin, subject age, VEGF, IL-7, GPC-1;

total PSA, DRE, leptin, subject age, VEGF, osteopontin, GPC-1;

total PSA, DRE, leptin, subject age, VEGF, IL-7, GPC-1, % free PSA;

total PSA, DRE, leptin, subject age, VEGF, osteopontin, GPC-1, % free PSA;

total PSA, DRE, leptin, subject age, prior negative biopsy, VEGF-C, osteopontin, GPC-1, CD40L, proPSA, % free PSA.

14. The method of claim 1 or 3, wherein the test subject has previously received a positive indication of aggressive prostate cancer, optionally by digital rectal exam (DRE) and/or by PSA testing.

15. The method of claim 1 or 3, wherein said detecting of one or more analyte/s in the biological sample from the test subject comprises:

(i) measuring one or more fluorescent signals indicative of each said analyte level;

(ii) obtaining a measurement of weight/volume of said analyte/s in the biological sample;

(iii) measuring an absorbance signal indicative of each said analyte level; or (iv) using a technique selected from the group consisting of: mass spectrometry, a protein array technique, high performance liquid chromatography (HPLC), gel electrophoresis, radiolabeling, and any combination thereof.

16. The method of claim 1 or 3, wherein each said sample is contacted with first and second antibody populations for detection of each said analyte, wherein each said antibody population has binding specificity for one of said analytes, and the first and second antibody populations have different analyte binding specificities, optionally wherein the first and/or second antibody populations are labelled with a label selected from the group consisting of a radiolabel, a fluorescent label, a biotin-avidin amplification system, a chemiluminescence system, microspheres, and colloidal gold.

17. The method of claim 16, wherein binding of each said antibody population to the analyte is detected by a technique selected from the group consisting of: immunofluorescence, radiolabeling, immunoblotting, Western blotting, enzyme-linked immunosorbent assay (ELISA), flow cytometry, immunoprecipitation, immunohistochemistry, biofilm test, affinity ring test, antibody array optical density test, and chemiluminescence.

18. The method of claim 1 or 3, wherein the series of biological samples obtained from each said population and the test subject's biological sample are each whole blood, serum, plasma, saliva, tear/s, urine, or tissue.

19. The method of claim 1 or 3, wherein said test subject, said population of subjects having aggressive CaP, and said population of control subjects are human.

20. The method of claim 1 or 3, wherein the method further comprises a step of biopsy prior to treating the subject diagnosed with aggressive CaP, to confirm said diagnosis.

* * * * *